US008236931B2

(12) United States Patent
De Wildt et al.

(10) Patent No.: US 8,236,931 B2
(45) Date of Patent: Aug. 7, 2012

(54) PREVENTION OF AGGREGATION OF IMMUNOGLOBULIN LIGHT OR HEAVY CHAINS

(75) Inventors: Rudolf M. T. De Wildt, Cambridge (GB); Leo C James, Cambridge (GB); Philip C Jones, Cambridge (GB); Oliver Schon, Cambridge (GB); Gregory Paul Winter, Cambridge (GB)

(73) Assignee: Glaxo Group Limited (GB)

( * ) Notice: Subject to any disclaimer, the term of this patent is extended or adjusted under 35 U.S.C. 154(b) by 333 days.

(21) Appl. No.: 12/447,908

(22) PCT Filed: Oct. 26, 2007

(86) PCT No.: PCT/EP2007/061514
§ 371 (c)(1),
(2), (4) Date: Apr. 30, 2009

(87) PCT Pub. No.: WO2008/052933
PCT Pub. Date: May 8, 2008

(65) Prior Publication Data
US 2010/0047237 A1 Feb. 25, 2010

(30) Foreign Application Priority Data

Oct. 30, 2006 (GB) .................................. 0621513.1
Dec. 5, 2006 (WO) ............... PCT/GB2006/004559

(51) Int. Cl.
*C12P 21/08* (2006.01)
*C07K 16/00* (2006.01)
*C07K 17/00* (2006.01)
*C07K 17/14* (2006.01)
*A61K 39/395* (2006.01)
*A61K 39/00* (2006.01)

(52) U.S. Cl. ............... 530/387.3; 530/387.1; 530/391.1; 530/391.3; 530/391.9; 424/130.1; 424/133.1; 424/134.1; 424/178.1

(58) Field of Classification Search .................. None
See application file for complete search history.

(56) References Cited

U.S. PATENT DOCUMENTS

| 4,816,567 | A | 3/1989 | Cabilly et al. |
| 5,643,872 | A | 7/1997 | Ali et al. |
| 5,831,012 | A | 11/1998 | Nilson et al. |
| 6,008,058 | A | 12/1999 | Spatola et al. |
| 2005/0053973 | A1 | 3/2005 | Kolkman et al. |
| 2005/0089932 | A1 | 4/2005 | Kolkman et al. |
| 2005/0164301 | A1 | 7/2005 | Kolkman et al. |

FOREIGN PATENT DOCUMENTS

| AU | 2003 262 458 | 12/2003 |
| EP | 0 486 525 | 2/1991 |
| EP | 0 739 353 | 7/1995 |
| EP | 1 134 231 | 9/2001 |
| WO | WO 87/05631 | 9/1987 |
| WO | WO 93/05072 | 3/1993 |
| WO | WO 94/04678 | 3/1994 |
| WO | WO 97/49805 | 12/1997 |
| WO | WO 98/01560 | 1/1998 |
| WO | WO 98/58965 | 12/1998 |
| WO | WO 99/23221 | 5/1999 |
| WO | WO 99/37681 | 7/1999 |
| WO | WO 00/15803 | 3/2000 |
| WO | WO 00/24884 | 5/2000 |
| WO | WO 2000/29004 | 5/2000 |
| WO | WO 00/43507 | 7/2000 |
| WO | WO 00/65067 | 11/2000 |
| WO | WO 00/69907 | 11/2000 |
| WO | WO 01/40310 | 6/2001 |
| WO | WO 03/002609 | 1/2003 |
| WO | WO 03/035694 | 5/2003 |
| WO | WO 03/054015 | 7/2003 |
| WO | WO 2004/003019 | 1/2004 |
| WO | WO 2004/015425 | 2/2004 |
| WO | WO 2004/041862 | 5/2004 |
| WO | WO 2004/041863 | 5/2004 |
| WO | WO 2004/041865 | 5/2004 |
| WO | WO 2004/044011 | 5/2004 |
| WO | WO 2004/058821 | 7/2004 |
| WO | WO 2004/061026 | 7/2004 |
| WO | WO 2004/062551 | 7/2004 |
| WO | WO 2004/101790 | 11/2004 |
| WO | WO 2005/033130 | 4/2005 |
| WO | WO 2005/035572 | 4/2005 |
| WO | WO 2005/044858 | 5/2005 |
| WO | WO 2006/059108 | 6/2006 |
| WO | WO 2006/076640 | 7/2006 |
| WO | WO 2006/085518 | 8/2006 |
| WO | WO 2007/066106 | 6/2007 |

OTHER PUBLICATIONS

Khurana, Souillac, Coats, Minert, Ionescu-Zanetti, Carter, Solomon, and Fink. A model for amyloid fibril formation in immunoglobulin light chains based on comparison of amyloidogenic and benign proteins and specific antibody binding. Amyloid: J Proten Folding Disord. 2003. vol. 10, pp. 97-109.*

(Continued)

*Primary Examiner* — Anne M. Gussow
(74) *Attorney, Agent, or Firm* — William Peter Long; William T. Han

(57) ABSTRACT

An inhibitor of the aggregation of immunoglobulin chains is provided. The inhibitor may comprise or consist of a polypeptide which comprises or consists of (a) an amino acid sequence corresponding to the amino acid sequence of the FR1 region of an immunoglobulin light chain variable domain, or part thereof which includes amino acid residue 12, (b) an amino acid sequence corresponding to the amino acid sequence of the immunoglobulin-binding domain of bacterial superantigen Protein L, or part thereof, and/or (c) an amino acid sequence corresponding to the amino acid sequence of the immunoglobulin-binding domain of streptococcal protein G, or part thereof, or a variant, fusion or derivative thereof, or a fusion of a variant or derivative thereof which retains the ability of the parent polypeptide to inhibit aggregation of immunoglobulin chains, or domains thereof. Other versions of the inhibitor are also provided.

86 Claims, 11 Drawing Sheets

OTHER PUBLICATIONS

Figure 1:
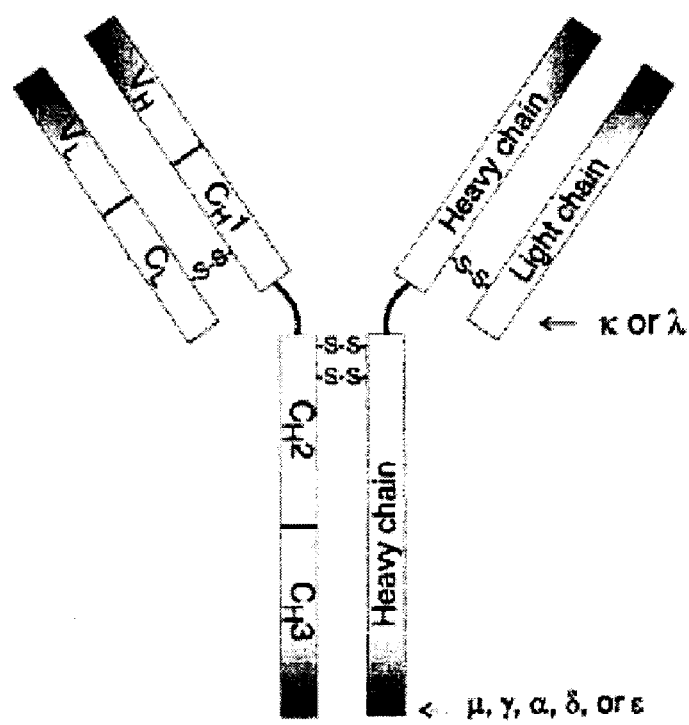

Hudson and Kortt. High Avidity scFv multimers; diabodies and triabodies. Journal of Immunological Methods, 1999. vol. 231, pp. 177-189.*

Skolnick and Fetrow. From genes to protein structure and function: novel applications of computational approaches in the genomic era. Trends in Biotechnology, 2000. vol. 18, pp. 34-39.*

Burgess, Shaheen, Ravera, Donohue, and Winkles. Possible dissociation of the heparin-binding and mitogenic activities of heparin binding (acidic fibroblast) growth factor-1 from its receptor binding activities by site directed mutagenesis of a single lysine residue. Journal of Cell Biology, 1990. vol. 111, pp. 2129-2138.*

Lazar, Watanabe, Dalton, and Sporn. Transforming growth factor alpha: mutation of aspartic acid 47 and leucine 48 results in different biological activites. Molecular and Cellular Biology, 1988. vol. 8, pp. 1247-1252.*

Khurana, et al., "A model for amyloid fibril formation in immunoglobulin light chains based on comparison of amyloidogenic and benign proteins and specific antibody binding," *Amyloid: The International Journal of Experimental and Clinical Investigation: The Official Journal of the International Society of Amyloidosis*, vol. 10, No. 2, pp. 97-109 (2003).

Solomon, et al., "Therapeutic potential of chimeric amyloid-reactive monoclonal antibody 11-1F4," *Clinical Cancer Research: An Official Journal of the American Association for Cancer Research*, vol. 9, No. 10, Pt 2, pp. 3831S-3838S (2003).

Hoshii, et al., "Immunohistochemical study of immunoglobulin light chain amyloidosis with antibodies to the immunoglobulin light chain variable region," *Pathology International*, vol. 56, No. 6, pp. 324-330 (2006).

James, et al., "Beta-edge interactions in a pentadecameric human antibody V kappa domain," *Journal of Molecular Biology*, vol. 367, No. 3, pp. 603-608 (2007).

Graille, et al., "Evidence for plasticity and structural mimicry at the immunoglobulin light chain-protein L interface," *The Journal of Biological Chemistry*, vol. 277, No. 49, pp. 47500-47506 (2002).

Housden, et al., "Immunoglobulin-binding domains: Protein L from *Peptostreptococcus magnus*," *Biochemical Society Transactions*, vol. 31, No. 3, pp. 716-718 (2003).

Ramirez-Alvarado, et al., "Does the Location of a Mutation Determine the Ability to Form Amyloid Fibrils?," *Journal of Molecular Biology*, vol. 323, No. 1, pp. 17-22 (2002).

Munoz, et al., "A small domain (6.5 kDa) of bacterial protein G inhibits C3 covalent binding to the Fc region of IgG immune complexes," *European Journal of Immunology*, vol. 28, No. 8, pp. 2591-2597 (1998).

Abraham, R. S., et al., Blood 101, 3801-3808 (2003).
Asl, K. H., et al., Amyloid 11, 179-183 (2004).
Becker & Guarente, Methods Enzymol. 194:187 (1990).
Bjorck & Kronvall, J. Immunol., 133:969 (1984).
Bjorck, et al., J. Immunol., 140(6):1994-1998 (1988).
Boerner, et al., J. Immunol. 147:86-95 (1991).
Calarese, et al., Science, vol. 300, pp. 2065-2074 (2003).
CCP4. (1994) Acta. Cryst. D50, 760-763.
Chien, P., et al., Nature, vol. 424, No. 6951, pp. 948-951 (2003).
Chiti, F., et al., Nature, vol. 424, No. 6950, pp. 805-808 (2003).
Clackson, T. & Wells, J. A., Science, 267, 383-386 (1995).
Cole, et al., Mol. Cell. Biol., 62:109-120 (1984).
Cote, et al., PNAS, 80(7):2026-2030 (1983).
Delano, W. L., et al., Science, 287, 1279-1283 (2000).
Denoroy, L., et al., Immunol. Lett. 42, 63-66 (1994).
Deret, S., et al., Protein Eng., 10, 1191-1197 (1997).
Derrick, J. P. & Wigley D. B., Journal of Molecular Biology, vol. 243(5):906-918 (1994).
Derrick, J. P. & Wigley D. B., Nature, vol. 359, pp. 752-754 (1992).
Doyle, et al., Int. J. Pept. Protein Res., 47(6)427-436 (1996).
Falk, et al., N Engl. J. Med., 337(13):898-909 (1997).
Forsgren & Sjoquist, J. Immunol., 97:822 (1966).
Genovese, A., et al., Infect. Immun., vol. 68, No. 10, pp. 5517-5524 (2000).
Gietz & Woods, Biotechniques, 30:816-228 (2001).
Graille, M., et al., J. Biol. Chem., 277, 47500-47506 (2002).
Graille, M., et al., Structure (Camb) 9, No. 8, 679-687 (2001).
Guss, B., et al., Embo J., 5:1567-1575 (1987).
Hawkins, P. N., et al., N. Engl. J. Med. vol. 323, No. 8, 508-513 (1990).
Hoogenboom & Winter, J. Mol. Biol. 227(2):381 (1991).
Hurle, et al., PNAS, 91(12):5446-5450 (1994).
Ivanova, M. L, et al., Proc Natl Acad Sci USA, vol. 101, No. 29, pp. 10584-10589 (2004).
Jager, M. & Pluckthun, A., FEBS Lett, 418, 106-110 (1997).
Jin, L. W., et al., Proc Natl Acad Sci U S A im, 15294-15298 (2003).
Jones, et al., Nature, 321(6069):522-525 (1986).
Kabat, et al., Seq of Protein of Immunol. Interest. (1991).
Kastern, W., et al., J. Biol. Chem 267(18), 12820-12825 (1992).
Khamlichi, A. A., et al., Blood, 86, 3655-3659 (1995).
Kohler, et al., Nature, 256:4950497 (1975).
Kozbor, et al., J. Immunol. Meth., 81:31-42 (1985).
Krebs, M. R., Proc Natl Acad Sci USA, vol. 101, No. 40, pp. 14420-14424 (2004).
Lin, et al., Amyloid, 8:182-193 (2001).
Luchansky, et al., Mol. Microbiol., 2(5):637-646 (1988).
Makin, O. S., et al., PNAS USA, 1Q2, 315-320 (2005).
Mark, et al., J. Mol. Biol., 222:581 (1991).
Meziere, et al., J. Immunol., 159(7):3230-3237 (1997).
Moyle, W. R., et al., Mol. Immunol., vol. 20, No. 4, pp. 439-452 (1983).
Myers, J. K., et al., Protein Sci., vol. 4, No. 10, pp. 2138-2148 (1995).
Nelson, R., et al., Nature, vol. 435, No. 7043, pp. 773-778 (2005).
Nilsson, et al., Eur. J. Biochem., 224:103-108 (1994).
Nord, et al., Protein Engineering, 8:601-608 (1995).
Nowak, M., Proteins 55, 11-21 (2004).
Nowakowski, A., et al., Proc Natl Acad Sci USA 99, 11346-50 (2002).
Nygren, et al., J. Mol. Reconit., 1(2):69-74 (1988).
Olsson, A., et al., Eur. J. Biochem., 168:319-324 (1987).
Orlandi, et al., PNAS, 86(10):3833-3837 (1989).
Patella, V., et al., J. Immunol., 145, 3054-3061 (1990).
Pepys, M. B., et al., Amyloid: Int. J. Exp. Clin. Invest 4, 274-295 (1997).
Presta, et al., Curr. Op. Struct. Biol. 2(4):593-596 (1992).
Raffen, R., et al., Protein Sci 8(3):509-17 (1999).
Reches, M., et al., J. Biol. Chem., vol. 277, No. 38, pp. 35475-35480 (2002).
Reis, et al., J. Immunol., 132(6):3091-3097 (1984).
Richardson, J. S., et al., Proc Natl Acad Sci USA 99, 2754-2759 (2002).
Riechmann, et al., Nature, 332(6162):323-329 (1988).
Schormann, N., et al., Proc Natl Acad Sci USA, vol. 92, No. 21, pp. 9490-9494 (1995).
Sereg, J. A., et al., Nat. Struct. Biol., vol. 9, No. 10, pp. 734-739 (2002).
Serpell, L. C, et al., J. Mol. Biol., vol. 300, No. 5, pp. 1033-1039 (2000).
Souillac, P. O., et al., Biochemistry 42(26):8094-8104 (2003).
Spada, S., et al., J. Mol. Biol., vol. 283, No. 2, pp. 395-407 (1998).
Stevens, et al., Amyloid, 7, 200-211 (2000).
Storoni, L. C, et al., Acta Crystallogr D Biol Crystallogr 60(3):432-438 (2004).
Tennent, G. A., et al., PNAS USA, vol. 92, No. 10, pp. 4299-4303 (1995).
Thompson, et al., Nuc. Acid.Res., 22(22):4673-4680 1994).
Thorsett, et al., Biochem. Biophys. Res. Comm., 111(1):166 (1983).
Van Den Beuken, et al., J. Mol. Biol., 310:591-601 (2001).
Veber, et al., PNAS, 75(6):2636 (1978).
Winter, et al., Nature, 349(6307):293-299 (1991).
Zhou, A., et al., J. Mol. Biol., vol. 342, No. 3, pp. 931-941 (2004).
Zurdo J, G. J., et al., J. Mol. Biol., vol. 311, No. 2, pp. 325-340 (2001).
Abraham, et al., Blood, 101:10, 3802-3808, May 15, 2003.
Aggarwal, et al., J. Biol. Chem., 278:3, 1910-1914, Jan. 17, 2003.
Alderson, et al., Cytokine, 6:4, 407-413, Jul. 1994.
Asadullah, et al., Exp. Dermatol., 9:248-251, 2000.
Asl, et al., Amyloid, 11:179-183, 2004.
Becker, et al., Meth in Enzymol. 194, 182-187, 1991.
Bjorck, et al., J. Immunol., 133:969, 1984.

Bjorck, et al., J. Immunol., 140:1994, 1988.
Boerner, et al., J. Immunol., 147:1, 86-95, Jul. 1, 1991.
Borset, et al., Eur. J. Haematology, 53, 31-37, 1994.
Brach, et al., Cancer Research, 52, 2197-2201, Apr. 15, 1992.
Burchill, et al., Infect. Immunity, 71(6):3437, 2003.
Clarese, et al., Science, vol. 300, 2065-2071, Jun. 27, 2003.
CCP4 Acta Cryst. D50, 760-763, 1994.
Chegini, et al., Am. J. Rep. Immunol., 49:75-83, 2003.
Chen, et al., J. Biol. Chem., 278:19, 17036-17043, May 9, 2003.
Cheng, et al., Am. J. Resp. Crit. Care Med., 166, 409-416, 2002.
Chien, et al., Nature, 424, 948-951, Aug. 21, 2003.
Chiti, et al., Nature, 424, 805-808, Aug. 14, 2003.
Clackson, et al., Science, 267, 383-386, Jan. 20, 1995.
Cole, et al., Mol. Cell. Biochemistry, 62:109-120, 1984.
Corre, et al., Exp. Hematol., 27:28-36, 1999.
Cote, et al., PNAS, 80:2026-2030, 1983.
Cua, et al., Nature, 421, 744-748, Feb. 13, 2003.
DeBlaker-Hohe, et al., Cell. Immunol., 165, 33-43, 1995.
DeLano, et al., Science, 287, 1279-1283, Feb. 18, 2000.
Dellinger, et al., Clin. Infec. Dis., 36, 1259-1265, May 15, 2003.
Denoroy, et al., Immunol. Lett. 42, 63-60, 1994.
Denning, J. Immunol., 156:4807-4814, 1996.
Deret, et al., Protein Engineering, 10(10):1191-1197, 1997.
Derrick & Wigley, J. Mol. Biol., 243:906-908, 1994.
Derrick & Wigley, Nature, 359:752-754, Oct. 22, 1992.
Doyle, et al., Int. J. Peptide Prot. Res., 47:427-436, 1996.
Eum, et al., J. Allergy Clin. Immunol., 111(5):1049-1061, May 2003.
Falk, et al., N. Eng. J. Med., 337:898-909, 1997.
Ferrettie, et al., J. Immunol., 170:2106-2112, 2003.
Forsgren, et al., J. Immunol., 97:822, 1966.
Fukao, et al., J. Immunol., 164:64-71, 2000.
Garn, et al., Immunobiol., 205:321-334, 2002.
Genvese, et al., Infection & Immunity, 68(10)5517-5524, Oct. 2000.
Gietz, et al., BioTechniques, 30:816-831, Apr. 2001.
Gounni, et al., Blodd, 96(6):3163-2171, Sep. 15, 2000.
Graille, M., et al., Structure 9, 679-687, 2001.
Graille, M., et al., J. Biol. Chem., 277, 47500-47506, 2002.
Gregoray, et al., J. Immunol., 170:5359-5366, 2003.
Guss, B., et al., EMBO J., 5:1567-1575, 1986.
Hahn, et al., J. Allergy Clin. Immunol., 111(6):1361-1369, Jun. 2003.
Halasz, et al., Allergy & Asthma Proc., 24(2):111-118, 2003.
Hawkins, et al., NEJM, 323(8)508-531, Aug. 23, 1990.
Hehner, et al., J. Immunol. 165:4319-4328, 2000.
Hellings, et al., Am. J. Respir. Cell Mol. Biol., 28:42-50, 2003.
Herbelin, et al., J. Immunol. 148(1):99-105, Jan. 1, 1992.
Hermouet, et al., Cytokine, 20(4):178-183, Nov. 24, 2002.
Honorati, et al., Osteoarthirtis & Cartilage, 10:799-807, 2002.
Hoogenboom & Winter, J. Mol. Biol. 227:381-388, Jun. 24, 1992.
Howells, et al., Eur. J. Immunol., 21:97-101, 1991.
Hurle, et al., PNAS, 91:5446-5450, 1994.
Hurst, et al., J. Immunol., 169:443-453, 2002.
Ikeda, et al., Blood, 101:3594-3596, 2003.
Itoh, et al., Cell. Immunol. 157:478-488, 1994.
Ivanova, et al., PNAS, 101(29):10587-10589, Jul. 20, 2004.
Jager, et al., FEBS Lett., 418:106-110, 1997.
Jin, et al., PNAS, 100(26):15294-15298, Dec. 23, 2003.
Jones, et al., Am. J. Resp. Cell Mol. Biol., 26:748-753, 2002.
Jones, et al., Nature, 321:522-525, May 29, 1986.
Joosten, et al., Athritis & Rheumatism, 48(2):339-347, Feb. 2003.
Jutel, et al., Eur. J. Immunol. 33:1205-1214, 2003.
Kabat, et al., Ann. NYAS, 382-393, 1991.
Kaneda, et al., J. Inter. & Cyto. Res. 23:155-152, 2003.
Kastern, et al., J. Biol. Chem., 267, 12820-12825, 1992.
Kastern, et al., Infection & Immunity, 58(5):1217-1222, May 1990.
Kauffmann, et al., Rheumatology, 40:474-475, 2001.
Keates, et al., Gastroenterology, 199:972-982, 2000.
Kelly-Welch, et al., Science, 300:1527, 2003.
Khamlichi, et al., Blood, 86(10):3655-3659, Nov. 15, 1995.
Kohler, et al., Nature, 256, Aug. 7, 1975.
Kozbor, et al., J. Immunol. Meth., 81:31-42, 1985.
Krebs, et al., PNAS, 101(40):14420-14424, Oct. 5, 2001.
Kudo, et al., Bone, 32:1-7, 2003.
Kupperman, et al., Nature Medicine, 8(8):885-889, Aug. 2002.

Laan, et al., Eur. Resp. J., 21:387-393, 2003.
Lankford, et al., J. Leuk. Biol., 73:49-56, Jan. 2003.
Lauwerys, et al., Cytokine, 11(11):822-830, Nov. 1999.
Lauwerys, et al., Eur. J. Immunol. 28:2017-2024, 1998.
Lazenby, et al., Cytokine, 4(6):479-487, Nov. 1992.
LeGrand, et al., Arthritis & Rheumatism, 44(9):2078-2083, Sep. 2001.
Liao, et al., J. Immunol. 169:4288-4297, 2002.
Li, et al., Nature Med., 7(1):114-118, Jan. 2001.
Little, et al., Am. J. resp. Cell Mol. Biol., 28:354-362, 2003.
Loong, et al., J. Path. 197:322-332, Apr. 16, 2002.
Lorentz, et al., Immunol. Rev., 179:57-60, 2001.
Lubberts, et al., J. Immunol. 170:2655-2662, 2003.
Luchansky, et al., Mol. Microbiol., 2(5):637-646, 1988.
Makin, et al., PNAS, 102(2):315-320, Jan. 11, 2005.
Marks, et al., J. Mol. Biol. 222:581-597, 1991.
Mathy, et al., Immunology, 100:63-69, 2000.
Matsumoto, et al., Cytokine, 6(5):455-461, Sep. 1994.
Mehrotra, et al., J. Immunol., 154:5093-5102, 1995.
Meziere, et al., J. Immunol. 159:3230-3237, 1997.
Moriwaki, et al., Metabolism, 52(5):605-608, May 2003.
Moyle, et al., Mol. Immunol. 20(4):439-452, 1983.
Myers, et al., Protein Science, 4:2138-2148, 1995.
Mysliwiec, et al., Intl. Immunopharma., 3:549-552, 2003.
Nelson, et al., Nature, 435:773-778, Jun. 9, 2005.
Nielsen, et al., Scan. J. Gastro., 2:180-185, 2003.
Nilsson, et al., Eur. J. Biochem., 224:103-108, 1994.
Nord, K., et al., Preotein Eng., 8:601-608, 1995.
Nowak, Proteins, 55:11-21, 2004.
Nowakowski, et al., PNAS, 99(17):11346-11350:Aug. 20, 2002.
Nygren, et al., J. Mol. Recognit. 1:69-74, 1988.
Okamoto, et al., Blood, 99:1289-1298, 2002.
Olsson, et al., Eur. J. Biochem., 168:319-324, 1987.
Orlandi, et al., PNAS, 86:3833-3837, May 1989.
Parada, et al., J. immunol. 160:2115-2120, 1998.
Patella, et al., J. immunol. 145(9):3054-3061, Nov. 1, 1990.
Pepys, et al., Amyloid, 4:274-295, 1997.
Pflanz, et al., Immunity, 16:779-790, Jun. 2002.
Presta, et al., Curr. Opin. Struct. Biol. 2:593-596, 1992.
Qin, et al., Blood, 98:2778-2783, 2001.
Raffen, et al., Prot. Sci. 8:509-517, 1999.
Ragab, et al., Am. J. Ohysiol. Cell Biol. 283:C679-C687, 2002.
Reches, et al., J. Biol. Chem. 277(38):35475-35480, Sep. 20, 2002.
Reis, et al., Immunol., 132:3091, 1984.
Rich, et al., Curr. Biol., 11:R531-R534, 2001.
Richardson, et al., PNAS, 99:2754-2759, 2002.
Riechmann, et al., Nature, 332(24):323-327, Mar. 1988.
Salmaggi, et al., J. Neuro-Oncol. 62:297-303, 2003.
Schrmann, et al., PNAS, 92:9490-9494, 1995.
Sereg, et al., Nature Struct. Biol., 9(10):734-739, Oct. 2002.
Serpell, et al., J. Mol. Biol. 300:1033-1039, 2000.
Siepen, et al., Protein Sci., 12:2348-2359, 2003.
Souillac, et al., Biochemistry, 42, 8094-8104, 2003.
Spada, et al., J. Mol. Biol., 283:395-407, 1998.
Spadaro, et al., Clin. Rheumatol., 22:107-111, 2003.
Stevens, Amyloid, 7:200-211, 2000.
Storoni, et al., ACTA Cryst., 432-438, 2004.
Strengell, et al., J. Immunol., 170:5464-5469, 2003.
Tain, et al., Cytokine, 21:155-159, 2003.
Temann, et al., J. Clin. Invest., 109:29-39, 2002.
Tennent, PNAS, 92:4299-4303, May 1995.
Terada, et al., Clin. Exp. Allergy, 30:348-355, 2000.
Thomas & Heywood, Thorax, 57:774-778, 2002.
Thompson, et al., Nuc. Acids Res., 22(22):4673-4680, 1994.
Thursell, et al.,m Bichem. Biophys. Res. Comm., 111:166, 1983.
Toda, et al., J. Aller. Clin. Immunol., 111(4):875-881, 2003.
van Bezooijen, et al., Ann. Rheum. Dis. 61:870-876, 2002.
Van den Beucken, et al., J. Mol. Biol. 310:591-601, 2001.
Veber, et al., PNAS, 75(6):2636-2640, 1978.
Wiley & Sons, Curr. Proto. Mol. Biol., Suppl. 13, 1989.
Winter & Milstein, Nature, 349:293-299, Jan. 24, 1991.
Yoshida, et al., Cell Immunol., 207:75-80, 2001.
Zhang, et al., J. Exp. Med. 182:699-709, Sep. 1995.

Zhou, et al., J. Mol. Biol., 342:931-941, 2004.
Zurdo, et al., J. Mol. Biol. 311:325-340, 2001.
Sambrook & Russell, Molecular Cloning: a Laboratory Manual, 3rd Edition, 2001.
D.H. Rich Protease Inhibitors, 1986.
Solid-Phase Peptied Synthesis, 1997.

Remington: The Science & Practice of Pharmacy, 19$^{th}$ Edition, 1995.
Monoclonal Antibodies, A manual of techniques, 1988.
Monoclonal Hybridoma Antibodies, Techniques & Applications, 1982.
Harlow & Lane, Antibodies: A laboratory Manual, 1988.

* cited by examiner

Figure 7

SSLS (SEQ ID NO: 1)

PSSLSA ((SEQ ID NO: 2)

QTAEF (SEQ ID NO: 3)

QTATF (SEQ ID NO: 4)

TLKGETT (SEQ ID NO: 5)

SEQ ID NO:6:

```
  1  EFNKYGVSDY YKNLINNAKT VEGVKDLQAQ VVESAKKARI SEATDGLSDF LKSQTPAEDT
 61  VKSIELAEAK VLANRELDKY GVSDYHKNLI NNAKTVEGVK DLQAQVVESA KKARISEATD
121  GLSDFLKSQT PAEDTVKSIE LAEAKVLANR ELDKYGVSDY YKNLINNAKT VEGVKALIDE
181  ILAALPKTDT YKLILNGKTL KGETTTEAVD AATAEKVFKQ YANDNGVDGE WTYDDATKTF
241  TVTEKPEVID ASELTPAVTT YKLVINGKTL KGETTTEAVD AATAEKVFKQ YANDNGVDGE
301  WTYDDATKTF TVTEKPEVID ASELTPAVTT YKLVINGKTL KGETTTKAVD AETAEKAFKQ
361  YANDNGVDGV WTYDDATKTF TVTEMVTEVP GDAPTEPEKP EASIPLVPLT PATPIAKDDA
421  KKDDTKKEDA KKPEAKKEDA KKAETLPTTG EGSNPFFTAA ALAVMAGAGA LAVASKRKED
```

DOM 16-39-618 (S12P) (SEQ ID NO: 7):

<400> 621

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Trp Ile Gly Asn Leu
            20                  25                  30

Leu Asp Trp Tyr Gln Gln Lys Pro Gly Lys Ala Pro Lys Leu Leu Ile
        35                  40              45

Tyr Tyr Ala Ser Phe Leu Gln Ser Gly Val Pro Ser Arg Phe Ser Gly
    50                  55              60

Ser Gly Phe Gly Thr Asp Phe Thr Leu Thr Ile Ser Ser Leu Gln Pro
65                  70              75              80

Glu Asp Phe Ala Thr Tyr Tyr Cys Gln Gln Ala Asn Pro Val Pro Pro
                85              90              95

Thr Phe Gly Gln Gly Thr Lys Val Glu Ile Lys Arg
                100             105

Figure 7a

DOM 7h-14 (SEQ ID NO: 8):

GACATCCAGATGACCCAGTCTCCATCCTCCCTGTCTGCATCTGTAGGAGACCGTGTCACC
ATCACTTGCCGGGCAAGTCAGTGGATTGGGTCTCAGTTATCTTGGTACCAGCAGAAACCA
GGGAAAGCCCCTAAGCTCCTGATCATGTGGCGTTCCTCGTTGCAAAGTGGGGTCCCATCA
CGTTTCAGTGGCAGTGGATCTGGGACAGATTTCACTCTCACCATCAGCAGTCTGCAACCT
GAAGATTTTGCTACGTACTACTGTGCTCAGGGTGCGGCGTTGCCTAGGACGTTCGGCCAA
GGGACCAAGGTGGAAATCAAACGG

DOM 7r-16 (SEQ ID NO: 9):

Asp Ile Gln Met Thr Gln Ser Pro Ser Ser Leu Ser Ala Ser Val Gly
 1           5            10           15

Asp Arg Val Thr Ile Thr Cys Arg Ala Ser Gln Lys Ile Tyr Lys Asn
        20           25           30

Leu Arg Trp Tyr Gln Gln Lys Pro Gly Lys Ala Pro Lys Leu Leu Ile
       35           40           45

Tyr Asn Ser Ser Ile Leu Gln Ser Gly Val Pro Ser Arg Phe Ser Gly
      50           55           60

Ser Gly Ser Gly Thr Asp Phe Thr Leu Thr Ile Ser Ser Leu Gln Pro
 65           70           75           80

Glu Asp Phe Ala Thr Tyr Tyr Cys Gln Gln Arg Tyr Leu Ser Pro Tyr
         85           90           95

Thr Phe Gly Gln Gly Thr Lys Val Glu Ile Lys Arg
        100          105

Figure7b

PEP1-5-19(S12P)-TVA-DOM7h-8 (SEQ ID NO: 10):

GACATCCAGATGACCCAGTCTCCATCCTCTCTGcccGCATCTGTAGGAGACCGTG
TCACCATCACTTGCCGGGCAAGTCAGAGCATTGATAGTTATTTACATTGGTACCA
GCAGAAACCAGGGAAAGCCCCTAAGCTCCTGATCTATAGTGCATCCGAGTTGCA
AAGTGGGGTCCCATCACGTTTCAGTGGCAGTGGATCTGGGACAGATTTCACTCT
CACCATCAGCAGTCTGCAACCTGAAGATTTTGCTACGTACTACTGTCAACAGGTT
GTGTGGCGTCCTTTTACGTTCGGCCAAGGGACCAAGGTGGAAATCAAACGGACC
GTCGCTGATATTCAAATGACCCAATCCCCTTCCTCCCTGAGCGCTTCCGTGGGTG
ACCGTGTTACTATTACCTGTCGTGCTTCCCAATCCATCTCTTCTTACCTGAACTGG
TACCAACAAAAGCCGGGCAAAGCACCGAAACTGCTGATCTATCGCAACAGCCCG
CTGCAGAGCGGCGTACCTAGCCGCTTTAGCGGTAGCGGTTCCGGTACGGACTTT
ACCCTGACTATTAGCTCCCTGCAGCCAGAAGATTTTGCAACGTACTATTGCCAGC
AGACCTACCGTGTGCCGCCAACGTTTGGCCAGGGTACCAAAGTGGAAATCAAAC
GC Primer 1294 (SEQ ID NO: 11):

CACGCGTCGACGgatattcagatgactcagagcccaagcagcctgcccgcgtccgtcggtgat

TVA linker (SEQ ID NO: 12):

ACCGTCGCTGCTCCA

DOM4-130-54(S12P)-TVAAPS-DOM7h-8 (SEQ ID NO: 13):

GACATCCAGATGACCCAGTCTCCATCCTCCCTGcccGCATCTGTAGGAGACCGTG
TCACCATCACTTGCCGGGCAAGTCAGGATATTTACCTGAATTTAGACTGGTATCA
GCAGAAACCAGGGAAAGCCCCTAAGCTCCTGATCAATTTTGGTTCCGAGTTGCA
AAGTGGTGTCCCATCACGTTTCAGTGGCAGTGGATATGGGACAGATTTCACTCTC
ACCATCAGCAGTCTGCAACCTGAAGATTTCGCTACGTACTACTGTCAACCGTCTT
TTTACTTCCCTTATACGTTCGGCCAAGGGACCAAGGTGGAAATCAAACGGACCGT
CGCTGCTCCAGATATTCAAATGACCCAATCCCCTTCCTCCCTGAGCGCTTCCGTG
GGTGACCGTGTTACTATTACCTGTCGTGCTTCCCAATCCATCTCTTCTTACCTGAA
CTGGTACCAACAAAAGCCGGGCAAAGCACCGAAACTGCTGATCTATCGCAACAG
CCCGCTGCAGAGCGGCGTACCTAGCCGCTTTAGCGGTAGCGGTTCCGGTACGG
ACTTTACCCTGACTATTAGCTCCCTGCAGCCAGAAGATTTTGCAACGTACTATTG
CCAGCAGACCTACCGTGTGCCGCCAACGTTTGGCCAGGGTACCAAAGTGGAAAT
CAAACGC

Figure 7c

DOM4-130-54(S12P)-TVAAPS-DOM7h-2 (SEQ ID NO: 14):

GACATCCAGATGACCCAGTCTCCATCCTCCCTGcccGCATCTGTAGGAGACCGTG
TCACCATCACTTGCCGGGCAAGTCAGGATATTTACCTGAATTTAGACTGGTATCA
GCAGAAACCAGGGAAAGCCCCTAAGCTCCTGATCAATTTTGGTTCCGAGTTGCA
AAGTGGTGTCCCATCACGTTTCAGTGGCAGTGGATATGGGACAGATTTCACTCTC
ACCATCAGCAGTCTGCAACCTGAAGATTTCGCTACGTACTACTGTCAACCGTCTT
TTTACTTCCCTTATACGTTCGGCCAAGGGACCAAGGTGGAAATCAAACGGACCGT
CGCTGCTCCAGACATCCAGATGACCCAGTCTCCATCCTCCCTGTCTGCATCTGTA
GGAGACCGTGTCACCATCACTTGCCGGGCAAGTCAGAAGATTGCTACTTATTTAA
ATTGGTATCAGCAGAAACCAGGGAAAGCCCCTAAGCTCCTGATCTATAGGTCTTC
CTCTTTGCAAAGCGCGGTCCCATCACGTTTCAGTGGCAGTGGATCTGGGACAGT
TTTCACACTCACCATCAGCAGTCTGCAACCTGAAGATTTTGCTACGTACTACTGTC
AACAGACGTATGCTGTTCCTCCTACGTTCGGCCAAGGGACCAAGGTGGAAATCA
AACGG DOM4-130-54(S12P)-TVAAPS-DOM7h-10 (SEQ ID NO: 15):

GACATCCAGATGACCCAGTCTCCATCCTCCCTGcccGCATCTGTAGGAGACCGTG

TCACCATCACTTGCCGGGCAAGTCAGGATATTTACCTGAATTTAGACTGGTATCA

GCAGAAACCAGGGAAAGCCCCTAAGCTCCTGATCAATTTTGGTTCCGAGTTGCA

AAGTGGTGTCCCATCACGTTTCAGTGGCAGTGGATATGGGACAGATTTCACTCTC

ACCATCAGCAGTCTGCAACCTGAAGATTTCGCTACGTACTACTGTCAACCGTCTT

TTTACTTCCCTTATACGTTCGGCCAAGGGACCAAGGTGGAAATCAAACGGACCGT

CGCTGCTCCAGACATCCAGATGACCCAGTCTCCACCCTCCCTGTCCGCATCTGTA

GGAGACCGTGTCACCATCACTTGCCGGGCAAGTCAGAGCATTAGCAGCTATTTA

AATTGGTATCAGCAGAAACCAGGGAAAGCCCCTAAGCTCCTGATCTATCGGAATT

CCCCTTTGCAAAGTGGGGTCCCATCACGGTTCAGTGGCAGTGGATCTGGGACAG

ATTTCACTCTCACCATCAGCAGTCTGCAACCTGAAGATTTTGCTACGTACTACTGT

CAACAGACTTATTCGATTCCTCCTACGTTCGGCCAAGGGACCAAGGTGGAAATCA

AACGG

Figure 7d

DOM4-130-93(S12P)-TVAAPS-DOM7h-8 (SEQ ID NO: 16):

GACATCCAGATGACCCAGTCTCCATCCTCCCTGCCTGCATCTGTAGGAGACCGT
GTCACCATCACTTGCCGGGCAAGTCAGGATATTTACCTGAATTTAGACTGGTATC
AGCAGAAACCAGGGAAAGCCCCTAAGCTCCTGATCAATTTTGGTTCCGAGTTGC
AAAAGGGTGTCCCATCACGTTTCAGTGGCAGTGGATATGGGACAGATTTCACTCT
CACCATCAGCAGTCTGCAACCTGAAGATTTCGCTACGTACTACTGTCAACCGTCT
TTTTACTTCCCTTATACGTTCGGCCAAGGGACCAAGGTGGAAATCAAACGGACCG
TCGCTGATATTCAAATGACCCAATCCCCTTCCTCCCTGAGCGCTTCCGTGGGTGA
CCGTGTTACTATTACCTGTCGTGCTTCCCAATCCATCTCTTCTTACCTGAACTGGT
ACCAACAAAAGCCGGGCAAAGCACCGAAACTGCTGATCTATCGCAACAGCCCGC
TGCAGAGCGGCGTACCTAGCCGCTTTAGCGGTAGCGGTTCCGGTACGGACTTTA
CCCTGACTATTAGCTCCCTGCAGCCAGAAGATTTTGCAACGTACTATTG

DOM4-130-54(S12P)-TVAAPS-DOM7h-22 (SEQ ID NO: 17):

GACATCCAGATGACCCAGTCTCCATCCTCCCTGCCCGCATCTGTAGGAGACCGT
GTCACCATCACTTGCCGGGCAAGTCAGGATATTTACCTGAATTTAGACTGGTATC
AGCAGAAACCAGGGAAAGCCCCTAAGCTCCTGATCAATTTTGGTTCCGAGTTGC
AAAGTGGTGTCCCATCACGTTTCAGTGGCAGTGGATATGGGACAGATTTCACTCT
CACCATCAGCAGTCTGCAACCTGAAGATTTCGCTACGTACTACTGTCAACCGTCT
TTTTACTTCCCTTATACGTTCGGCCAAGGGACCAAGGTGGAAATCAAACGGACCG
TCGCTGCTCCAGAGGTGCAGCTGTTGGAGTCTGGGGGAGGCTTGGTACAGCCT
GGGGGGTCCCTGCGTCTCTCCTGTGCAGCCTCCGGATTCACCTTTTCGAAGTATT
GGATGTCGTGGGTCCGCCAGGCTCCAGGGAAGGGTCTAGAGTGGGTCTCATCT
ATTGATTTTATGGGTCCGCATACATACTACGCAGACTCCGTGAAGGGCCGGTTCA
CCATCTCCCGCGACAATTCCAAGAACACGCTGTATCTGCAAATGAACAGCCTGCG
TGCCGAGGATACCGCGGTATATTACTGTGCGAAAGGGAGGACGTCGATGTTGCC
GATGAAGGGGAAGTTTGACTACTGGGGTCAGGGAACCCTGGTCACCGTCTCGA
GC

DOM4-130-54(S12P)-TVAAPS-DOM7R-31 (SEQ ID NO: 18):

GACATCCAGATGACCCAGTCTCCATCCTCCCTGCCCGCATCTGTAGGAGACCGT
GTCACCATCACTTGCCGGGCAAGTCAGGATATTTACCTGAATTTAGACTGGTATC
AGCAGAAACCAGGGAAAGCCCCTAAGCTCCTGATCAATTTTGGTTCCGAGTTGC
AAAGTGGTGTCCCATCACGTTTCAGTGGCAGTGGATATGGGACAGATTTCACTCT
CACCATCAGCAGTCTGCAACCTGAAGATTTCGCTACGTACTACTGTCAACCGTCT
TTTTACTTCCCTTATACGTTCGGCCAAGGGACCAAGGTGGAAATCAAACGGACCG
TCGCTGCTCCAGAGGTGCAGCTGTTGGAGTCTGGGGGAGGCTTGGTACAGCCT
GGGGGGTCCCTGCGTCTCTCCTGTACAGCCTCCGGATTCACCTTTAGGCATTATC
GTATGGGTTGGGTCCGCCAGGCTCCAGGGAAGGGTCTAGAGTGGGTCTCATGG
ATTCGTCCGGATGGTACGTTTACATACTACGCAGACTCCGTGAAGGGCCGGTTC
ACCATCTCCCGCGACAATTCCAAGAACACGCTGTATCTGCAAATGAACAGCCTGC
GTGCCGAGGACACCGCGGTATATTACTGTGCGAAATCTTATATGGGTGATAGGT
TTGACTACTGGGGTCAGGGAACCCTGGTCACCGTCTCGAGCG

SEQUENCE LISTING

```
<160> NUMBER OF SEQ ID NOS: 28

<210> SEQ ID NO 1
<211> LENGTH: 4
<212> TYPE: PRT
<213> ORGANISM: Artificial Sequence
<220> FEATURE:
<223> OTHER INFORMATION: Amino acid sequence from FR1 region of an
      immunoglobulin light chain variable domain.
<220> FEATURE:
<223> OTHER INFORMATION: An anti-EGFR dAb.

<400> SEQUENCE: 1

Ser Ser Leu Ser
 1

<210> SEQ ID NO 2
<211> LENGTH: 6
<212> TYPE: PRT
<213> ORGANISM: Artificial Sequence
<220> FEATURE:
<223> OTHER INFORMATION: Amino acid sequence from FR1 region of an
      immunoglobulin light chain variable domain.

<400> SEQUENCE: 2

Pro Ser Ser Leu Ser Ala
 1               5

<210> SEQ ID NO 3
<211> LENGTH: 5
<212> TYPE: PRT
<213> ORGANISM: Artificial Sequence
<220> FEATURE:
<223> OTHER INFORMATION: Amino acid sequence from interacting strand of
      a protein L domain with a VK1 from a structural
      complex of an isolated domain with Fab2A2.
```

-continued

```
<400> SEQUENCE: 3

Gln Thr Ala Glu Phe
1               5

<210> SEQ ID NO 4
<211> LENGTH: 5
<212> TYPE: PRT
<213> ORGANISM: Artificial Sequence
<220> FEATURE:
<223> OTHER INFORMATION: amino acid sequence from 5th domain of protein
      L.

<400> SEQUENCE: 4

Gln Thr Ala Thr Phe
1               5

<210> SEQ ID NO 5
<211> LENGTH: 7
<212> TYPE: PRT
<213> ORGANISM: Artificial Sequence
<220> FEATURE:
<223> OTHER INFORMATION: amino acid sequence from beta-2 strand of SpG
      protein.

<400> SEQUENCE: 5

Thr Leu Lys Gly Glu Thr Thr
1               5

<210> SEQ ID NO 6
<211> LENGTH: 480
<212> TYPE: PRT
<213> ORGANISM: Artificial Sequence
<220> FEATURE:
<223> OTHER INFORMATION: Conserved amino acid sequence of each B-domain
      involved in IgG binding of SpG protein.

<400> SEQUENCE: 6

Glu Phe Asn Lys Tyr Gly Val Ser Asp Tyr Tyr Lys Asn Leu Ile Asn
1               5                   10                  15

Asn Ala Lys Thr Val Glu Gly Val Lys Asp Leu Gln Ala Gln Val Val
            20                  25                  30

Glu Ser Ala Lys Lys Ala Arg Ile Ser Glu Ala Thr Asp Gly Leu Ser
        35                  40                  45

Asp Phe Leu Lys Ser Gln Thr Pro Ala Glu Asp Thr Val Lys Ser Ile
    50                  55                  60

Glu Leu Ala Glu Ala Lys Val Leu Ala Asn Arg Glu Leu Asp Lys Tyr
65                  70                  75                  80

Gly Val Ser Asp Tyr His Lys Asn Leu Ile Asn Asn Ala Lys Thr Val
                85                  90                  95

Glu Gly Val Lys Asp Leu Gln Ala Gln Val Val Glu Ser Ala Lys Lys
            100                 105                 110

Ala Arg Ile Ser Glu Ala Thr Asp Gly Leu Ser Asp Phe Leu Lys Ser
        115                 120                 125

Gln Thr Pro Ala Glu Asp Thr Val Lys Ser Ile Glu Leu Ala Glu Ala
    130                 135                 140

Lys Val Leu Ala Asn Arg Glu Leu Asp Lys Tyr Gly Val Ser Asp Tyr
145                 150                 155                 160

Tyr Lys Asn Leu Ile Asn Asn Ala Lys Thr Val Glu Gly Val Lys Ala
                165                 170                 175

Leu Ile Asp Glu Ile Leu Ala Ala Leu Pro Lys Thr Asp Thr Tyr Lys
            180                 185                 190
```

Leu Ile Leu Asn Gly Lys Thr Leu Lys Gly Glu Thr Thr Glu Ala
        195                 200                 205

Val Asp Ala Ala Thr Ala Glu Lys Val Phe Lys Gln Tyr Ala Asn Asp
210                 215                 220

Asn Gly Val Asp Gly Glu Trp Thr Tyr Asp Asp Ala Thr Lys Thr Phe
225                 230                 235                 240

Thr Val Thr Glu Lys Pro Glu Val Ile Asp Ala Ser Glu Leu Thr Pro
                245                 250                 255

Ala Val Thr Thr Tyr Lys Leu Val Ile Asn Gly Lys Thr Leu Lys Gly
            260                 265                 270

Glu Thr Thr Thr Glu Ala Val Asp Ala Ala Thr Ala Glu Lys Val Phe
        275                 280                 285

Lys Gln Tyr Ala Asn Asp Asn Gly Val Asp Gly Glu Trp Thr Tyr Asp
290                 295                 300

Asp Ala Thr Lys Thr Phe Thr Val Thr Glu Lys Pro Glu Val Ile Asp
305                 310                 315                 320

Ala Ser Glu Leu Thr Pro Ala Val Thr Thr Tyr Lys Leu Val Ile Asn
                325                 330                 335

Gly Lys Thr Leu Lys Gly Glu Thr Thr Thr Lys Ala Val Asp Ala Glu
            340                 345                 350

Thr Ala Glu Lys Ala Phe Lys Gln Tyr Ala Asn Asp Asn Gly Val Asp
        355                 360                 365

Gly Val Trp Thr Tyr Asp Asp Ala Thr Lys Thr Phe Thr Val Thr Glu
370                 375                 380

Met Val Thr Glu Val Pro Gly Asp Ala Pro Thr Glu Pro Glu Lys Pro
385                 390                 395                 400

Glu Ala Ser Ile Pro Leu Val Pro Leu Thr Pro Ala Thr Pro Ile Ala
                405                 410                 415

Lys Asp Asp Ala Lys Lys Asp Asp Thr Lys Lys Glu Asp Ala Lys Lys
            420                 425                 430

Pro Glu Ala Lys Lys Glu Asp Ala Lys Lys Ala Glu Thr Leu Pro Thr
        435                 440                 445

Thr Gly Glu Gly Ser Asn Pro Phe Phe Thr Ala Ala Ala Leu Ala Val
450                 455                 460

Met Ala Gly Ala Gly Ala Leu Ala Val Ala Ser Lys Arg Lys Glu Asp
465                 470                 475                 480

<210> SEQ ID NO 7
<211> LENGTH: 108
<212> TYPE: PRT
<213> ORGANISM: Artificial Sequence
<220> FEATURE:
<223> OTHER INFORMATION: An anti-EGFR dAb.

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Trp Ile Gly Asn Leu
            20                  25                  30

Leu Asp Trp Tyr Gln Gln Lys Pro Gly Lys Ala Pro Lys Leu Leu Ile
        35                  40                  45

Tyr Tyr Ala Ser Phe Leu Gln Ser Gly Val Pro Ser Arg Phe Ser Gly
    50                  55                  60

Ser Gly Phe Gly Thr Asp Phe Thr Leu Thr Ile Ser Ser Leu Gln Pro
65                  70                  75                  80

Glu Asp Phe Ala Thr Tyr Tyr Cys Gln Gln Ala Asn Pro Val Pro Pro

```
                    85                  90                  95
Thr Phe Gly Gln Gly Thr Lys Val Glu Ile Lys Arg
            100                 105

<210> SEQ ID NO 8
<211> LENGTH: 324
<212> TYPE: DNA
<213> ORGANISM: Artificial Sequence
<220> FEATURE:
<223> OTHER INFORMATION: An anti-serum albumin dAb.

<400> SEQUENCE: 8
gacatccaga tgacccagtc tccatcctcc ctgtctgcat ctgtaggaga ccgtgtcacc      60
atcacttgcc gggcaagtca gtggattggg tctcagttat cttggtacca gcagaaacca     120
gggaaagccc ctaagctcct gatcatgtgg cgttcctcgt tgcaaagtgg ggtcccatca     180
cgtttcagtg gcagtggatc tgggacagat ttcactctca ccatcagcag tctgcaacct     240
gaagattttg ctacgtacta ctgtgctcag ggtgcggcgt tgcctaggac gttcggccaa     300
gggaccaagg tggaaatcaa acgg                                            324

<210> SEQ ID NO 9
<211> LENGTH: 108
<212> TYPE: PRT
<213> ORGANISM: Artificial Sequence
<220> FEATURE:
<223> OTHER INFORMATION: An anti-serum albumin dAb.

<400> SEQUENCE: 9

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Lys Ile Tyr Lys Asn
            20                  25                  30

Leu Arg Trp Tyr Gln Gln Lys Pro Gly Lys Ala Pro Lys Leu Leu Ile
        35                  40                  45

Tyr Asn Ser Ser Ile Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Arg Tyr Leu Ser Pro Tyr
                85                  90                  95

Thr Phe Gly Gln Gly Thr Lys Val Glu Ile Lys Arg
            100                 105

<210> SEQ ID NO 10
<211> LENGTH: 657
<212> TYPE: DNA
<213> ORGANISM: Artificial Sequence
<220> FEATURE:
<223> OTHER INFORMATION: Anti-TNF alpha dAb fused via a linker to an
      anti-serum albumin dAb.

<400> SEQUENCE: 10
gacatccaga tgacccagtc tccatcctct ctgcccgcat ctgtaggaga ccgtgtcacc      60
atcacttgcc gggcaagtca gagcattgat agttatttac attggtacca gcagaaacca    120
gggaaagccc ctaagctcct gatctatagt gcatccgagt tgcaaagtgg ggtcccatca    180
cgtttcagtg gcagtggatc tgggacagat ttcactctca ccatcagcag tctgcaacct    240
gaagattttg ctacgtacta ctgtcaacag gttgtgtggc gtccttttac gttcggccaa    300
gggaccaagg tggaaatcaa acggaccgtc gctgatattc aaatgaccca atccccttcc    360
```

-continued

```
tccctgagcg cttccgtggg tgaccgtgtt actattacct gtcgtgcttc ccaatccatc    420
tcttcttacc tgaactggta ccaacaaaag ccgggcaaag caccgaaact gctgatctat    480
cgcaacagcc cgctgcagag cggcgtacct agccgcttta gcggtagcgg ttccggtacg    540
gactttaccc tgactattag ctccctgcag ccagaagatt ttgcaacgta ctattgccag    600
cagacctacc gtgtgccgcc aacgtttggc cagggtacca agtggaaat caaacgc       657
```

```
<210> SEQ ID NO 11
<211> LENGTH: 63
<212> TYPE: DNA
<213> ORGANISM: Artificial Sequence
<220> FEATURE:
<223> OTHER INFORMATION: Oligonucleotide primer.

<400> SEQUENCE: 11
cacgcgtcga cggatattca gatgactcag agcccaagca gcctgcccgc gtccgtcggt    60
gat                                                                  63
```

```
<210> SEQ ID NO 12
<211> LENGTH: 15
<212> TYPE: DNA
<213> ORGANISM: Artificial Sequence
<220> FEATURE:
<223> OTHER INFORMATION: Artificial linker sequence.

<400> SEQUENCE: 12
accgtcgctg ctcca                                                     15
```

```
<210> SEQ ID NO 13
<211> LENGTH: 663
<212> TYPE: DNA
<213> ORGANISM: Artificial Sequence
<220> FEATURE:
<223> OTHER INFORMATION: Anti IL-1 dAb fused by a linker to a anti-
      serum albumin dAb.

<400> SEQUENCE: 13
gacatccaga tgacccagtc tccatcctcc ctgcccgcat ctgtaggaga ccgtgtcacc    60
atcacttgcc gggcaagtca ggatatttac ctgaatttag actggtatca gcagaaacca   120
gggaaagccc ctaagctcct gatcaatttt ggttccgagt tgcaaagtgg tgtcccatca   180
cgtttcagtg gcagtggata tgggacagat ttcactctca ccatcagcag tctgcaacct   240
gaagatttcg ctacgtacta ctgtcaaccg tctttttact cccttatac gttcggccaa    300 gggaccaagg tggaaatcaa acggaccgtc gctgctccag atattcaaat gacccaatcc   360
ccttcctccc tgagcgcttc cgtgggtgac cgtgttacta ttacctgtcg tgcttcccaa   420
tccatctctt cttacctgaa ctggtaccaa caaaagccgg gcaaagcacc gaaactgctg   480
atctatcgca acagcccgct gcagagcggc gtacctagcc gctttagcgg tagcggttcc   540
ggtacggact ttaccctgac tattagctcc ctgcagccag aagattttgc aacgtactat   600
tgccagcaga cctaccgtgt gccgccaacg tttggccagg gtaccaaagt ggaaatcaaa   660
cgc                                                                  663
```

```
<210> SEQ ID NO 14
<211> LENGTH: 663
<212> TYPE: DNA
<213> ORGANISM: Artificial Sequence
<220> FEATURE:
<223> OTHER INFORMATION: Anti IL-1 dAb fused by a linker to a anti-
      serum albumin dAb.
```

-continued

<400> SEQUENCE: 14

```
gacatccaga tgacccagtc tccatcctcc ctgcccgcat ctgtaggaga ccgtgtcacc     60
atcacttgcc gggcaagtca ggatatttac ctgaatttag actggtatca gcagaaacca    120
gggaaagccc ctaagctcct gatcaatttt ggttccgagt tgcaaagtgg tgtcccatca    180
cgtttcagtg gcagtggata tgggacagat ttcactctca ccatcagcag tctgcaacct    240
gaagatttcg ctacgtacta ctgtcaaccg tctttttact tcccttatac gttcggccaa    300
gggaccaagg tggaaatcaa acggaccgtc gctgctccag acatccagat gacccagtct    360
ccatcctccc tgtctgcatc tgtaggagac cgtgtcacca tcacttgccg ggcaagtcag    420
aagattgcta cttatttaaa ttggtatcag cagaaaccag ggaaagcccc taagctcctg    480
atctataggt cttcctcttt gcaaagcgcg gtcccatcac gtttcagtgg cagtggatct    540
gggacagttt tcacactcac catcagcagt ctgcaacctg aagattttgc tacgtactac    600
tgtcaacaga cgtatgctgt tcctcctacg ttcggccaag ggaccaaggt ggaaatcaaa    660
cgg                                                                  663
```

<210> SEQ ID NO 15
<211> LENGTH: 663
<212> TYPE: DNA
<213> ORGANISM: Artificial Sequence
<220> FEATURE:
<223> OTHER INFORMATION: Anti IL-1 dAb fused by a linker to a anti-
      serum albumin dAb.

<400> SEQUENCE: 15

```
gacatccaga tgacccagtc tccatcctcc ctgcccgcat ctgtaggaga ccgtgtcacc     60
atcacttgcc gggcaagtca ggatatttac ctgaatttag actggtatca gcagaaacca    120
gggaaagccc ctaagctcct gatcaatttt ggttccgagt tgcaaagtgg tgtcccatca    180
cgtttcagtg gcagtggata tgggacagat ttcactctca ccatcagcag tctgcaacct    240
gaagatttcg ctacgtacta ctgtcaaccg tctttttact tcccttatac gttcggccaa    300
gggaccaagg tggaaatcaa acggaccgtc gctgctccag acatccagat gacccagtct    360
ccacccctcc tgtccgcatc tgtaggagac cgtgtcacca tcacttgccg ggcaagtcag    420
agcattagca gctatttaaa ttggtatcag cagaaaccag ggaaagcccc taagctcctg    480
atctatcgga attccccttt gcaaagtggg gtcccatcac ggttcagtgg cagtggatct    540
gggacagatt tcactctcac catcagcagt ctgcaacctg aagattttgc tacgtactac    600
tgtcaacaga cttattcgat tcctcctacg ttcggccaag ggaccaaggt ggaaatcaaa    660
cgg                                                                  663
```

<210> SEQ ID NO 16
<211> LENGTH: 596
<212> TYPE: DNA
<213> ORGANISM: Artificial Sequence
<220> FEATURE:
<223> OTHER INFORMATION: Anti IL-1 dAb fused by a linker to a anti-
      serum albumin dAb.

<400> SEQUENCE: 16

```
gacatccaga tgacccagtc tccatcctcc ctgcctgcat ctgtaggaga ccgtgtcacc     60
atcacttgcc gggcaagtca ggatatttac ctgaatttag actggtatca gcagaaacca    120
gggaaagccc ctaagctcct gatcaatttt ggttccgagt tgcaaagggg tgtcccatca    180
cgtttcagtg gcagtggata tgggacagat ttcactctca ccatcagcag tctgcaacct    240
```

```
gaagatttcg ctacgtacta ctgtcaaccg tcttttact tcccttatac gttcggccaa      300
gggaccaagg tggaaatcaa acggaccgtc gctgatattc aaatgaccca atcccttcc      360 tccctgagcg cttccgtggg tgaccgtgtt actattacct gtcgtgcttc ccaatccatc      420
tcttcttacc tgaactggta ccaacaaaag ccgggcaaag caccgaaact gctgatctat      480
cgcaacagcc cgctgcagag cggcgtacct agccgcttta gcggtagcgg ttccggtacg      540
gactttaccc tgactattag ctccctgcag ccagaagatt ttgcaacgta ctattg          596
```

```
<210> SEQ ID NO 17
<211> LENGTH: 708
<212> TYPE: DNA
<213> ORGANISM: Artificial Sequence
<220> FEATURE:
<223> OTHER INFORMATION: Anti IL-1 dAb fused by a linker to a anti-
      serum albumin dAb.

<400> SEQUENCE: 17
```

```
gacatccaga tgacccagtc tccatcctcc ctgcccgcat ctgtaggaga ccgtgtcacc       60
atcacttgcc gggcaagtca ggatatttac ctgaatttag actggtatca gcagaaacca      120
gggaaagccc ctaagctcct gatcaatttt ggttccgagt tgcaaagtgg tgtcccatca      180
cgtttcagtg gcagtggata tgggacagat ttcactctca ccatcagcag tctgcaacct      240
gaagatttcg ctacgtacta ctgtcaaccg tcttttact tcccttatac gttcggccaa      300
gggaccaagg tggaaatcaa acggaccgtc gctgctccag aggtgcagct gttggagtct      360
gggggaggct tggtacagcc tggggggtcc ctgcgtctct cctgtgcagc ctccggattc      420
accttttcga gtattggat gtcgtgggtc cgccaggctc cagggaaggg tctagagtgg      480
gtctcatcta ttgattttat gggtccgcat acatactacg cagactccgt gaagggccgg      540
ttcaccatct cccgcgacaa ttccaagaac acgctgtatc tgcaaatgaa cagcctgcgt      600
gccgaggata ccgcggtata ttactgtgcg aaagggagga cgtcgatgtt gccgatgaag      660
gggaagtttg actactgggg tcagggaacc ctggtcaccg tctcgagc                   708
```

```
<210> SEQ ID NO 18
<211> LENGTH: 694
<212> TYPE: DNA
<213> ORGANISM: Artificial Sequence
<220> FEATURE:
<223> OTHER INFORMATION: Anti IL-1 dAb fused by a linker to a anti-
      serum albumin dAb.

<400> SEQUENCE: 18
```

```
gacatccaga tgacccagtc tccatcctcc ctgcccgcat ctgtaggaga ccgtgtcacc       60
atcacttgcc gggcaagtca ggatatttac ctgaatttag actggtatca gcagaaacca      120
gggaaagccc ctaagctcct gatcaatttt ggttccgagt tgcaaagtgg tgtcccatca      180
cgtttcagtg gcagtggata tgggacagat ttcactctca ccatcagcag tctgcaacct      240
gaagatttcg ctacgtacta ctgtcaaccg tcttttact tcccttatac gttcggccaa      300
gggaccaagg tggaaatcaa acggaccgtc gctgctccag aggtgcagct gttggagtct      360
gggggaggct tggtacagcc tggggggtcc ctgcgtctct cctgtacagc ctccggattc      420
acctttaggc attatcgtat gggttgggtc cgccaggctc cagggaaggg tctagagtgg      480
gtctcatgga ttcgtccgga tggtacgttt acatactacg cagactccgt gaagggccgg      540
ttcaccatct cccgcgacaa ttccaagaac acgctgtatc tgcaaatgaa cagcctgcgt      600
gccgaggaca ccgcggtata ttactgtgcg aaatcttata tgggtgatag gtttgactac      660
```
tggggtcagg gaaccctggt caccgtctcg agcg 694

<210> SEQ ID NO 19
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 19

Ala His Pro Ala Ser Ser Thr Lys Val Asp Lys Lys Ile Val
 1               5                  10

<210> SEQ ID NO 20
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 20

Ala His Pro Ala Ser Ser Thr Lys Val Asp Lys Lys Ile Val
 1               5                  10

<210> SEQ ID NO 21
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 21

Ala His Pro Ala Ser Ser Thr Lys Val Asp Lys Lys Leu Glu
 1               5                  10

<210> SEQ ID NO 22
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 22

Ala His Pro Ala Ser Lys Thr Glu Leu Ile Lys Arg Ile Glu
 1               5                  10

<210> SEQ ID NO 23
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 23

Asn His Lys Pro Ser Asn Thr Lys Val Asp Lys Lys Val Glu
 1               5                  10

<210> SEQ ID NO 24
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 24

Asp His Lys Pro Ser Asn Thr Lys Val Asp Lys Thr Val Glu
 1               5                  10

```
<210> SEQ ID NO 25
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 25

Asn His Lys Pro Ser Asn Thr Lys Val Asp Lys Arg Val Glu
 1               5                  10

<210> SEQ ID NO 26
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 26

Asp His Lys Pro Ser Asn Thr Lys Val Asp Lys Arg Val Glu
 1               5                  10

<210> SEQ ID NO 27
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 27

Ala His Pro Ala Ser Ser Thr Lys Val Asp Lys Lys Ile Val
 1               5                  10

<210> SEQ ID NO 28
<211> LENGTH: 14
<212> TYPE: PRT
<213> ORGANISM: Artificial Sequence
<220> FEATURE:
<223> OTHER INFORMATION: Sequence of G strand of the CH1 domain.

<400> SEQUENCE: 28

Ala His Pro Ala Thr Asn Thr Lys Val Asp Lys Thr Val Ala
 1               5                  10
```

PREVENTION OF AGGREGATION OF IMMUNOGLOBULIN LIGHT OR HEAVY CHAINS

This application is a 371 of International Application No. PCT/EP2007/061514, filed 26 Oct. 2007, which claims the priority of GB Application No. 0621513.1, filed 30 Oct. 2006, the contents of which are herein incorporated by reference in their entirety.

FIELD OF INVENTION

The present invention relates to non-naturally occurring immunoglobulins, and antigen-binding fragments and derivatives thereof, which are modified in order to inhibit aggregation. In a preferred embodiment, the invention provides immunoglobulin single variable domains with improved solubility properties and peptide derivatives that can be used for purification of antibodies. The invention further relates to agents, and in particular polypeptides, capable of inhibiting aggregation of immunoglobulin chains and immunoglobulin domains. In one embodiment, such agents may be used in the therapeutic and prophylactic treatment of diseases characterised by light chain aggregation, for example light chain depositions diseases.

INTRODUCTION

The aggregation of normally soluble proteins into insoluble structures such as ordered, unbranched fibrils and/or irregular amorphous clumps is the underlying pathology associated with a number of diseases, such as the amyloidoses and light chain deposition disease (LCDD) (Falk et al., 1997, *N. Engl. J. Med.* 337:898-909). The hallmark event in aggregation of proteins is a change in the secondary and/or tertiary structure of a normal, soluble protein, rendering it prone to self-assembly into highly ordered para-crystalline arrays (or fibrils) and/or irregular amorphous structures. For example, there are more than twenty proteins that have been clinically identified as the constituent of amyloid fibrils in vivo, including the amyloid precursor protein, Islet amyloid polypeptide, α-synuclein, transthyretin, immunoglobulin light chains, polyglutamine-repeats, and prion proteins. Aggregation of such proteins is intimately associated with diseases such as Alzheimer's, type II diabetes, Parkinson's disease, familial polyneuropathy, light chain deposition diseases, light chain associated amyloidosis, Huntington's disease, and the spongiform encephalopathies.

The risk of developing protein aggregation diseases markedly increases in humans who have aged beyond their fourth decade. Indeed, ageing is possibly the most significant risk factor for the development and progression of protein aggregation and amyloid disease, with the exception of familial forms that often exhibit a much earlier age of onset. Moreover, mutations that result in substitutions in the amino acid sequence of proteins that aggregate in disease such as amyloid-precursor proteins greatly enhance the statistical risk of early-onset amyloid disease. As improved lifestyles have greatly contributed to increasing the life expectancy of humans, the size of the elderly population has progressively increased making it imperative to find therapeutic agents that will halt the progression of protein aggregation diseases. Although many of the protein aggregation diseases such as LCDD and amyloidoses are presently incurable, certain therapies transiently slow the progression of the disease by halting the production of the precursor protein using cytotoxic agents.

Immunoglobulin Structure

The basic structural unit of most mammalian immunoglobulins (e.g. antibodies) is a glycoprotein (MW ~150,000 daltons) composed of four polypeptide chains; two light chains and two heavy chains, which are connected by disulfide bonds (see FIG. 1A). Each light chain has a molecular weight of ~25,000 daltons and is composed of two domains, one variable domain ($V_L$) and one constant domain ($C_L$). There are two types of light chains, lambda (λ) and kappa (κ). In humans, 60% of the light chains are λ, and 40% are κ, whereas in mice, 95% of the light chains are κ and only 5% are λ. A single antibody molecule contains either λ light chains or κ light chains, but never both.

Each heavy chain has a molecular weight of ~50,000 daltons and consists of a constant and variable region. The heavy and light chains contain a number of homologous sections comprising similar but not identical groups of amino acid sequences. These homologous units consist of about 110 amino acids and are called immunoglobulin domains. The heavy chain contains one variable domain ($V_H$) and either three or four constant domains ($C_H1$, $C_H2$, $C_H3$, and $C_H4$, depending on the antibody class or isotype). The region between the $C_H1$ and $C_H2$ domains is called the hinge region and permits flexibility between the two Fab arms of the Y-shaped antibody molecule, allowing them to open and close to accommodate binding to two antigenic determinants.

The heavy chain also serves to determine the functional activity of the antibody molecule. There are five antibody classes—IgG, IgA, IgM, IgE and IgD—which are distinguished by their heavy chains γ, α, μ, ε and δ, respectively. The IgD, IgE and IgG antibody classes are each made up of a single structural unit, whereas IgA antibodies may contain either one or two units and IgM antibodies consist of five disulfide-linked structural units. IgG antibodies are further divided into four subclasses (often referred to as isotypes) although the nomenclature differs slightly depending on the species producing the antibody.

Within the variable domains of immunoglobulin light and heavy chains, there are located three hypervariable regions (or complementarity-determining regions, CDRs) and four framework regions in which the amino acid sequences are relatively conserved (see FIG. 1).

A common structural feature is the presence of two broad sheets of antiparallel β strands, joined by a disulphide bond, with hydrophobic amino acid side chains tightly packed in-between. This recurring structural motif is called an immunoglobulin fold. The C domains contain three β strands in one sheet and four in the apposed sheet while the V domains are similar except for the addition of two extra β strands in one of the sheets.

The hypervariable regions, or CDRs, which determine immunoglobulin specificity, are located in loops at the edges of the two β sheets. Thus, the immunoglobulin fold serves as a conserved framework allowing almost infinite variation of the hypervariable loops.

Studies of Light Chain Structure and Aggregation

Many groups have studied the effects of amino acid substitutions on the thermodynamic stability of the light chain domains. Assessing the consequences of variant residues upon the stability of the domains has shown a good correlation between decreasing folding stability and the increased propensity to form amyloid fibrils. Indeed, mutational analysis of recombinant light chain $V_L$ domains has identified crucial residues in the domain whose replacement invariably results in an increased propensity of fibril formation. Hurle et al. (1994, *Proc. Natl. Acad. Sci.* 91:5446-5450) identified amino acid substitutions in the $V_L$ domain that occur at a very high frequency among amyloid-forming light chains. They found that most of these substitutions occur in positions that are critical for maintaining structural integrity of the light chain domains. For instance, the λ light chain substitutions G57E, G68D, L78T and A84T and the κ light chain replacement of R61N all occur at framework regions. These mutants are less thermodynamically stable than the respective parental, patient derived protein sequence.

In another study, Raffen et al. (1999, *Prot. Sci.* 8:509-517) compared the thermodynamic stabilities of two recombinant κ4 light chain variable domains ($V_Ls$) derived from amyloidogenic light chains with a $V_L$ from a benign light chain. The amyloidogenic $V_L$s were significantly less stable than the benign $V_L$. Furthermore, only the amyloidogenic $V_L$s formed fibrils under physiological conditions in an in vitro fibril formation assay. Using site-directed mutagenesis the consequences of individual amino acid substitutions were examined and found in the amyloidogenic $V_L$s to affect the folding stability and rate of fibrillogenesis. Not surprisingly, only destabilising mutations induced fibril formation in vitro. These results suggested that there are no structural or sequence-specific features of a benign $V_L$ that are incompatible with fibril formation, other than its increased folding stability. The site directed mutants N28F and K30T from CDR1, Y96P and Y96Q from CDR3, and the two mutants L15P and P40L had an increased propensity to form fibrils. These studies show that the $V_L$ β-domain structures are vulnerable to destabilising mutations at a number of sites, including complementarity determining regions (CDRs) and loss of variable domain stability is a major driving force in fibril formation.

Light Chain Diseases

Antibody immunoglobulin variable domains are among the most intensively studied of β protein structures. Their domain architecture is highly conserved, containing several defined features (see Richardson, J. S. & Richardson, D. C. (2002) *Proc Natl Acad Sci USA* 99:2754-9 and Siepen, J. A., Radford, S. E. & Westhead, D. R. (2003) *Protein Sci* 12:2348-59). Certain light chain subsets have a propensity to aggregate both in vitro and in vivo, where they are associated with clinically important disorders: light chain deposition disease and AL amyloidosis. The κ sub-type is particularly prone to aggregation and is responsible for >85% of cases of LCDD (Denoroy et al., 1994, Immunol. Lett. 42, 63-6), despite the fact that it is typically more stable than Vλ. There have been many studies on antibody domains in vitro showing that prolonged incubation under conditions of extreme pH and temperature can lead to partial unfolding and aggregation (Souillac et al., 2003, *Biochemistry* 42, 8094-104).

Light-chain deposition disease (LCDD) is a deposition of monoclonal, amorphous, noncongophilic light chains in multiple organs that do not typically exhibit a fibrillar structure when examined ultrastructurally.

LCDD is an infiltration of light chains involving multiple organs. Renal disease, including renal insufficiency, proteinuria, and nephrotic syndrome, is the major manifestation of LCDD. Many cases are associated with multiple myeloma or lymphoproliferative disease, but as many as 50% of patients have no evidence of neoplastic plasma cell proliferation.

Current Therapeutics and Drug Design Approaches

Approaches leading to the reduction of the availability of precursor proteins have been a primary therapeutic target in the treatment of diseases and conditions associated with aggregation of immunoglobulin light chains. One such approach involves targeting the clone in plasma cells synthesising the precursor proteins during neoplasia, and eradicating the clone by bone marrow transplantation.

More recent approaches for the treatment of light chain associated aggregation diseases involve (i) antiangiogenic drugs in combination with conventional chemotherapy and (ii) active and passive immunotherapy. For instance, it has been shown that circulating idiotype-positive lymphocytes can be targeted for immunotherapy using antibodies such as the anti-CD20 cytotoxic antibody against mature B-cells. Other immunotherapy approaches, such as idiotype vaccinations are also being investigated.

A high-throughput screen of Chalcones, flavonoids and biflavonoids also identified compounds that were able to inhibit fibril formation by a recombinant antibody variable domain (Lin et al., 2001, *Amyloid* 8:182-193).

Accordingly, the present invention seeks to provide engineered antibody chains and variable domains that have reduced propensity to aggregate during storage, thus providing the potential for storage-stable pharmaceutical compositions. The invention further seeks to provide new agents and methods for inhibiting aggregation of immunoglobulin chains, in particular immunoglobulin light chain or $V_L$ aggregation. Such agents have utility in the therapeutic and/or prophylactic treatment of a number of disorders, including LCDD and related conditions.

SUMMARY OF INVENTION

The invention in its broadest sense relates to inhibitors of the aggregation of immunoglobulin chains (and in particular immunoglobulin variable domains) wherein the inhibitor comprises a site for binding to a beta edge, i.e. an exposed main chain backbone of a beta strand of an immunoglobulin chain.

Thus, in one embodiment, there is provided an inhibitor comprising a binding site for binding to the FR1 region of an immunoglobulin chain, or immunoglobulin chain variable domain, thereby inhibiting the aggregation of the immunoglobulin light chains or variable domains. Preferably, the inhibitor binds the FR1 region at or adjacent amino acid position 12, thereby inhibiting the aggregation of immunoglobulin light chains or light chain variable domains.

By "adjacent" amino acid position 12 we mean that the polypeptide of the invention binds sufficiently close to amino acid position 12 to inhibit the aggregation of immunoglobulin light chains or light chain variable domains.

As an alternative to binding to position 12, therefore, the inhibitor may bind the light chain or variable domain (preferably in the FR1 region thereof) such that the inhibitor prevents binding of a second light chain or variable domain to position 12 of the first light chain or variable domain. For example, the inhibitor may bind at any one or more of amino acid positions 9, 10, 11, 12 and/or 13 of the FR1 region of an immunoglobulin light chain or light chain variable domain. Thus, in one embodiment, the inhibitor binds at or adjacent amino acid positions 9 and/or 10.

In a further embodiment, the inhibitor competes with a polypeptide for binding to position 12 of an immunoglobulin light chain or immunoglobulin light chain variable domain, wherein the polypeptide comprises a sequence that is identical to the FR1 sequence of the light chain or variable domain. Competition can be assessed by any suitable assay, for example by FACS or surface plasmon resonance (SPR) (see Cullen et al., 1987-88, *Biosensors* 3(4):211-25).

It will be appreciated by persons skilled in the art that the inhibitor can be an isolated polypeptide or a small molecule.

Preferably, however, the inhibitor comprises or consists of an isolated polypeptide.

For example, the isolated polypeptide may be selected from the group consisting of antibodies and antibody fragments. Preferred antibody and antibody fragments are monoclonal antibodies, Fv fragments, a single chain Fv fragments, disulfide bonded Fv fragments, Fab fragments, Fab' fragments, F(ab')$_2$ fragments, diabodies and immunoglobulin single variable domains.

By "immunoglobulin single variable domain" we include an antibody variable region ($V_H$, $V_{HH}$, $V_L$) that specifically binds a target, antigen or epitope independently of other V domains. However, as the term is used herein, an immunoglobulin single variable domain can be present in a format (e.g. hetero-multimer) with other variable regions or variable domains where the other regions or domains are not required for antigen binding by the single immunoglobulin variable domain (i.e. where the immunoglobulin single variable domain binds antigen independently of the additional variable domains). A "domain antibody" or "dAb" is the same as an "immunoglobulin single variable domain" polypeptide as the term is used herein. An immunoglobulin single variable domain polypeptide, as used herein refers to a mammalian immunoglobulin single variable domain polypeptide, preferably human, but also includes rodent (for example, as disclosed in WO 00/29004) or camelid.

As used herein, "camelid" dAbs are immunoglobulin single variable domain polypeptides which are derived from species including camel, llama, alpaca, dromedary, and guanaco, and comprise heavy chain antibodies naturally devoid of light chain ($V_{HH}$). Similar dAbs can be obtained for single chain antibodies from other species, such as nurse shark.

Exemplary immunoglobulin variable domains are disclosed in WO 03/002609, WO 2004/101790, WO 200/5035572, WO 2004/061026, WO 2004/003019, WO 2004/058821, WO 94/04678, WO 97/49805, WO 99/23221, WO 99/37681, WO 00/24884, WO 00/43507, WO 00/65067, WO 01/40310, WO 03/035694, WO 03/053531, WO 03/054015, WO 03/05527, WO 2004/015425, WO 2004/041862, WO 2004/041863, WO 2004/041865, WO 2004/062551, WO 2005/044858 and EP 1 134 231.

In one embodiment, the polypeptide comprises a variable domain-binding region of a superantigen.

In another embodiment, the polypeptide comprises a non-Ig protein scaffold. Suitable scaffolds are provided by for example natural bacterial receptors such as SpA (for example, see U.S. Pat. No. 5,831,012), those based on fibronectin and affibodies (for example, see WO 98/58965), avimers, lipocallin and CTLA4, as described in van den Beuken et al., *J. Mol. Biol.* 310:591-601 (2001), and scaffolds such as those described in WO 00/69907 (Medical Research Council), which are based for example on the ring structure of bacterial GroEL or other chaperone polypeptides.

Affibody® affinity ligands are small, simple proteins composed of a three-helix bundle based on the scaffold of one of the IgG-binding domains of Protein A from the bacterium *Staphylococcus aureus*. This scaffold has excellent features as an affinity ligand and can be designed to bind with high affinity to any given target protein. The domain consists of 58 amino acids, 13 of which are randomised to generate Affibody® libraries with a large number of ligand variants. Thus, the libraries consist of a multitude of protein ligands with an identical backbone and variable surface-binding properties.

Affibody® libraries can be assembled as described by Nord K. et al (1995) *Protein Eng.* 8:601:608), in particular Example 1 therein.

Affibody® libraries are also available commercially from Affibody AB Box 20137 SE-161 02 Bromma, Sweden Avimers originate from the recombination of families of human serum proteins. They are single protein chains composed of modular binding domains, each of which is designed to bind to a particular target site. The avimers can bind simultaneously to sites on a single protein target and/or sites on multiple protein targets. Known as multi-point attachment or avidity, this binding mechanism mimics the way cells and molecules interact in the body, supports the generation of antagonists and agonists, and results in drugs with multiple functions and potent activity.

Avimers libraries can be produced according to WO 2004/044011 incorporated herein by reference and particularly Example 6 on page 99, and for example US Patent Application (Publication) Nos. 2005/0053973, 2005/0089932, 2005/0164301.

Avimers libraries are also available commercially from Avidia Inc, Mountain View, Calif., USA.

Thus, the first aspect of the invention provides an inhibitor comprising or consisting of a non-naturally occurring polypeptide capable of inhibiting aggregation of immunoglobulin light chains or immunoglobulin light chain variable domains, or a variant, fusion or derivative of such a polypeptide, or a fusion of said variant or derivative thereof, wherein the variant, fusion or derivative retains the capability of the polypeptide to inhibit aggregation of immunoglobulin light chains or immunoglobulin light chain variable domains.

Advantageously, the inhibitor (e.g. polypeptide) is capable of inhibiting H-bond formation between FR1 regions of immunoglobulin light chains or immunoglobulin light chain variable domains.

In a preferred embodiment, the non-naturally occurring polypeptide comprises or consists of:
(a) an amino acid sequence corresponding to the amino acid sequence of the FR1 region of an immunoglobulin light chain variable domain, or part thereof which includes amino acid residue 12 (assigned using the Kabat numbering system); and/or
(b) an amino acid sequence corresponding to the amino acid sequence of the immunoglobulin-binding domain of bacterial superantigen Protein L, or part thereof or a variant, fusion or derivative of such a polypeptide, or a fusion of said variant or derivative thereof, wherein the variant, fusion or derivative retains the capability of the polypeptide to inhibit aggregation of immunoglobulin light chains or immunoglobulin light chain variable domains.

By 'aggregation' of immunoglobulin light chains, or light chain variable domains, we mean the interaction between light chains or light chain variable domains in a folded state, partially unfolded state and/or unfolded state. Such aggregation can propagate to form large masses of associated proteins, which may be ordered (fibrillar) or have an irregular amorphous structure. Preferably, the aggregation is of immunoglobulin light chains or light chain variable domains in a folded state.

The aggregation of immunoglobulin light chains, and the resultant formation of fibrils or amorphous structures, may be measured by techniques well known in the art, such as electron microscopy, binding of human serum amyloid P component (SAP), and Congo red staining (which, when viewed under polarised light, appears bright green). Specific staining with antibodies against Vκ or Vλ light chains confirms AL. Preferred methods for measuring aggregation of immunoglobulin light chains are described in the Examples.

By 'capable of inhibiting' aggregation of immunoglobulin light chains or light chain variable domains we mean that addition of a polypeptide of the invention to a sample or preparation comprising immunoglobulin chains or domains is able to reduce the formation therein of aggregations (fibrils and/or amorphous) compared to aggregation formation (fibrils and/or amorphous structures) in the absence of the polypeptide of the invention. Preferably, formation of protein aggregations is reduced by at least 20%, for example at least 30%, at least 40%, at least 50%, at least 60%, at least 70%, at least 80%, at least 90%, at least 95%, at least 98%, and most preferably 100% (i.e. complete inhibition).

It will be appreciated by persons skilled in the art that the polypeptides of the invention are preferably capable of inhibiting aggregation of immunoglobulin chains or domains under physiological conditions (for example, in vivo).

In a preferred embodiment, the polypeptide, variant, fusion or derivative of the first aspect of the invention comprises or consists of an amino acid sequence corresponding to the amino acid sequence of the FR1 region of an immunoglobulin light chain variable domain, or part thereof which includes amino acid residue 12.

Advantageously, the polypeptide, variant, fusion or derivative comprises or consists of an amino acid sequence corresponding to at least 4 contiguous amino acids from the FR1 region of an immunoglobulin light chain variable domain, for example at least 4, 5, 6, 7, 8, 9, 10, 12, 14, 16, 18 or 20 contiguous amino acids.

Most preferably, the polypeptide, variant, fusion or derivative comprises or consists of an amino acid sequence corresponding to the sequence of amino acids at positions 9 to 12 of from the FR1 region of an immunoglobulin light chain variable domain, i.e. SSLS [SEQ ID NO: 1]. For example, the polypeptide, variant, fusion or derivative may comprise amino acids at positions 5 to 13, 18, 20, 22 and 24 from the FR1 region of an immunoglobulin light chain variable domain.

The immunoglobulin light chain may be derived from any mammalian source. Advantageously, the immunoglobulin light chain is a human immunoglobulin light chain. For example, the immunoglobulin light chain may be encoded by a germline antibody gene segment, e.g. DPK1, DPK2, DPK3, DPK4, DPK5, DPK6, DPK7, DPK8, DPK9, DPK10, DPK12, DPK13, DPK15, DPK16, DPK18, DPK19, DPK20, DPK21, DPK22, DPK23, DPK24, DPK25, DPK26 or DPK28 immunoglobulin gene segment. If desired, the framework can further comprises the framework amino acid sequence encoded by the human germline $J_\kappa 1$, $J_\kappa 2$, $J_\kappa 3$, $J_\kappa 4$, or $J_\kappa 5$ immunoglobulin gene segment.

Preferably, the immunoglobulin light chain is a κ light chain.

Conveniently, the immunoglobulin light chain is a human immunoglobulin light chain.

The framework can be a $V_H$ framework, such as a framework that comprises the framework amino acid sequences encoded by the human germline DP4, DP7, DP8, DP9, DP10, DP31, DP33, DP38, DP45, DP46, DP47, DP49, DP50, DP51, DP53, DP54, DP65, DP66, DP67, DP68 or DP69 immunoglobulin gene segment. If desired, the $V_H$ framework can further comprises the framework amino acid sequence encoded by the human germline $J_H 1$, $J_H 2$, $J_H 3$, $J_H 4$, $J_H 4b$, $J_H 5$ and $J_H 6$ immunoglobulin gene segment.

In certain embodiments, the immunoglobulin chain comprises one or more framework (FR) regions comprising an amino acid sequence that is the same as the amino acid sequence of a corresponding framework region encoded by a human germline antibody gene segment, or the amino acid sequences of one or more of said framework regions collectively comprise up to 5 amino acid differences relative to the amino acid sequence of said corresponding framework region encoded by a human germline antibody gene segment.

In certain embodiments the amino acid sequences of FR1, FR2, FR3 and FR4 of the immunoglobulin chain are the same as the amino acid sequences of corresponding framework regions encoded by a human germline antibody gene segment, or the amino acid sequences of FR1, FR2, FR3 and FR4 collectively contain up to 10 amino acid differences relative to the amino acid sequences of corresponding framework regions encoded by said human germline antibody gene segment.

In a preferred embodiment, the polypeptide, variant, fusion or derivative of the first aspect of the invention comprises or consists of the following amino acid sequence:

PSSLSA.             [SEQ ID NO: 2]

or a variant, fusion or derivative thereof, or a fusion of said variant or derivative thereof which retains the ability of the parent polypeptide to inhibit aggregation of immunoglobulin light chains or immunoglobulin light chain variable domains.

The present invention stems from the identification of a localised area of the first framework region (FR1) of the light chain variable domain which is intimately involved in the light chain aggregation. While not wishing to be bound by theory, it is believed that the polypeptides of the invention inhibit aggregation of light chains or $V_L$ by interfering with the ability of the polypeptide backbone within the FR1 region to form H-bonds. The inhibitors of the invention are thought to inhibit aggregation of light chains or $V_L$ by binding competitively to this localised area within the FR1 region, in so doing preventing the light chain from binding to another light chain or $V_L$ (and forming fibrils or amorphous clumps). This may be achieved by using a polypeptide comprising an amino acid sequence which substantially corresponds to (i.e. is substantially identical to) the amino acid sequence of the FR1 region of an immunoglobulin light chain variable domain, or part thereof, which includes amino acid residue 12 (assigned using the Kabat numbering system).

The same site within the FR1 region is involved in the binding of light chains to the immunoglobulin-binding domain of the bacterial superantigen protein L (also known as PpL for *Peptostreptococcus magnus* protein L). 'Superantigens' are antigens, mostly in the form of toxins expressed in bacteria, which interact with members of the immunoglobulin superfamily outside the conventional ligand binding sites for these molecules. Staphylococcal enterotoxins interact with T-cell receptors and have the effect of stimulating CD4+ T-cells. Superantigens for antibodies include the molecules Protein G that binds the IgG constant region (Bjorck and Kronvall (1984) *J. Immunol,* 133: 969; Reis et al. (1984) *J. Immunol.,* 132: 3091), Protein A that binds the IgG constant region and the VH domain (Forsgren and Sjoquist (1966) *J. Immunol.,* 97: 822) and Protein L that binds the VL domain (Bjorck (1988) *J. Immunol.,* 140: 1994).

Thus, by 'Protein L' we specifically include Protein L derived from *Peptostreptococcus magnus* and having 4 to 5 highly homologous consecutive extracellular domains wherein the number of repeats is strain dependent, e.g. proteins as described in NCBI Accession AAA25612 and AAA67503.

Protein L is a multidomain protein containing 4-5 highly homologous consecutive extracellular domains (also known as "B" repeats), the number is strain dependent. The defined sequence QTAEF [SEQ ID NO: 3] corresponds to the interacting strand of a Protein L domain with a VK1 from a structural complex of an isolated domain with Fab 2A2 (pdb 1HEZ; see Graille, M. et al., 2001, *Structure* 9, 679-687 and Graille, M. et al., 2002, *J. Biol. Chem.* 277, 47500-47506). The fifth domain has the five-residue sequence QTATF [SEQ ID NO: 4] (see Kastern et al., 1992, *J. Biol. Chem.* 267, 12820-12825).

Consequently, a polypeptide, variant, fusion or derivative capable of inhibiting binding of protein L to an immunoglobulin light chain or an immunoglobulin light chain variable domain may also be used to inhibit light chain aggregation. Thus, the polypeptide may comprise an amino acid sequence which corresponds to the amino acid sequence of the immunoglobulin-binding domain of bacterial superantigen protein L, or part thereof. For example, the polypeptide may comprise or consist of an amino acid sequence corresponding to at least 4 contiguous amino acids from the immunoglobulin-binding domain of Protein L, for example at least 5, 6, 7, 8, 9, 10, 12, 14, 16, 18 or 20 contiguous amino acids.

In a further preferred embodiment of the first aspect of the invention, the polypeptide comprises or consists of the amino acid sequence QTAEF [SEQ ID NO: 3]
and/or

QTATF [SEQ ID NO: 4]

or a variant, fusion or derivative thereof, or a fusion of said variant or derivative thereof which retains the ability of the parent polypeptide to inhibit aggregation of immunoglobulin light chains or immunoglobulin light chain variable domains.

It will be appreciated by persons skilled in the art that the numbering of the amino acid residues is strain dependent. For example, Graille. et al., 2002, *J. Biol. Chem.* 277, 47500-47506 provides details on the alignment of B domains and their numbering, depicts those residues involved in interaction with FR1 and lists those that form hydrogen bonds (residues 36, 38, 40 and 53; see Table 1 therein). Adopting the numbering of Graille et al., the QTAEF [SEQ ID NO: 3] domain corresponds to amino acids 35 to 39. Those amino acid residues interacting with this interface are residues 24, 34 to 40, 49, 53 and 56. In terms of the structure, the main contacts are from strand β2 while additional interactions are from strands β1 and the α helix. The antiparallel β strands β1 and β2 joined to the α helix comprise residues 20 to 60 in this domain, and may possibly be larger if the whole of the N-terminus is included (i.e. residues 1 to 60).

As indicated above, the amino acid residues within the FR1 region which are involved in light chain aggregation are also involved in the binding of light chains to the immunoglobulin-binding domain of the bacterial superantigen protein L. Consequently, the polypeptide, variant, fusion or derivative of the invention may also be capable of inhibiting binding of protein L to an immunoglobulin light chain, or a light chain variable domain.

Streptococcal protein G (also referred to as SpG) is believed to contain an immunoglobulin-binding domain that binds to a site in the $C_H1$ region of the immunoglobulin heavy chain via a similar interaction to that of protein L and $V_L$ domains. The structural convergence between the Fab binding modes of protein L and protein G is demonstrated in Graille et al., 2002, *J. Biol. Chem.* 277, 47500-47506. The fold of the SpG binding domain is closely related to that from PpL, consisting of a β sheet formed by two pairs of antiparallel β strands and an α helix on top of the sheet. The interaction of SpG with CHI shares many features with that of PpL and $V_L$. The β2 strand, of the respective domains in SpG and PpL, is involved in interactions and this strand extends a β sheet of the Fab by a β zipper interaction. This interaction involves five main-chain/main-chain hydrogen bonds in the SpG-$C_H1$ interface but only three hydrogen bonds in the PpL-$V_L$.

By 'SpG' we include Streptococcal protein G derived from *streptococcus* group protein G, for example *Streptococcus* strain G148 (Nygren et al., (1988) *J. Mol. Recognit.*, 1:69-74; Nilsson et al., (1994) *Eur. J. Biochem.*, 224:103-108), Guss, B. et al, 1987 *EMBO J.* 5:1567-1575; Olsson, A. et al., 1987 *Eur. J. Biochem.* 168:319-324, U.S. Pat. No. 5,831,012, EP 0 739 353, and EP 0 486 525.

Thus, in an alternative embodiment of the first aspect of the invention, there is provided an inhibitor comprising or consisting of non-naturally occurring polypeptide capable of inhibiting aggregation of immunoglobulin heavy chains or immunoglobulin heavy chain $C_H1$ domains, or a variant, fusion or derivative of such a polypeptide, or a fusion of said variant or derivative thereof, wherein the variant, fusion or derivative retains the capability of the polypeptide to inhibit aggregation of immunoglobulin heavy chains or immunoglobulin heavy chain $C_H1$ domains.

The terms 'aggregation' and 'inhibition' are to be construed in relation to immunoglobulin heavy chains and heavy chain constant domains in a manner consistent with their use as defined above in relation to immunoglobulin light chains and light chain variable domains.

Conveniently, the polypeptide, or variant, fusion or derivative thereof, is capable of inhibiting H-bond formation between $C_H1$ domains of immunoglobulin heavy chains or immunoglobulin heavy chain $C_H1$ domains.

For example, the polypeptide, or variant, fusion or derivative thereof, may be capable of binding at or adjacent amino acid residue 205 to 218 of the $C_H1$ domains of an immunoglobulin heavy chain or immunoglobulin heavy chain $C_H1$ domain.

The SpG and CH1 interaction is stabilised through a series of hydrogen bonds extending from the last β strand in the CH1 domain (strand G; residues 209-216 in murine IgG1, see Table 1) to the second β strand (β2) in protein G (residues 16-22 in the IgG binding domain III, numbered according to Derrick and Wigley. 48, 49).

Table 1: Alignment of the G stand from $C_H1$ domain of γ heavy chain sequences

TABLE 1

Alignment of the G stand from $C_H1$ domain of γ heavy chain sequences

| | Sequence of G strand of the CH1 domain |
|---|---|
| Mouse γ1* | AHPASSTKVDKKIV (SEQ ID NO: 19) |
| Mouse γ2a | AHPASSTKVDKKIV (SEQ ID NO: 20) |
| Mouse γ2b | AHPASSTKVDKKLE (SEQ ID NO: 21) |
| Mouse γ3 | AHPASKTELIKRIE (SEQ ID NO: 22) |
| Human γ1 | NHKPSNTKVDKKVE (SEQ ID NO: 23) |
| Human γ2 | DHKPSNTKVDKTVE (SEQ ID NO: 24) |
| Human γ3 | NHKPSNTKVDKRVE (SEQ ID NO: 25) |
| Human γ4 | DHKPSNTKVDKRVE (SEQ ID NO: 26) |

TABLE 1-continued

Alignment of the G stand from $C_H1$ domain of γ heavy chain sequences

| | Sequence of G strand of the CH1 domain |
|---|---|
| Rat γ1 | AHPASSTKVDKKIV (SEQ ID NO: 27) |
| Rabbit γ | AHPATNTKVDKTVA (SEQ ID NO: 28) |

*Residues 205 to 218 for the Mouse IgG1 are given. Numbering is likely to vary from molecule to molecule pending on the VH class and CDR length of the heavy chain for particular sequences.

In the structure of the complex between CH1 and SpG main chain/main chain hydrogen bonds are formed between positions corresponding to 212, 214 and 216 in the mouse CH1 domain (bold, in Table 1) and positions 20, 18 and 16 of the third B domain (which will subsequently be referred to here as the B3 domain) of protein G, respectively. The residues denoted 20, 18 and 16 in the structure refer to residues 343, 341 and 339 in the NCBI accession CAA27638 of the sequence. The protein has three IgG binding B domains.

Preferably, the polypeptide comprises or consists of an amino acid sequence corresponding to the amino acid sequence of the immunoglobulin-binding domain of SpG, or part thereof.

More preferably, the polypeptide comprises or consists of an amino acid sequence corresponding to at least 4 contiguous amino acids from the immunoglobulin-binding domain of SpG, for example at least 5, 6, 7, 8, 9, 10, 12, 14, 16, 18 or 20 contiguous amino acids.

Most preferably, the polypeptide comprises or consists of the amino acid sequence:

TLKGETT          [SEQ ID NO: 5]

or a variant, fusion or derivative thereof, or a fusion of said variant or derivative thereof which retains the ability of the parent polypeptide to inhibit aggregation of immunoglobulin light chains or immunoglobulin light chain variable domains.

This sequence represents residues 16-22 of the β2 strand, as denoted by Derrick and Wigley (48, 49). The residues in bold form main chain/main chain H bonds to the CH1 B strand G.

Streptococcal protein G sequence can be found as NCBI accession CAA27638, EMBL accession X04015.1; and one example of the structures of a B3 domain in complex with a Fab fragment with a pdb accession 1IGC.

The *Streptococcus* protein G sequence (NCBI accession CAA27638), with the conserved sequence of each B domain involved in IgG binding (bold), is shown:

It will be appreciated by persons skilled in the art that the inhibitor of the first aspect of the invention may comprise or consist of a polypeptide of varying length. Preferably, however, the polypeptide is less than 30 amino acids in length, for example less than 20, less than 15, less than 14, less than 13, less than 12, less than 11, less than 10, less than 9, less than 8, less than 7, or less than 6 amino acids in length. For example, the polypeptide may be between 2 and 20 amino acids in length, for example between 2 and 10, between 4 and 8, between 4 and 6, or exactly 5 or 6 amino acids in length.

It will be further appreciated by persons skilled in the art that the above definitions of the polypeptides of the first aspect of the invention are not intended to encompass naturally occurring or otherwise known immunoglobulin light chains, protein L or SpG. However, the use of such naturally occurring or otherwise known polypeptides is encompassed by the other aspects of the invention, as described below.

In the formulae representing polypeptide embodiments of the present invention, the amino- and carboxy-terminal groups, although not specifically shown, will be understood to be in the form they would assume at physiological pH values, unless otherwise specified. Thus, the N-terminal—$NH^{3+}$ and C-terminal —$COO^-$ at physiological pH are understood to be present though they are not specified and shown. In the polypeptide notation used herein, the left-hand end of the molecule is the amino terminal end and the right-hand end is the carboxy-terminal end, in accordance with standard usage and convention. The basic and acid addition salts including those which are formed at non-physiological pH values are also included in the polypeptides of the invention.

The term 'amino acid' as used herein includes the standard twenty genetically-encoded amino acids and their corresponding stereoisomers in the 'D' form (as compared to the natural 'L' form), omega-amino acids other naturally-occurring amino acids, unconventional amino acids (e.g. α,α-disubstituted amino acids, N-alkyl amino acids, etc.) and chemically derivatised amino acids (see below).

When an amino acid is being specifically enumerated, such as 'alanine' or 'Ala' or 'A', the term refers to both L-alanine and D-alanine unless explicitly stated otherwise. Other unconventional amino acids may also be suitable components for polypeptides of the present invention, as long as the desired functional property is retained by the polypeptide. For the peptides shown, each encoded amino acid residue, where appropriate, is represented by a single letter designation, corresponding to the trivial name of the conventional amino acid.

Preferably, the polypeptides comprise or consist of L-amino acids.

[SEQ ID NO: 6]

```
  1 EFNKYGVSDY YKNLINNAKT VEGVKDLQAQ VVESAKKARI SEATDGLSDF LKSQTPAEDT

61 VKSIELAEAK VLANRELDKY GVSDYHKNLI NNAKTVEGVK DLQAQVVESA KKARISEATD

121 GLSDFLKSQT PAEDTVKSIE LAEAKVLANR ELDKYGVSDY YKNLINNAKT VEGVKALIDE

181 ILAALPKTDT YKLILNGKTL KGETTTEAVD AATAEKVFKQ YANDNGVDGE WTYDDATKTF

241 TVTEKPEVID ASELTPAVTT YKLVINGKTL KGETTTEAVD AATAEKVFKQ YANDNGVDGE

301 WTYDDATKTF TVTEKPEVID ASELTPAVTT YKLVINGKTL KGETTTKAVD AETAEKAFKQ

361 YANDNGVDGV WTYDDATKTF TVTEMVTEVP GDAPTEPEKP EASIPLVPLT PATPIAKDDA

421 KKDDTKKEDA KKPEAKKEDA KKAETLPTTG EGSNPFFTAA ALAVMAGAGA LAVASKRKED
```

It will be appreciated by persons skilled in the art that the first aspect of the invention encompasses variants, fusions and derivatives of the defined polypeptides, as well as fusions of a said variants or derivatives, provided such variants, fusions and derivatives retain the capability of inhibiting light chain aggregation.

Variants may be made using the methods of protein engineering and site-directed mutagenesis well known in the art using the recombinant polynucleotides (see example, see *Molecular Cloning: a Laboratory Manual,* 3rd edition, Sambrook & Russell, 2001, Cold Spring Harbor Laboratory Press).

By 'fusion' of said polypeptide we include a polypeptide fused to any other polypeptide. For example, the said polypeptide may be fused to a polypeptide such as glutathione-S-transferase (GST) or protein A in order to facilitate purification of said polypeptide. Examples of such fusions are well known to those skilled in the art. Similarly, the said polypeptide may be fused to an oligo-histidine tag such as His6 or to an epitope recognised by an antibody such as the well-known Myc tag epitope. Fusions to any variant or derivative of said polypeptide are also included in the scope of the invention. It will be appreciated that fusions (or variants or derivatives thereof) which retain desirable properties, such as light chain aggregation inhibition, are preferred.

It is also particularly preferred if the fusions are ones which are suitable for use in the methods and screening assays described herein.

For example, the fusion may comprise a further portion which confers a desirable feature on the said polypeptide of the invention; for example, the portion may be useful in detecting or isolating the polypeptide, or promoting cellular uptake of the polypeptide. The portion may be, for example, a biotin moiety, a radioactive moiety, a fluorescent moiety, for example a small fluorophore or a green fluorescent protein (GFP) fluorophore, as well known to those skilled in the art. The moiety may be an immunogenic tag, for example a Myc tag, as known to those skilled in the art or may be a lipophilic molecule or polypeptide domain that is capable of promoting cellular uptake of the polypeptide, as known to those skilled in the art.

By 'variants' of the polypeptide we include insertions, deletions and substitutions, either conservative or non-conservative. In particular we include variants of the polypeptide where such changes do not substantially alter the activity of the said polypeptide. In particular, we include variants of the polypeptide where such changes do not substantially alter the inhibition of light chain aggregation by the said polypeptide.

It is particularly preferred, the polypeptide variant has an amino acid sequence which has at least 75% identity with the amino acid sequence given above, more preferably at least 80%, at least 90%, at least 95%, at least 96%, at least 97%, at least 98%, at least 99%, and most preferably 100% identity with an amino acid sequence specified above (i.e. the FR1 region of an immunoglobulin light chain or the immunoglobulin-binding domain of Protein L).

Examples of human, mouse, and camel framework germline sequences are disclosed in Kabat et al. (eds), 1991, *Sequences of Protein of Immunological Interest.* 5th ed National institutes of Health, Bethesda, Md.

The percent sequence identity between two polypeptides may be determined using suitable computer programs, for example the GAP program of the University of Wisconsin Genetic Computing Group and it will be appreciated that percent identity is calculated in relation to polypeptides whose sequences have been aligned optimally.

The alignment may alternatively be carried out using the Clustal W program (as described in Thompson et al., 1994, *Nuc. Acid Res.* 22:4673-4680).

The parameters used may be as follows:
Fast pairwise alignment parameters: K-tuple (word) size; 1, window size; 5, gap penalty; 3, number of top diagonals; 5. Scoring method: x percent.
Multiple alignment parameters: gap open penalty; 10, gap extension penalty; 0.05.
Scoring matrix: BLOSUM.

Alternatively, the BESTFIT program may be used to determine local sequence alignments.

Suitable variants may be identified by nucleic acid hybridisation methodologies, as described in *Current Protocols in Molecular Biology*, John Wiley & Sons, N.Y. (1989), 6.3.1-6.3.6.

Aqueous and non-aqueous methods are described in the above reference and either can be used. Specific hybridisation conditions referred to herein are as follows: (1) low stringency hybridization conditions in 6× Xsodium chloride/sodium citrate (SSC) at about 45° C., followed by two washes in 0.2×SSC, 0.1% SDS at least at 50° C. (the temperature of the washes can be increased to 55° C. for low stringency conditions); (2) medium stringency hybridization conditions in 6×SSC at about 45° C., followed by one or more washes in 0.2×SSC, 0.1% SDS at 60° C.; (3) high stringency hybridization conditions in 6×SSC at about 45° C., followed by one or more washes in 0.2×SSC, 0.1% SDS at 65° C.; and preferably (4) very high stringency hybridization conditions are 0.5M sodium phosphate, 7% SDS at 65° C., followed by one or more washes at 0.2×SSC, 1% SDS at 65° C.

Preferably, nucleic acids molecules encoding suitable variant polypeptides are identified using high stringency conditions (3) or very high stringency conditions (4).

The polypeptide, variant, fusion or derivative of the first aspect of the invention may comprise one or more amino acids which have been modified or derivatised.

Chemical derivatives of one or more amino acids may be achieved by reaction with a functional side group. Such derivatised molecules include, for example, those molecules in which free amino groups have been derivatised to form amine hydrochlorides, p-toluene sulphonyl groups, carboxybenzoxy groups, t-butyloxycarbonyl groups, chloroacetyl groups or formyl groups. Free carboxyl groups may be derivatised to form salts, methyl and ethyl esters or other types of esters and hydrazides. Free hydroxyl groups may be derivatised to form O-acyl or O-alkyl derivatives. Also included as chemical derivatives are those peptides which contain naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine and ornithine for lysine. Derivatives also include peptides containing one or more additions or deletions as long as the requisite activity is maintained. Other included modifications are amidation, amino terminal acylation (e.g. acetylation or thioglycolic acid amidation), terminal carboxylamidation (e.g. with ammonia or methylamine), and the like terminal modifications.

It will be further appreciated by persons skilled in the art that peptidomimetic compounds may also be useful. Thus, by 'polypeptide' we include peptidomimetic compounds which are capable of inhibiting light chain aggregation. The term 'peptidomimetic' refers to a compound that mimics the conformation and desirable features of a particular peptide as a therapeutic agent.

For example, the polypeptides of the invention include not only molecules in which amino acid residues are joined by peptide (—CO—NH—) linkages but also molecules in which the peptide bond is reversed. Such retro-inverso peptidomimetics may be made using methods known in the art, for example such as those described in Meziere et al. (1997) *J. Immunol.* 159, 3230-3237. This approach involves making pseudopeptides containing changes involving the backbone, and not the orientation of side chains. Retro-inverse peptides, which contain NH—CO bonds instead of CO—NH peptide bonds, are much more resistant to proteolysis. Alternatively, the polypeptide of the invention may be a peptidomimetic compound wherein one or more of the amino acid residues are linked by a -y($CH_2NH$)— bond in place of the conventional amide linkage.

In a further alternative, the peptide bond may be dispensed with altogether provided that an appropriate linker moiety which retains the spacing between the carbon atoms of the amino acid residues is used; it is particularly preferred if the linker moiety has substantially the same charge distribution and substantially the same planarity as a peptide bond.

It will be appreciated that the polypeptide may conveniently be blocked at its N- or C-terminus so as to help reduce susceptibility to exoproteolytic digestion.

A variety of uncoded or modified amino acids such as D-amino acids and N-methyl amino acids have also been used to modify mammalian peptides. In addition, a presumed bioactive conformation may be stabilised by a covalent modification, such as cyclisation or by incorporation of lactam or other types of bridges, for example see Veber et al., 1978, *Proc. Natl. Acad. Sci. USA* 75:2636 and Thursell et al., 1983, *Biochem. Biophys. Res. Comm.* 111:166.

A common theme among many of the synthetic strategies has been the introduction of some cyclic moiety into a peptide-based framework. The cyclic moiety restricts the conformational space of the peptide structure and this frequently results in an increased affinity of the peptide for a particular biological receptor. An added advantage of this strategy is that the introduction of a cyclic moiety into a peptide may also result in the peptide having a diminished sensitivity to cellular peptidases.

Thus, preferred polypeptides of the invention comprise terminal cysteine amino acids. Such a polypeptide may exist in a heterodetic cyclic form by disulphide bond formation of the mercaptide groups in the terminal cysteine amino acids or in a homodetic form by amide peptide bond formation between the terminal amino acids. As indicated above, cyclising small peptides through disulphide or amide bonds between the N- and C-terminus cysteines may circumvent problems of affinity and half-life sometime observed with linear peptides, by decreasing proteolysis and also increasing the rigidity of the structure, which may yield higher affinity compounds. Polypeptides cyclised by disulphide bonds have free amino and carboxy-termini which still may be susceptible to proteolytic degradation, while peptides cyclised by formation of an amide bond between the N-terminal amine and C-terminal carboxyl and hence no longer contain free amino or carboxy termini. Thus, the peptides of the present invention can be linked either by a C—N linkage or a disulphide linkage.

The present invention is not limited in any way by the method of cyclisation of peptides, but encompasses peptides whose cyclic structure may be achieved by any suitable method of synthesis. Thus, heterodetic linkages may include, but are not limited to formation via disulphide, alkylene or sulphide bridges. Methods of synthesis of cyclic homodetic peptides and cyclic heterodetic peptides, including disulphide, sulphide and alkylene bridges, are disclosed in U.S. Pat. No. 5,643,872. Other examples of cyclisation methods are discussed and disclosed in U.S. Pat. No. 6,008,058. Cyclic peptides can also be prepared by incorporation of a type 11' β-turn dipeptide (Doyle et al., 1996, *Int J Pept Protein Res.* 47(6):427-36).

A further approach to the synthesis of cyclic stabilised peptidomimetic compounds is ring-closing metathesis (RCM). This method involves steps of synthesising a peptide precursor and contacting it with an RCM catalyst to yield a conformationally restricted peptide. Suitable peptide precursors may contain two or more unsaturated C—C bonds. The method may be carried out using solid-phase-peptide-synthesis techniques. In this embodiment, the precursor, which is anchored to a solid support, is contacted with a RCM catalyst and the product is then cleaved from the solid support to yield a conformationally restricted peptide.

Another approach, disclosed by D. H. Rich in *Protease Inhibitors*, Barrett and Selveson, eds., Elsevier (1986), has been to design peptide mimics through the application of the transition state analogue concept in enzyme inhibitor design. For example, it is known that the secondary alcohol of staline mimics the tetrahedral transition state of the scissile amide bond of the pepsin substrate.

In summary, terminal modifications are useful, as is well known, to reduce susceptibility by proteinase digestion and therefore to prolong the half-life of the peptides in solutions, particularly in biological fluids where proteases may be present. Polypeptide cyclisation is also a useful modification and is preferred because of the stable structures formed by cyclisation and in view of the biological activities observed for cyclic peptides.

Thus, in one embodiment the polypeptide of the first aspect of the invention is cyclic. However, in a alternative preferred embodiment, the polypeptide is linear.

The present invention also includes compositions comprising pharmaceutically acceptable acid or base addition salts of the polypeptides of the present invention. The acids which are used to prepare the pharmaceutically acceptable acid addition salts of the aforementioned base compounds useful in this invention are those which form non-toxic acid addition salts, i.e. salts containing pharmacologically acceptable anions, such as the hydrochloride, hydrobromide, hydroiodide, nitrate, sulphate, bisulphate, phosphate, acid phosphate, acetate, lactate, citrate, acid citrate, tartrate, bitartrate, succinate, maleate, fumarate, gluconate, saccharate, benzoate, methanesulphonate, ethanesulphonate, benzenesulphonate, p-toluenesulphonate and pamoate [i.e. 1,1'-methylene-bis-(2-hydroxy-3 naphthoate)] salts, among others.

Pharmaceutically acceptable base addition salts may also be used to produce pharmaceutically acceptable salt forms of the compounds according to the present invention.

The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (e.g. potassium and sodium) and alkaline earth metal cations (e.g. calcium and magnesium), ammonium or water-soluble amine addition salts such as N-methylglucamine-(meglumine), and the lower alkanolammonium and other base salts of pharmaceutically acceptable organic amines, among others.

The polypeptides of this invention may be lyophilised for storage and reconstituted in a suitable carrier prior to use. Any suitable lyophilisation method (e.g. spray drying, cake drying) and/or reconstitution techniques can be employed. It will be appreciated by those skilled in the art that lyophilisation and reconstitution can lead to varying degrees of antibody activity loss (e.g. with conventional immunoglobulins, IgM antibodies tend to have greater activity loss than IgG antibodies) and that use levels may have to be adjusted upward to compensate. Preferably, the lyophilised (freeze dried) polypeptide loses no more than about 20%, or no more than about 25%, or no more than about 30%, or no more than about 35%, or no more than about 40%, or no more than about 45%, or no more than about 50% of its activity (prior to lyophilisation) when rehydrated.

It will be appreciated by persons skilled in the art that the polypeptides of the invention may exist in monomeric form or in the form of a homo- or hetero-multimer thereof (e.g. dimer, trimer, tetramer, pentamer, etc.).

A second aspect of the invention provides an isolated nucleic acid molecule encoding a polypeptide, variant, fusion or derivative as defined above according to the first aspect of the invention.

Thus, the isolated nucleic acid molecule is suitable for expressing a polypeptide inhibitor of the invention. By 'suitable for expressing' is meant that the nucleic acid molecule is a polynucleotide that may be translated to form the polypeptide, for example RNA, or that the polynucleotide (which is preferably DNA) encoding the polypeptide of the invention is inserted into an expression vector, such as a plasmid, in proper orientation and correct reading frame for expression. The polynucleotide may be linked to the appropriate transcriptional and translational regulatory control nucleotide sequences recognised by any desired host; such controls may be incorporated in the expression vector.

The nucleic acid molecule of the invention may be DNA or RNA, preferably DNA.

The nucleic acid molecule (or polynucleotide) may be expressed in a suitable host to produce a polypeptide of the invention. Thus, the polynucleotide encoding the polypeptide of the invention may be used in accordance with known techniques, appropriately modified in view of the teachings contained herein, to construct an expression vector, which is then used to transform an appropriate host cell for the expression and production of the polypeptide of the invention (for example as described in Sambrook & Russell, supra.)

The nucleic acid molecule encoding the polypeptide of the invention may be joined to a wide variety of other polynucleotide sequences for introduction into an appropriate host. The companion polynucleotide will depend upon the nature of the host, the manner of the introduction of the polynucleotide into the host, and whether episomal maintenance or integration is desired.

Generally, the nucleic acid molecule is inserted into an expression vector, such as a plasmid, in proper orientation and correct reading frame for expression. If necessary, the nucleic acid molecule may be linked to the appropriate transcriptional and translational regulatory control nucleotide sequences recognised by the desired host, although such controls are generally available in the expression vector. The vector is then introduced into the host through standard techniques. Generally, not all of the hosts will be transformed by the vector. Therefore, it will be necessary to select for transformed host cells. One selection technique involves incorporating into the expression vector a polynucleotide sequence, with any necessary control elements, that codes for a selectable trait in the transformed cell, such as antibiotic resistance. Alternatively, the gene for such selectable trait can be on another vector, which is used to co-transform the desired host cell.

Host cells that have been transformed by the recombinant nucleic acid molecule of the invention are then cultured for a sufficient time and under appropriate conditions known to those skilled in the art in view of the teachings disclosed herein to permit the expression of the polypeptide, which can then be recovered.

Many expression systems are known, including bacteria (for example *E. coli* and *Bacillus subtilis*), yeasts (for example *Saccharomyces cerevisiae*), filamentous fungi (for example *Aspergillus*), plant cells, animal cells and insect cells.

The vectors typically include a prokaryotic replicon, such as the ColE1 ori, for propagation in a prokaryote, even if the vector is to be used for expression in other, non-prokaryotic, cell types. The vectors can also include an appropriate promoter such as a prokaryotic promoter capable of directing the expression (transcription and translation) of the genes in a bacterial host cell, such as *E. coli*, transformed therewith. Promoter sequences compatible with exemplary bacterial hosts are typically provided in plasmid vectors containing convenient restriction sites for insertion of a polynucleotide of the present invention.

Typical prokaryotic vector plasmids are pUC18, pUC19, pBR322 and pBR329 available from Biorad Laboratories, (Richmond, Calif., USA) and pTrc99A and pKK223-3 available from Pharmacia, Piscataway, N.J., USA.

A typical mammalian cell vector plasmid is pSVL available from Pharmacia, Piscataway, N.J., USA. This vector uses the SV40 late promoter to drive expression of cloned genes, the highest level of expression being found in T antigen-producing cells, such as COS-1 cells.

An example of an inducible mammalian expression vector is pMSG, also available from Pharmacia. This vector uses the glucocorticoid-inducible promoter of the mouse mammary tumour virus long terminal repeat to drive expression of the cloned gene.

Useful yeast plasmid vectors are pRS403-406 and pRS413-416 and are generally available from Stratagene Cloning Systems, La Jolla, Calif. 92037, USA. Plasmids pRS403, pRS404, pRS405 and pRS406 are Yeast Integrating plasmids (YIps) and incorporate the yeast selectable markers HIS3, TRP1, LEU2 and URA3. Plasmids pRS413-416 are Yeast Centromere plasmids (YCps).

The present invention also relates to a host cell transformed with a polynucleotide vector construct of the present invention. The host cell can be either prokaryotic or eukaryotic. Bacterial cells are preferred prokaryotic host cells and typically are a strain of *E. coli* such as, for example, the *E. coli* strains DH5 available from Bethesda Research Laboratories Inc., Bethesda, Md., USA, and RR1 available from the American Type Culture Collection (ATCC) of Rockville, Md., USA (No ATCC 31343). Preferred eukaryotic host cells include yeast, insect and mammalian cells, preferably vertebrate cells such as those from a mouse, rat, monkey or human fibroblastic and kidney cell lines. Yeast host cells include YPH499, YPH500 and YPH501 which are generally available from Stratagene Cloning Systems, La Jolla, Calif. 92037, USA. Preferred mammalian host cells include Chinese hamster ovary (CHO) cells available from the ATCC as CCL61, NIH Swiss mouse embryo cells NIH/3T3 available from the ATCC as CRL 1658, monkey kidney-derived COS-1 cells available from the ATCC as CRL 1650 and 293 cells which are human embryonic kidney cells. Preferred insect cells are Sf9 cells which can be transfected with baculovirus expression vectors.

Transformation of appropriate cell hosts with a nucleic acid molecule of the present invention is accomplished by well known methods that typically depend on the type of vector used. With regard to transformation of prokaryotic host cells, see for example Sambrook & Russell (supra). Transformation of yeast cells is described in numerous reviews, for example see Gietz & Woods (2001) *Biotechniques* 30:816-228. With regard to vertebrate cells, reagents useful in transfecting such cells, for example calcium phosphate and DEAE-dextran or liposome formulations, are available from Stratagene Cloning Systems, or Life Technologies Inc., Gaithersburg, Md. 20877, USA.

Electroporation is also useful for transforming and/or transfecting cells and is well known in the art for transforming yeast cell, bacterial cells, insect cells and vertebrate cells. For example, many bacterial species may be transformed by the methods described in Luchansky et al. (1988) *Mol. Microbiol.* 2:637-646. Methods for transformation of yeast by electroporation are disclosed in Becker & Guarente (1990) *Methods Enzymol.* 194:182.

Successfully transformed cells, i.e. cells that contain a nucleic acid molecule of the present invention, can be identified by well known techniques. For example, cells resulting from the introduction of an expression construct of the present invention can be grown to produce the polypeptide of the invention. Cells can be harvested and lysed and their DNA content examined for the presence of the DNA using a method such as that described by Sambrook & Russell (supra.). Alternatively, the presence of the protein in the supernatant can be detected using antibodies.

In addition to assaying directly for the presence of recombinant DNA, successful transformation can be confirmed by well known immunological methods when the recombinant DNA is capable of directing the expression of the protein. For example, cells successfully transformed with an expression vector produce proteins displaying appropriate antigenicity. Samples of cells suspected of being transformed are harvested and assayed for the protein using suitable antibodies.

Thus, a third aspect of the invention provides a vector comprising a nucleic acid molecule according to the second aspect of the invention. In a preferred embodiment, the vector is an expression vector.

Advantageously, the vector is suitable for replication in a eukaryotic cell, such as a mammalian cell.

Preferred vectors may be selected from the group consisting of pBudCE4.1 pTWIN, pShuttle, pUC18, pUC19, pBacPAK, pBR322, pBR329, pTrc99A, pKK223-3, pSVL, pMSG, pRS403 to 406, pRS413 to 416 and pPicZalpha.

A fourth aspect of invention provides a host cell comprising a nucleic acid molecule according to the second aspect of the invention or a vector according to the third aspect of the invention. Conveniently, the cell is a eukaryotic cell, for example a mammalian cell.

Preferably, the host cell is selected from the group consisting of *E. coli* strain DH5, RR1, ER2566, CHO cells (e.g. CCL61), NIH Swiss mouse embryo cells (NIH/3T3), COS-1 cells (e.g. CRL 1650 and 293), Sf9 cells and yeast cell lines YPH499 to 501, or *Pichia Pastoris* such as KM71H.

In addition to the transformed host cells themselves, the present invention also contemplates a culture of those cells, preferably a monoclonal (clonally homogeneous) culture, or a culture derived from a monoclonal culture, in a nutrient medium.

A fifth aspect of the invention provides a method for making a polypeptide inhibitor according to the first aspect of the invention, the method comprising culturing a host cell according to the fourth aspect of the invention which expresses the polypeptide, and isolating the polypeptide therefrom. Methods of cultivating host cells and isolating recombinant proteins are well known in the art.

A sixth aspect of the invention provides a method for making a polypeptide inhibitor according to the first aspect of the invention comprising solid phase synthesis of the polypeptide. For example, the polypeptides may be synthesised as described in *Solid-Phase Peptide Synthesis* (1997) Fields, Abelson & Simon (Eds), Academic Press (ISBN: 0-12-182190-0).

A seventh aspect of the invention provides a pharmaceutical formulation comprising an inhibitor according to the first aspect of the invention in admixture with a pharmaceutically or veterinarily acceptable excipient, diluent or carrier.

As used herein, 'pharmaceutical formulation' means a therapeutically effective formulation according to the invention.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Thus, in a preferred embodiment, the present invention provides a pharmaceutical formulation comprising an amount of an inhibitor of the invention effective to inhibit (at least in part) one or more of the following:
(a) aggregation of immunoglobulin light or heavy chains (including $V_L$ or $C_H1$ domains);
(b) binding of PpL to immunoglobulin light chains and/or immunoglobulin light chain variable domains; and/or
(c) binding of SpG to immunoglobulin heavy chains and/or immunoglobulin heavy chain $C_H1$ domain.

It will be appreciated by persons skilled in the art that the inhibitors of the invention will generally be administered in admixture with a suitable pharmaceutical excipient diluent or carrier selected with regard to the intended route of administration and standard pharmaceutical practice (for example, see Remington: The Science and Practice of Pharmacy, 19th edition, 1995, Ed. Alfonso Gennaro, Mack Publishing Company, Pennsylvania, USA). Suitable routes of administration are discussed below, and include topical, intravenous, oral, pulmonary, nasal, aural, ocular, bladder and CNS delivery.

For example, polypeptide inhibitors and pharmaceutical formulations of the present invention may be delivered using an injectable sustained-release drug delivery system, such as a microsphere. These are designed specifically to reduce the frequency of injections. An example of such a system is Nutropin Depot which encapsulates recombinant human growth hormone (rhGH) in biodegradable microspheres that, once injected, release rhGH slowly over a sustained period.

Alternatively, the inhibitors and pharmaceutical formulations of the present invention can be administered by a surgically implanted device that releases the drug directly to the required site.

Electroporation therapy (EPT) systems can also be employed for the administration of inhibitors, such as polypeptides. A device which delivers a pulsed electric field to cells increases the permeability of the cell membranes to the drug, resulting in a significant enhancement of intracellular drug delivery.

Inhibitors can also be delivered by electroincorporation (EI). EI occurs when small particles of up to 30 microns in diameter on the surface of the skin experience electrical pulses identical or similar to those used in electroporation. In EI, these particles are driven through the stratum corneum and into deeper layers of the skin. The particles can be loaded or coated with drugs or genes or can simply act as "bullets" that generate pores in the skin through which the drugs can enter.

An alternative method of inhibitor delivery is the thermosensitive ReGel injectable medium. Below body temperature, ReGel is an injectable liquid while at body temperature it immediately forms a gel reservoir that slowly erodes and dissolves into known, safe, biodegradable polymers. The active drug is delivered over time as the biopolymers dissolve.

Inhibitors can also be delivered orally. One such system for delivery of polypeptides employs a natural process for oral uptake of vitamin B12 in the body to co-deliver proteins and polypeptides. By riding the vitamin B12 uptake system, the protein or polypeptide can move through the intestinal wall.

Complexes are produced between vitamin B12 analogues and the drug that retain both significant affinities for intrinsic factor (IF) in the vitamin B12 portion of the complex and significant bioactivity of the drug portion of the complex.

Preferably, the pharmaceutical formulation of the present invention is a unit dosage containing a daily dose or unit, daily sub-dose or an appropriate fraction thereof, of the active ingredient.

The inhibitors and pharmaceutical formulations of the present invention will normally be administered orally or by any parenteral route, in the form of a pharmaceutical formulation comprising the active ingredient, optionally in the form of a non-toxic organic, or inorganic, acid, or base, addition salt, in a pharmaceutically acceptable dosage form. Depending upon the disorder and patient to be treated, as well as the route of administration, the compositions may be administered at varying doses.

In human therapy, the inhibitors of the invention can be administered alone but will generally be administered in admixture with a suitable pharmaceutical excipient diluent or carrier selected with regard to the intended route of administration and standard pharmaceutical practice.

For example, the inhibitors, e.g. polypeptides, of the invention can be administered orally, buccally or sublingually in the form of tablets, capsules, ovules, elixirs, solutions or suspensions, which may contain flavouring or colouring agents, for immediate-, delayed- or controlled-release applications. The compounds of invention may also be administered via intracavernosal injection.

Such tablets may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropyl-methylcellulose (HPMC), hydroxy-propylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compounds of the invention may be combined with various sweetening or flavouring agents, colouring matter or dyes, with emulsifying and/or suspending agents and with diluents such as water, ethanol, propylene glycol and glycerin, and combinations thereof.

The inhibitors of the invention can also be administered parenterally, for example, intravenously, intra-articularly, intra-arterially, intraperitoneally, intra-thecally, intraventricularly, intrasternally, intracranially, intramuscularly or subcutaneously, or they may be administered by infusion techniques. They are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well known to those skilled in the art.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

For oral and parenteral administration to human patients, the daily dosage level of the compounds of the invention will usually be from 1 to 1000 mg per adult (i.e. from about 0.015 to 15 mg/kg), administered in single or divided doses.

Thus, for example, the tablets or capsules of the inhibitors of the invention may contain from 1 mg to 1000 mg of active compound for administration singly or two or more at a time, as appropriate. The physician in any event will determine the actual dosage which will be most suitable for any individual patient and it will vary with the age, weight and response of the particular patient. The above dosages are merely exemplary of the average case. There can, of course, be individual instances where higher or lower dosage ranges are merited and such are within the scope of this invention.

The inhibitors of the invention can also be administered intranasally or by inhalation and are conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A3 or 1,1,1,2,3,3,3-heptafluoropropane (HFA 227EA3), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the invention and a suitable powder base such as lactose or starch.

Aerosol or dry powder formulations are preferably arranged so that each metered dose or 'puff' contains at least 1 mg of a compound of the invention for delivery to the patient. It will be appreciated that the overall daily dose with an aerosol will vary from patient to patient, and may be administered in a single dose or, more usually, in divided doses throughout the day.

Alternatively, the inhibitors of the invention can be administered in the form of a suppository or pessary, or they may be applied topically in the form of a lotion, solution, cream, ointment or dusting powder. The compounds of the invention may also be transdermally administered, for example, by the use of a skin patch. They may also be administered by the ocular route.

For ophthalmic use, the inhibitors of the invention can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the inhibitors of the invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

Generally, in humans, oral or parenteral administration of the inhibitors of the invention is the preferred route, being the most convenient.

It will be appreciated by persons skilled in the art that such an effective amount of the inhibitor or formulation thereof may be delivered as a single bolus dose (i.e. acute administration) or, more preferably, as a series of doses over time (i.e. chronic administration).

It will be further appreciated by persons skilled in the art that the inhibitors and pharmaceutical formulations of the present invention have utility in both the medical and veterinary fields. Thus, the inhibitors of the invention may be used in the treatment of both human and non-human animals (such as horses, dogs and cats). Preferably, however, the patient is human.

For veterinary use, an inhibitor of the invention is administered as a suitably acceptable formulation in accordance with normal veterinary practice and the veterinary surgeon will determine the dosing regimen and route of administration which will be most appropriate for a particular animal.

In an eighth aspect of the invention, there is provided an inhibitor according to the first aspect of the invention or a pharmaceutical formulation according to the seventh aspect of the invention for use in medicine.

A ninth aspect of the invention provides the use of an inhibitor according to the first aspect of the invention, or a naturally occurring equivalent thereof, or a pharmaceutical formulation according to the seventh aspect of the invention in the preparation of a medicament for treating a disease or condition associated with aggregation of immunoglobulin chains.

By "naturally occurring equivalent thereof" we include naturally occurring or otherwise known proteins and polypeptides capable of inhibiting the aggregation of immunoglobulin chains (or immunoglobulin $V_L$ or $C_H1$ domains) which exhibit the properties of the inhibitors as defined above in relation to the first aspect of the invention. For example, the naturally occurring equivalent may comprise an amino acid sequence according to any one or more of SEQ ID NOS: 1 to 5.

In a preferred embodiment, the immunoglobulin chains are immunoglobulin light chains or immunoglobulin light chain variable domains.

In an alternative preferred embodiment, the immunoglobulin chains are immunoglobulin heavy chains or immunoglobulin heavy chain domains.

Thus, the inhibitors and formulations of the present invention may be used in the preparation of a medicament for treating a disease or condition associated with fibril formation in immunoglobulin chains. For example, the fibril formation may be mediated by regions of the immunoglobulin chains having a single cis-proline. In one embodiment, the fibres comprise or consist of Vκ chains.

Preferably, the inhibitors and formulations of the present invention may be used to treat patients or subjects who suffer from or are at risk of suffering from the following conditions or disease states:

Light chain deposition disease (LCDD), amyloid diseases, bacterial infection and diseases/conditions characterised by excess histamine production.

More preferably, the patient or subject suffers from or are at risk of suffering from a light chain deposition disease (LCDD).

Alternatively, the patient or subject suffers from or are at risk of suffering from an amyloid disease.

PpL has been described as a virulence factor of bacterial vaginosis in different clinical specimens (see Kastern et al., 1990, *Infect. Immun* 58, 1217-22). Several pathogenic bacteria present cell surface proteins with IgG binding properties that confer on them an advantage during invasion and colonization of host tissues. PpL induces histamine release by basophils and mast cells, by cross linking IgE bound to Fcε receptors (see Patella et al., 1990, *J. Immunol.* 145, 3054-61; Genovese et al., 2000, *Infect. Immun.* 68, 5517-24).

In a further preferred embodiment, the invention provides the use of an inhibitor according to the first aspect of the invention, or a naturally occurring equivalent thereof, or a pharmaceutical formulation according to the seventh aspect of the invention in the preparation of a medicament for treating infection with a bacterium. Preferably, the bacterium is selected from the group consisting of *Peptostreptococcal* and *Streptococcal* bacteria.

Thus, the invention provides a method of treating a patient in need of treatment with an agent capable of inhibiting aggregation of immunoglobulin chains (as described above), the method comprising administering to the patient an effective amount of an inhibitor according to the first aspect of the invention, or a naturally occurring equivalent thereof, or a pharmaceutical formulation according to the seventh aspect of the invention.

The invention further provides a method of treating a patient infected with or susceptible to infection with a bacterium (as described above), the method comprising administering to the patient an effective amount of an inhibitor according to the first aspect of the invention, or a naturally occurring equivalent thereof, or a pharmaceutical formulation according to the seventh aspect of the invention.

By 'treatment' and 'treating' we include both therapeutic and prophylactic treatment of the patient. The term 'prophylactic' is used to encompass the use of an inhibitor or formulation described herein which either prevents or reduces the likelihood of a condition or disease state in a patient or subject.

As discussed above, the term 'effective amount' is used herein to describe concentrations or amounts of compounds according to the present invention which may be used to produce a favourable change in a disease or condition treated, whether that change is a remission, a favourable physiological result, a reversal or attenuation of a disease state or condition treated, the prevention or the reduction in the likelihood of a condition or disease state occurring, depending upon the disease or condition treated. Where polypeptides of the invention are used in combination, each of the polypeptides may be used in an effective amount, wherein an effective amount may include a synergistic amount.

It will be appreciated by persons skilled in the art that the inhibitors and formulations of the invention may be co-administered in combination with one or more known or conventional agents for the treatment of the particular disease or condition. By 'co-administer' it is meant that the present inhibitors are administered to a patient such that the inhibitors as well as the co-administered compound may be found in the patient's body (e.g. in the bloodstream) at the same time, regardless of when the compounds are actually administered, including simultaneously.

For example, where the patient is suffering from an amyloid disease or condition, the inhibitor or formulation of the invention comprises may be administered in combination with chemo/radiotherapy and/or a peripheral blood stem-cell transplantation.

Likewise, where the patient is suffering from a bacterial infection, the inhibitor or formulation of the invention comprises may be administered in combination with one or more conventional antibiotic agents.

A tenth aspect of the present invention further provides the use of an inhibitor according to the first aspect of the invention, or a naturally occurring equivalent thereof, or a pharmaceutical formulation according to the seventh aspect of the invention to prevent immunoglobulin chain aggregation.

For example, a polypeptide, variant, fusion or derivative according to the first aspect of the invention or a pharmaceutical formulation according to the seventh aspect of the invention may be used as an additive to stabilise an immunoglobulin sample/preparation in vitro. Thus, the invention further encompasses such immunoglobulin samples/preparations.

An eleventh aspect of the invention provides a method of isolating or purifying an antibody, or antigen-binding fragment or derivative thereof, from a sample, wherein the method comprises contacting the sample with an inhibitor according to the first aspect of the invention, or a naturally occurring equivalent thereof, under conditions which allow the antibody, or antigen-binding fragment or derivative thereof, if present in the sample, to bind thereto. Once other impurities are removed, the antibody, or antigen-binding fragment or derivative thereof, may then be collected by disrupting its binding to the inhibitor according to the first aspect of the invention.

A twelfth aspect of the invention provides a method of detecting the presence or absence of an antibody, or antigen-binding fragment or derivative thereof, in a sample, wherein the method comprises contacting the sample with an inhibitor according to the first aspect of the invention, or a naturally occurring equivalent thereof, under conditions which allow the antibody, or antigen-binding fragment or derivative thereof, if present in the sample, to bind thereto.

In a preferred embodiment of the eleventh and twelfth aspects of the invention, the inhibitor is immobilised. For example, the inhibitor may form the affinity matrix of a chromatography column.

Examples of columns that offer supports to covalently link a peptide/protein of interest include Activated ProSep (ProSep-5CHO and ProSep-9CHO) from Millipore; Affi-Gel from BioRad.

A thirteenth aspect of the invention provides a method for identifying a drug-like compound, or lead compound for the development of a drug-like compound, which compound is capable of inhibiting aggregation of immunoglobulin chains, the method comprising the step of testing said compound for an ability to compete with an inhibitor according to the first aspect of the invention, or a naturally occurring equivalent thereof, for binding to an immunoglobulin chain.

In a preferred embodiment, the immunoglobulin chains are immunoglobulin light chains or immunoglobulin light chain variable domains.

In an alternative preferred embodiment, the immunoglobulin chains are immunoglobulin heavy chains or immunoglobulin heavy chain $C_H1$ domains.

The ability of candidate compounds to inhibit aggregation of immunoglobulin chains, or domains thereof, may be assessed by a competitive binding assay, e.g. affinity chromatography or BIAcore. Candidate compounds may be polypeptide or non-polypeptide compounds. Inhibition of light chain aggregation may be quantified by the ability of the test compounds to compete with a first polypeptide of the invention for binding to a second polypeptide of the invention or to immunoglobulin light chains, or variable domains thereof, e.g. by displacing the polypeptide. The displaced polypeptide can be assayed by a number of techniques. For example, radiolabelled polypeptide can be synthesized using commercial available radiolabelled amino acids precursors. Polypeptide radiolabelled with $^3H$, $^{14}C$ or $^{35}S$ can be quantified by routine liquid scintillation techniques. Alternatively, a fluorescent-labelled polypeptide can be synthesized. For example, lysine can be inserted in a non-critical position and labelled with fluoroescein isothiocyanate (FITC). In addition to FITC, the polypeptide may be labelled with any suitable fluorophore. A carboxy fluoroescein derivative of one or more of the polypeptides of the present invention may be prepared. Alternatively, polypeptides cyclised with an amide peptide linkage have free sulfhydryl groups available for linkage to fluorescent compounds such as thiocyanates. Separation of bound from unbound polypeptide and quantitation of displaced polypeptide can be performed by routine techniques known to one of skill in the art.

This embodiment of the invention is not limited by the method used to quantify the displaced polypeptide, and it will be appreciated that any suitable analytical technique may be used.

A related aspect of the invention provides a method for identifying a drug-like compound, or lead compound for the development of a drug-like compound, which compound is capable of inhibiting binding of PpL to immunoglobulin light chains, or immunoglobulin light chain variable domains, the method comprising the step of testing said compound for an ability to compete with an inhibitor according to the first aspect of the invention, or a naturally occurring equivalent thereof, for binding to an immunoglobulin light chain or immunoglobulin light chain variable domain.

A further related aspect of the invention provides a method for identifying a drug-like compound, or lead compound for the development of a drug-like compound, which compound is capable of inhibiting binding of SpG to immunoglobulin heavy chains, or immunoglobulin heavy chain $C_H1$ domain, the method comprising the step of testing said compound for an ability to compete with an inhibitor according to the first aspect of the invention, or a naturally occurring equivalent thereof, for binding to an immunoglobulin heavy chain or immunoglobulin heavy chain $C_H1$ domain.

The candidate compound may be a drug-like compound or lead compound for the development of a drug-like compound for each of the above methods of identifying a compound. It will be appreciated that the said methods may be useful as screening assays in the development of pharmaceutical compounds or drugs, as well known to those skilled in the art.

The term 'drug-like compound' is well known to those skilled in the art, and may include the meaning of a compound that has characteristics that may make it suitable for use in medicine, for example as the active ingredient in a medicament. Thus, for example, a drug-like compound may be a molecule that may be synthesized by the techniques of organic chemistry, less preferably by techniques of molecular biology or biochemistry, and is preferably a small molecule, which may be of less than 5000 daltons molecular weight. A drug-like compound may additionally exhibit features of selective interaction with a particular protein or proteins and be bioavailable and/or able to penetrate cellular membranes, but it will be appreciated that these features are not essential.

The term 'lead compound' is similarly well known to those skilled in the art, and may include the meaning that the compound, whilst not itself suitable for use as a drug (for example because it is only weakly potent against its intended target, non-selective in its action, unstable, difficult to synthesize or has poor bioavailability) may provide a starting-point for the design of other compounds that may have more desirable characteristics.

It will be appreciated that the compound may be a polypeptide that is capable of competing with the inhibitor of the invention for binding to the FR1 region of an immunoglobulin light chain.

It will be further appreciated that it will be desirable to identify compounds that may inhibit light chain aggregation in vivo. Thus, it will be understood that reagents and conditions used in the method may be chosen such that the interactions between the said polypeptides and the immunoglobulin light chain are substantially the same as between light chains in vivo.

The 'drug-like compounds' and 'lead compounds' identified in the screening assays of the invention are suitably tested in further screens to determine their potential usefulness in treating light chain deposition diseases, etc.

In a preferred embodiment of the thirteenth aspect of the invention, the method further comprises the step of mixing the compound thus identified with a pharmaceutically acceptable carrier.

The method may also comprise the step of providing the results of the screening assay in an intelligible format, for example recorded or stored on an information carrier or saved as a computer-readable file.

The invention also provides a compound obtainable or obtained by a method according to the thirteenth aspect of the invention, as well as such compounds for use in medicine.

As detailed above, the inhibitors of the present invention are capable of binding to the FR1 region of the immunoglobulin light chains at amino acid position 12. The inventors have identified this amino acid as the site at which immunoglobulin light chains bind to each other during the aggregation process. By effectively blocking this binding site, the inhibitors of the invention are able to inhibiting light chain aggregation.

An alternative strategy for inhibiting light chain aggregation, also encompassed by the present invention, is to modify the immunoglobulin light chain or variable domain itself at or near position 12 of the FR1 region in such a way that it is no longer able to function as a binding site for other light chains.

Thus, a fourteenth aspect of the invention provides a non-naturally occurring antibody, or antigen-binding fragment, fusion or derivative thereof comprising a light chain variable domain, or a fusion of a said fragment or derivative, wherein the FR1 region of the light chain variable domain is modified (e.g. mutated) so as to inhibit, at least in part, the ability of the antibody, fragment, fusion or derivative to form aggregates.

In the above aspect of the invention the antibody or antigen-binding fragment, fusion or derivative thereof comprising a light chain variable domain wherein the FR1 domain is modified can be part of a fusion protein, e.g. wherein the fusion partner is a further antibody or antigen-binding fragment, fusion or derivative thereof comprising a light chain variable domain which extends serum half life, e.g. by binding to serum albumin.

In the above aspect of the invention the light chain variable domain can for example be modified at one or more of amino acid positions 8-22 (assigned using the Kabat system).

Preferably the immunoglobulin variable domain or antibody specifically binds a target which may be any biological substance capable of binding to a heterospecific polypeptide. Targets may be, for example, proteins, peptides, nucleic acids, oligonucleic acids, saccharides, polysaccharides, glycoproteins. Examples include, but are not limited to therapeutic targets, diagnostic targets, receptors, receptor ligands, viral coat proteins, immune system proteins, hormones, enzymes, antigens, cell signalling proteins, or a fragment thereof. Targets may be native protein or a fragment thereof, a homologous sequence thereof, a functional portion thereof, or a functional portion of an homologous sequence. Targets include but are not limited to IgE, Tumor necrosis factor alpha (TNF-alpha), von Willebrand Factor (vWF), vWF A1 or A3 5 domains, gplb, gpla/11A, collagen or a fragment thereof, or a fragment of a homologous sequence thereof, interferon gamma (IFN-gamma), amyloid-beta (A-beta) or fragment thereof, transferrin receptor specific ligand-neuropharmaceutical agent fusion proteins (see U.S. Pat. No. 5,977,307, the teachings of which are incorporated herein by reference), brain capillary endothelial cell receptor, transferrin, transferrin receptor (e.g., soluble transferrin receptor), insulin, insulin-like growth factor 1 (IGF 1) receptor, insulin-like growth factor 2 (IGF 2) receptor, insulin receptor, blood coagulation factor X, α1-antitrypsin and HNF 1α. Suitable polypeptides that enhance serum half-life also include alpha-1 glycoprotein (orosomucoid; AAG), alpha-1 antichymotrypsin (ACT), alpha-1 microglobulin (protein HC; AIM), antithrombin III (AT III), apolipoprotein A-1 (Apo A-1), apolipoprotein B (Apo B), ceruloplasmin (Cp), complement component C3 (C3), complement component C4 (C4), C1 esterase inhibitor (C1 INH), C-reactive protein (CRP), ferritin (FER), hemopexin (HPX), lipoprotein(a) (Lp(a)), mannose-binding protein (MBP), myoglobin (Myo), prealbumin (transthyretin; PAL), retinol-binding protein (RBP), and rheumatoid factor (RF) collagens, laminins, integrins and fibronectin, plasma proteins (e.g., fibrin, α-2 macroglobulin, serum albumin, fibrinogen (e.g., fibrinogen A, fibrinogen B), serum amyloid protein A, haptoglobin, profilin, ubiquitin, uteroglobulin and α-2-microglobulin), enzymes and enzyme inhibitors (e.g., plasminogen, lysozyme, cystatin C, alpha-1-antitrypsin and pancreatic trypsin inhibitor), proteins of the immune system, such as immunoglobulin proteins (e.g., IgA, IgD, IgE, IgG, IgM, immunoglobulin light chains (kappa/lambda)), transport proteins (e.g., retinol binding protein, α-1 microglobulin), defensins (e.g., beta-defensin 1, neutrophil defensin 1, neutrophil defensin 2 and neutrophil defensin 3) and the like, proteins found at the blood brain barrier or in neural tissue include, for example, melanocortin receptor, myelin, ascorbate transporter and the like, proteins localized to the kidney (e.g., polycystin, type IV collagen, organic anion transporter K1, Heymann's antigen), proteins localized to the liver (e.g., alcohol dehydrogenase, G250), proteins localized to the lung (e.g., secretory component, which binds IgA), proteins localized to the heart (e.g., HSP 27, which is associated with dilated cardiomyopathy), proteins localized to the skin (e.g., keratin), bone specific proteins such as morphogenic proteins (BMPs), which are a subset of the transforming growth factor β superfamily of proteins that demonstrate osteogenic activity (e.g., BMP-2, BMP-4, BMP-5, BMP-6, BMP-7, BMP-8), tumor specific proteins (e.g., trophoblast antigen, herceptin receptor, oestrogen receptor, cathepsins (e.g., cathepsin B, which can be found in liver and spleen)), disease-specific proteins include, for example, antigens expressed only on activated T-cells, including LAG-3 (lymphocyte activation gene), osteoprotegerin ligand (OPGL; see Nature 402, 304-309 (1999)), OX40 (a member of the TNF receptor family, expressed on activated T cells and specifically up-regulated in human T cell leukemia virus type-I (HTLV-I)-producing cells; see Immunol. 165(1):263-70 (2000)), metalloproteases (associated with arthritis/cancers) including CG6512 *Drosophila*, human paraplegin, human FtsH, human AFG3L2, murine ftsh; and angiogenic growth factors, including acidic fibroblast growth factor (FGF-1), basic fibroblast growth factor (FGF-2), vascular endothelial growth factor/vascular permeability factor (VEGF/VPF), transforming growth factor-α (TGF-α), tumor necrosis factor-alpha (TNF-α), angiogenin, interleukin-3 (IL-3), interleukin-8 (IL-8), platelet-derived endothelial growth factor (PD-ECGF), placental growth factor (P1GF), midkine platelet-derived growth factor-BB (PDGF), and fractalkine, stress proteins such as heat shock proteins (HSPs). HSPs are normally found intracellularly. When they are found extracellularly, it is an indicator that a cell has died and spilled out its contents. This unprogrammed cell death (necrosis) occurs when as a result of trauma, disease or injury, extracellular HSPs trigger a response from the immune system. Binding to extracellular HSP can result in localizing the compositions of the invention to a disease site, proteins involved in Fc transport include, for example, Brambell receptor (also known as FcRB). This Fc receptor has two functions, both of which are potentially useful for delivery. The functions are (1) transport of IgG from mother to child across the placenta (2) protection of IgG from degradation thereby prolonging its serum half-life. It is thought that the receptor recycles IgG from endosomes. (See, Holliger et al., Nat Biotechnol 15(7):632-6 (1997).), cell surface protein, such as a CD antigen, cytokine receptor (e.g., interleukin receptor, chemokine receptor), adhesion molecule or costimulatory molecule. For example, the polypeptide drug can bind a cytokine, growth factors, cytokine receptor, growth factor receptor and other target ligand, which include but are not limited to: ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAP-alpha, FGF-acidic, FGF-basic, fibroblast growth factor-10, FLT3 ligand, Fractalkine (CX3C), GDNF, G-CSF, GM-CSF, GF-β1, human serum albumin, insulin, IGF-I, IGF-II, IL-1α, IL-1β, IL-1 receptor, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, MDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3 and HER 4, TACE recognition site, TNF BP-I and TNF BP-II, also hormones including pituitary hormone (PTH), adrenocorticotropic hormone (ACTH), renin, luteinizing hormone-releasing hormone (LHRH), gonadotropin-releasing hormone (GnRH), luteinizing hormone (LH), follicle stimulating hormone (FSH), aldosterone, and the like. Suitable drugs also include keratinocyte growth factor, interferons (e.g., IFN-α, IFN-β, IFN-gamma, IFN-omega), erythropoietin (EPO), proteases, elastases, LHRH analogs, agonists and antagonists, opioid receptor agonists, such as kappa opioid receptor agonists (e.g., dynorphin A), calcitonin and calcitonin analogs, antidiuretic hormone (vasopressin), oxytocin antagonists, vasoactive intestinal peptide, thrombin inhibitors, surfactants and snail venom (e.g., ziconotide), as well as any target disclosed in Table 5 or Table 6 hereto, whether in combination as set forth in the Annexes, in a different combination or individually. It will be appreciated that this list is by no means exhaustive.

In a preferred embodiment of the fourteenth aspect of the invention, the light chain variable domain is modified at one or more of amino acid positions 9, 10, 11, 12, 13 or 14 (assigned using the Kabat system). For example, the naturally occurring amino acid at one or more of positions 9, 10, 11, 12, 13 or 14 of the FR1 region of the light chain variable domain may be replaced with an amino acid which inhibit the ability of the polypeptide backbone within the FR1 region of the variable domain to form H-bonds, for example with other light chain variable domains.

Preferably, the naturally occurring amino acid at one or more of positions 9, 10, 11, 12, 13 or 14 of the FR1 region of the light chain variable domain is replaced with an amino acid selected from the group consisting of proline, tryptophan, phenylalanine, tyrosine.

More preferably, the naturally occurring amino acid at one or more of positions 9, 10, 11, 12, 13 or 14 of the FR1 region of the light chain variable domain is replaced with proline.

Most preferably, the light chain variable domain is modified at position 12 of the FR1 region, for example by replacing the naturally occurring amino acid (typically, serine in κ light chains) with proline. Thus, a preferred mutation is S12P.

It will be appreciated by persons skilled in the art that the modifications made to the FR1 region can also be made by other means, for example by substituting one or more of the amino acids by an unnatural amino acid, or mimetic. Further, the FRI region may be modified by chemical means or the addition of a large compound that hindered the binding or association such as the use of a PEG group.

It will be appreciated by persons skilled in the art that the antibody, fragment, fusion or derivative of the fourteenth aspect of the invention may comprise of consist of chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

Likewise, it will be appreciated that the antigen-binding fragment comprising a light chain variable domain may be selected from the group consisting of Fv fragments (e.g. single chain Fv and disulphide-bonded Fv), Fab-like fragments (e.g. Fab fragments, Fab' fragments and F(ab)$_2$ fragments), single variable domains (domain antibodies; dAbs, e.g. $V_H$, $V_{HH}$ and $V_L$ domains) in monomer and dual specific formats [e.g. dAb-linker-dAb]), and modified versions of the same (e.g. modified by the covalent attachment of polyethylene glycol or other suitable polymer).

Preferably, the antigen-binding fragment is a domain antibody (in either single chain or multimeric format).

Thus, in one embodiment, Vκ multimers (homo-oligomers, such as dimers and trimers) may be provided in which the FR1 region of one or more of the constituent Vκ subunits is modified (e.g. at amino acid position 9, 10, 11, 12 and/or 13) so as to inhibit, at least in part, the ability of the Vκ multimer to form aggregates. Such modifications may allow purification to be achieved more easily and/or lead to improved solubility properties. For example, a Vκ multimer may be provided incorporating an S12P mutation in all but one of the domain antibody chains in the multimeric format, or alternatively by incorporating an S9L and/or S10P mutation in one or more of the domain antibody chains in the multimeric format.

In a further preferred embodiment, the antibody, fragment, fusion or derivative of the fourteenth aspect of the invention may comprise a cytotoxic or detectable moiety. For example, the antibody, fragment, fusion or derivative may comprise a radioactive or fluorescent moiety.

As used herein, the terms 'cytotoxic' and 'detectable' moieties refer to single atoms and molecules that are either directly or indirectly involved in the production of a cytotoxic or detectable species, respectively. Such moieties can be linked to or incorporated in an antibody, fragment, fusion or derivative of the present invention, or used separately, and those atoms or molecules can be used alone or in conjunction with additional reagents. Suitable cytotoxic or detectable moieties are well known in medicinal chemistry and the linking of these moieties to polypeptides and proteins is well known in the art. Examples of cytotoxic or detectable moieties include, but are not limited to, the following: radioisotopes (e.g. $^3H$, $^{14}C$, $^{35}S$, $^{123}I$, $^{125}I$, $^{131}I$, $^{99}Tc$, $^{111}In$, $^{90}Y$, $^{188}Re$), radionuclides (e.g. $^{11}C$, $^{18}F$, $^{64}Cu$), fluorescent labels (e.g. FITC, rhodamine, lanthanide phosphors, carbocyanine), enzymatic labels (e.g. horseradish peroxidase, β-galactosidase, luciferase, alkaline phosphatase), chemiluminescent, biotinyl groups, predetermined polypeptide epitopes recognised by a secondary reporter (e.g. leucine zipper pair sequences, binding sites for secondary antibodies, metal binding domains, epitope tags). In some embodiments, labels are attached by spacer arms of various lengths to reduce potential steric hindrance.

The present invention also provides means for producing an antibody, fragment, fusion or derivative of the fourteenth aspect of the invention.

Thus, further aspects of the invention provide:
(a) an isolated nucleic acid molecule (e.g. a DNA molecule) encoding an antibody, fragment, fusion or derivative of the fourteenth aspect of the invention;
(b) a vector (e.g. an expression vector) comprising such a nucleic acid molecule; and
(c) a host cell comprising such a nucleic acid molecule or vector.

Exemplary and preferred vectors and host cells are described above in relation to the second aspect of the invention.

A further aspect of the invention provides a method for making an antibody, fragment, fusion or derivative of the fourteenth aspect of the invention, the method comprising culturing a host cell which expresses the antibody, fragment, fusion or derivative, and isolating the polypeptide therefrom.

Methods of generating antibodies and antibody fragments are well known in the art. For example, antibodies may be generated via any one of several methods which employ induction of in vivo production of antibody molecules, screening of immunoglobulin libraries (Orlandi. et al, 1989. *Proc. Natl. Acad. Sci. U.S.A.* 86:3833-3837; Winter et al., 1991, *Nature* 349:293-299) or generation of monoclonal antibody molecules by cell lines in culture. These include, but are not limited to, the hybridoma technique, the human B-cell hybridoma technique, and the Epstein-Barr virus (EBV)-hybridoma technique (Kohler et al., 1975. *Nature* 256:4950497; Kozbor et al., 1985. *J. Immunol. Methods* 81:31-42; Cote et al., 1983. *Proc. Natl. Acad. Sci. USA* 80:2026-2030; Cole et al., 1984. *Mol. Cell. Biol.* 62:109-120).

Suitable monoclonal antibodies to selected antigens may be prepared by known techniques, for example those disclosed in "*Monoclonal Antibodies. A manual of techniques*", H Zola (CRC Press, 1988) and in "*Monoclonal Hybridoma Antibodies. Techniques and Applications*", J G R Hurrell (CRC Press, 1982).

Antibody fragments can be obtained using methods well known in the art (see, for example, Harlow & Lane, 1988, "*Antibodies: A Laboratory Manual*", Cold Spring Harbor Laboratory, New York). For example, antibody fragments according to the present invention can be prepared by proteolytic hydrolysis of the antibody or by expression in *E. coli* or mammalian cells (e.g. Chinese hamster ovary cell culture or other protein expression systems) of DNA encoding the fragment. Alternatively, antibody fragments can be obtained by pepsin or papain digestion of whole antibodies by conventional methods.

It will be appreciated by persons skilled in the art that for human therapy or diagnostics, humanised antibodies are preferably used. Humanised forms of non-human (e.g. murine) antibodies are genetically engineered chimaeric antibodies or antibody fragments having preferably minimal-portions derived from non-human antibodies. Humanised antibodies include antibodies in which complementary determining regions of a human antibody (recipient antibody) are replaced by residues from a complementary determining region of a non-human species (donor antibody) such as mouse, rat of rabbit having the desired functionality. In some instances, Fv framework residues of the human antibody are replaced by corresponding non-human residues. Humanised antibodies may also comprise residues which are found neither in the recipient antibody nor in the imported complementarity-determining region or framework sequences. In general, the humanised antibody will comprise substantially all of at least one, two or typically four variable domains, in which all or substantially all of the complementarity determining regions correspond to those of a non-human antibody and all, or substantially all, of the framework regions correspond to those of a relevant human consensus sequence. Humanised antibodies optimally also include at least a portion of an antibody constant region, such as an Fc region, typically derived from a human antibody (see, for example, Jones et al., 1986. *Nature* 321:522-525; Riechmann et al., 1988, *Nature* 332:323-329; Presta, 1992, *Curr. Op. Struct. Biol.* 2:593-596).

Methods for humanising non-human antibodies are well known in the art. Generally, the humanised antibody has one or more amino acid residues introduced into it from a source which is non-human. These non-human amino acid residues, often referred to as imported residues, are typically taken from an imported variable domain. Humanisation can be essentially performed as described (see, for example, Jones et al., 1986, *Nature* 321:522-525; Reichmann et al., 1988. *Nature* 332:323-327; Verhoeyen et al., 1988, *Science* 239:1534-15361; U.S. Pat. No. 4,816,567) by substituting human complementarity determining regions with corresponding rodent complementarity determining regions. Accordingly, such humanised antibodies are chimaeric antibodies, wherein substantially less than an intact human variable domain has been substituted by the corresponding sequence from a non-human species. In practice, humanised antibodies may be typically human antibodies in which some complementarity determining region residues and possibly some framework residues are substituted by residues from analogous sites in rodent antibodies.

Human antibodies can also be identified using various techniques known in the art, including phage display libraries (see, for example, Hoogenboom & Winter, 1991, *J. Mol. Biol.* 227:381; Marks et al., 1991, *J. Mol. Biol.* 222:581; Cole et al., 1985, In: *Monoclonal antibodies and Cancer Therapy*, Alan R. Liss, pp. 77; Boerner et al., 1991. *J. Immunol.* 147:86-95).

A further aspect of the invention provides a pharmaceutical formulation comprising an antibody, fragment, fusion or derivative of the fourteenth aspect of the invention in admixture with a pharmaceutically or veterinarily acceptable excipient, diluent or carrier. Exemplary and preferred pharmaceutical formulations are described above in relation to the seventh aspect of the invention.

A still further aspect of the invention provides an antibody, fragment, fusion or derivative of the fourteenth aspect of the invention or a pharmaceutical formulation thereof for use in medicine. It will be appreciated by skilled persons that any known antibody-based therapeutic agent may be modified in accordance with the teachings herein to inhibit, at least in part, immunoglobulin light chain aggregation.

The present invention further provides a method of improving the solubility (in aqueous solution) of an antibody, or antigen-binding fragment, fusion or derivative thereof comprising a light chain variable domain, or a fusion of a said fragment or derivative, the method comprising modifying (e.g. mutating) the light FR1 region of the light chain variable domain so as to inhibit, at least in part, its ability to form aggregates.

In a preferred embodiment, the light chain variable domain is modified at one or more of amino acid positions 9, 10, 11, 12, 13 or 14 (assigned using the Kabat system). For example, the naturally occurring amino acid at one or more of positions 9, 10, 11, 12, 13 or 14 of the FR1 region of the light chain variable domain may be replaced with an amino acid which inhibit the ability of the polypeptide backbone within the FR1 region of the variable domain to form H-bonds, for example with other light chain variable domains.

Preferably, the naturally occurring amino acid at one or more of positions 9, 10, 11, 12, 13 or 14 of the FR1 region of the light chain variable domain is replaced with an amino acid selected from the group consisting of proline, tryptophan, phenylalanine, tyrosine. More preferably, the naturally occurring amino acid at one or more of positions 9, 10, 11, 12, 13 or 14 of the FR1 region of the light chain variable domain is replaced with proline. Most preferably, the light chain variable domain is modified at position 12 of the FR1 region, for example by replacing the naturally occurring amino acid (typically, serine in κ light chains) with proline.

The present invention further provides a method of improving the solubility (in aqueous solution) of an antibody, or antigen-binding fragment, fusion or derivative thereof comprising a heavy chain $C_H1$ domain, or a fusion of a said fragment or derivative, the method comprising modifying (e.g. mutating) the $C_H1$ domain so as to inhibit, at least in part, its ability to form aggregates.

In a preferred embodiment, the $C_H1$ domain is modified at one or more of amino acid positions 205 to 218. More preferably the $C_H1$ domain is modified at one or more of positions 212, 214 or 216.

Methods for measuring the solubility of a polypeptide are well known in the art and include following absorbance due to scatter at a wavelength at which the protein does not absorb, e.g. 410 nm, removing sample to run on gels and quantifying, removing samples to analyse by SEC (size exclusion chromatography), analysis by EM and analysis by analytical centrifugation.

Preferably, the solubility of the antibody, or antigen-binding fragment, fusion or derivative is improved by at least 10%, for example at least 20%, 30%, 40%, 50%, 75%, 100%, or more.

It will be appreciated by persons skilled in the art that the above methods may be used to improve the solubility of an antibody, fragment, fusion or derivative of selected from the group consisting of chimaeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

Likewise, it will be appreciated that the antigen-binding fragment comprising a light chain variable domain may be selected from the group consisting of Fv fragments (e.g. single chain Fv and disulphide-bonded Fv), Fab-like fragments (e.g. Fab fragments, Fab' fragments and F(ab)$_2$ fragments), single variable domains (i.e. domain antibodies; dAbs, e.g. $V_H$, $V_{HH}$ and $V_L$ domains) in monomer and dual formats [e.g. dAb-linker-dAb]), and modified versions of the same (e.g. modified by the covalent attachment of polyethylene glycol or other suitable polymer). dAbs can be human, Camelid, murine, or from Nurse shark.

Preferably, the antigen-binding fragment is a domain antibody.

Preferred aspects of the invention are described in the following non-limiting examples, with reference to the following figures:

FIG. 1. Immunoglobulin structure. (A) Schematic diagram of the basic structure of an IgG molecule showing the constituent heavy and light chains and domains therein. (B) Schematic diagram of an immunoglobulin light chain variable domain showing the framework and hypervariable (CDR) sequences therein.

Figure 2:
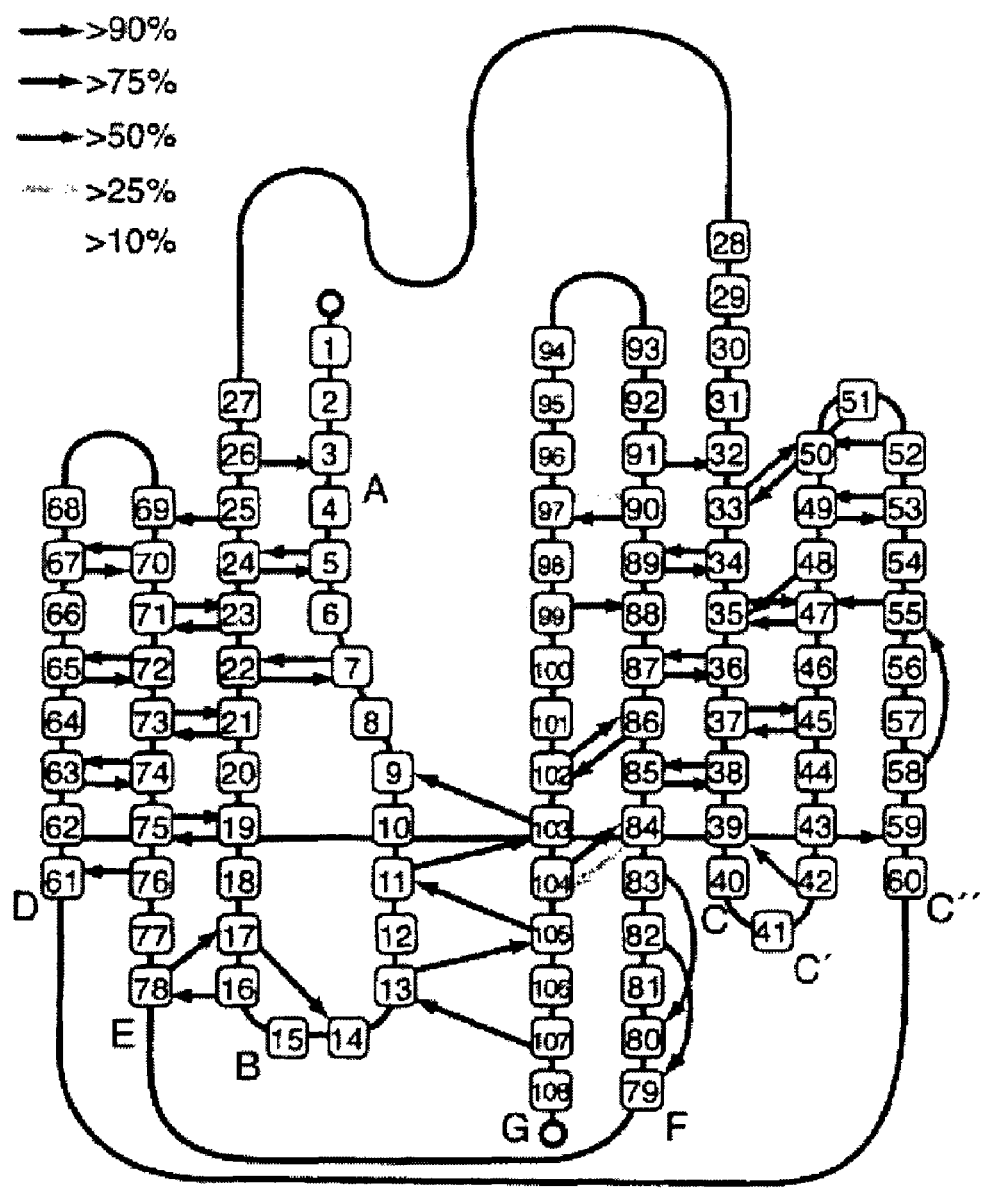

FIG. 2. Schematic diagram of the Vκ domain. Main-chain hydrogen bonds are marked according to their conservation amongst Vκ sequences. The strand switch in strand A can be seen, in which residues 3-7 make hydrogen bonds with strand B and residues 9-13 with strand G.

Figure 3:
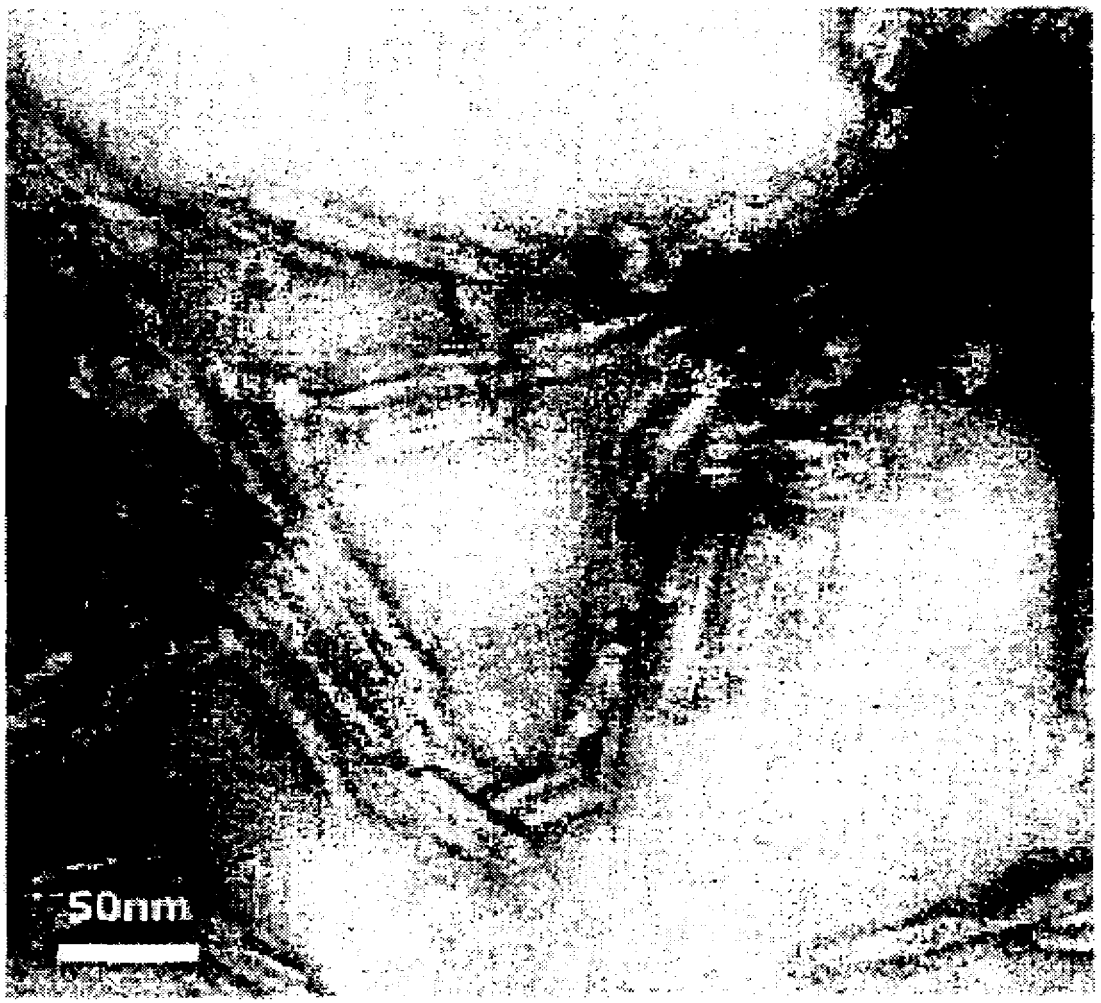

FIG. 3. Electron Micrograph of VD9 fibrils. Aggregates were observed of amyloid-like fibrils with individual fibril dimensions, ~7 nm wide and 60-180 nm long.

Figure 4:
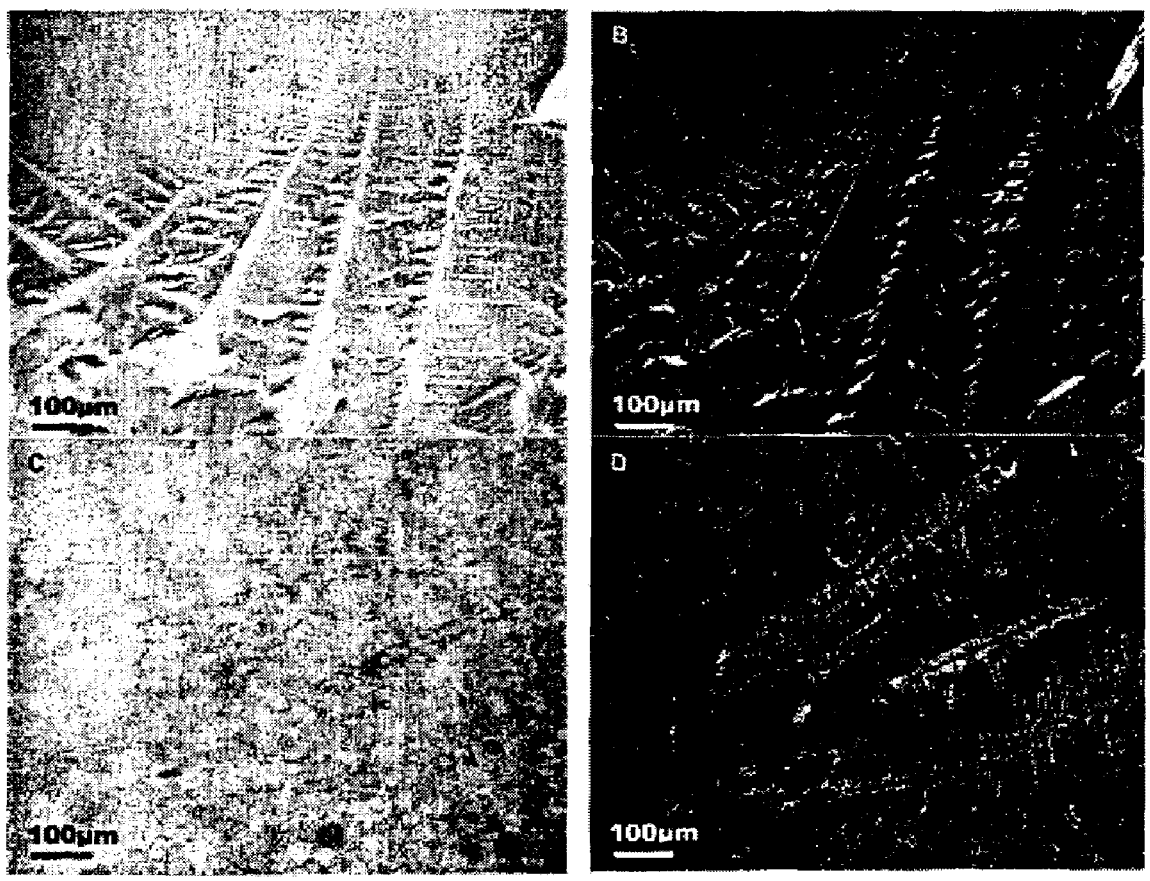

FIG. 4. Comparison of Congo red stained VD9 fibres (A, B) and control ex vivo AA amyloid fibrils (B, D). Images were taken in linear polarised white light (A, C) and cross-polarised light (circular polariser vibration direction ↕N-S; B, D), captured under identical light and colour settings. The VD9 aggregates are stained with Congo red but only a fraction exhibit apple-green dichroism (B). The semi-crystalline appearance of the dried suspensions is produced by the buffer salts and does not affect the Congo red results.

Figure 5:
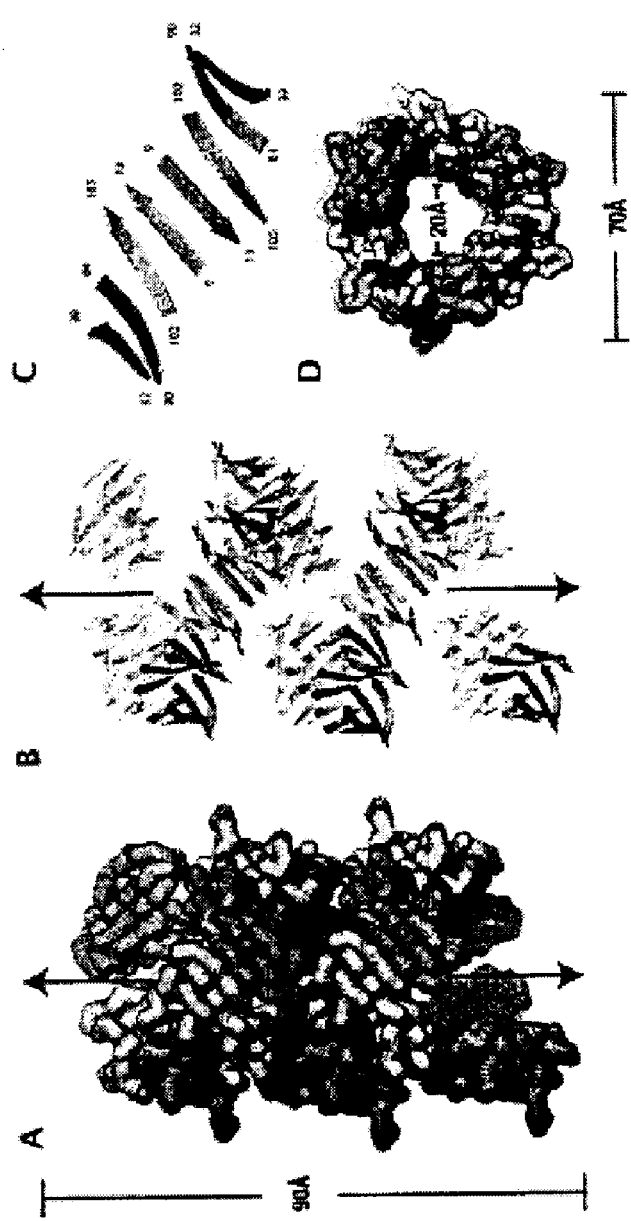

FIG. 5. Pentadecameric VD9 fibre structure. VD9 assembles into a repeating 15-molecule fibre of natively structured monomers. (A) Ribbon representation of the asymmetric unit with each coloured object (orange or wheat) representing a single VD9 domain. The asymmetric unit is packed end to end to create a continuous left-handed helical fibre. (B) β-strands pack predominantly at 45° with respect to the fibre axis. (C) Inter-subunit interactions create extended β-sheets across anti-parallel packed monomers. (D) VD9 fibre has a hollow core enclosed by six domains.

Figure 6:
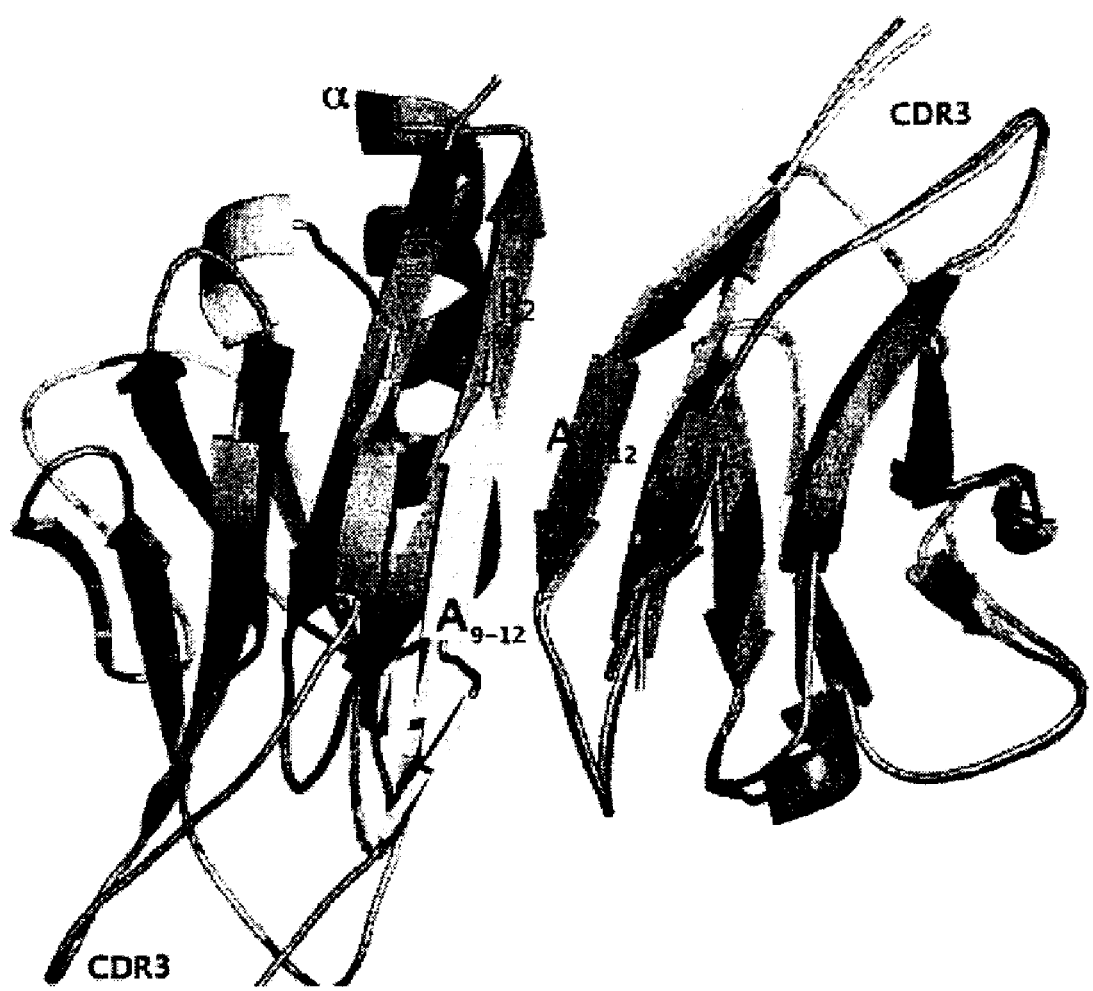

FIG. 6. Protein L:Fab complex superposed on two consecutive domains from the VD9 structure. Protein L (PpL; from P. magnus, PDB code 1HEZ(28)) complex is in orange, VD9 is in wheat. The orientation of each domain in the two structures is very similar, such that the sheet from PpL broadly matches the inner sheet of the first VD9 domain.

FIGS. 7-7d. Amino acid sequences and nucleic acid sequences of the disclosure.

EXAMPLES

Example 1

Summary

Exposed β-strands are a potential source of fold-instability as they can mediate non-specific β-zipper interactions, which in turn leads to oligomerisation and aggregation. To avoid this, β-sheet proteins have evolved a suite of "negative design" features which prevent unwanted edge interaction (1, 2). Historically, much of the focus on protein aggregation has been on partially unfolded intermediates. However, the pervasiveness of present-day topologies such as sandwiches, barrels and propellers and their constituent negative design elements implies that aggregation of native structure is a significant problem for all organisms (1).

Antibody immunoglobulin variable domains are among the most intensively studied of β-protein structures. Their domain architecture is highly conserved, containing several classic "negative design" features, yet certain light chain subsets have a propensity to aggregate both in vitro and in vivo, where they are associated with clinically important disorders: light chain deposition disease (LCDD) (3, 4). The κ sub-type is particularly prone to aggregation and is responsible for >85% of cases of LCDD (5), despite the fact that it is typically more stable than Vλ (6). There have been many studies on antibody domains in vitro showing that prolonged incubation under conditions of extreme pH and temperature can lead to partial unfolding and aggregation (7). Conversely, much less is known regarding the aggregation of native structural elements. Recently, we demonstrated that a single point-mutation in the $V_H V_L$ interface of a $V_H$ domain increases surface hydrophilicity and as a result both solubility and aggregation-resistance (8). Given the high stability of Vκ's, we wondered whether properties of the native state cause aggregation and pathogenic deposition in vivo.

Vκ domains have a typical immunoglobulin fold consisting of two anti-parallel β-sheets closely packed to produce a flattened β-barrel (FIG. 2). One end of the barrel is formed by variable loop CDR2 which twists in an S shape to cap both strand C' on the 5-strand inner sheet and strand D on the 3-strand outer sheet. At the other end of the barrel, the N-terminal strand A employs a "sheet switch" device to protect the two edge strands from each sheet (B on the outer-sheet and G on the inner; FIG. 2). Strand A initially pairs with B until an absolutely conserved cis-proline at position 8 introduces an abrupt kink that switches the strand to the opposite sheet where it packs against strand G. Before the kink, the end of variable loop CDR3 and the beginning of FR4 protects strand $A_{4-7}$, but post-kink the backbone of $A_{9-12}$ is unprotected. We discovered that strand $A_{9-12}$ causes oligomerisation and aggregation of Vκ VD9 in solution.

In these examples it is shown the strand switch leaves the FR1 β-strand ($A_{9-12}$) of Vκ light-chains structurally exposed and prone to aggregation. We present the crystal structure of an aggregation-prone Vκ1, VD9, in which $A_{9-12}$ β-zipper interactions mediate the assembly of a repeating pentadecameric helical fibre. Disruption of this interaction either by point mutation or a competing 5-mer peptide inhibits aggregation of VD9 in solution and dramatically increases its solubility. The bacterial superantigen Protein L binds to the same $A_{9-12}$ residues but only in κ sub-types. This sub-type distinction is a characteristic of light-chain deposition disease, which in >85% of cases is κ mediated. Structural comparison of the κ and λ sub-types reveals that they have alternative, highly conserved, strand switch designs which in κ results in a longer and more exposed $A_{9-12}$ edge strand. We provide evidence that the $A_{9-12}$ β-edge is an Achilles heel in the Vκ scaffold, both for pathogen immune evasion and self-aggregation.

Materials and Methods

Protein expression and purification. Germline VD9 was subcloned into a pET12a vector and expressed in *E. coli* BL21(DE3)pLysS cells (Novagen, Merck Biosciences, Nottingham). Expression supernatant was passed through a 0.2 μm filter and VD9 purified on Protein L agarose (Sigma-Aldrich Co Ltd, Dorset). The protein was then dialysed into 20 mM Hepes pH 7.4 containing 0.15 M NaCl and further purified on Superdex G75 (Amersham Biosciences UK Ltd, Bucks). Mutant S12P which does not bind Protein L was purified by ion-exchange chromatography using a Hi-Trap SP column (Amersham Biosciences).

Fibre kinetics and inhibition assays. Fibres were grown in 200 μl reaction volumes containing 0.4 mM protein in 0.5 M citrate buffer at pH 4. Reactions were incubated at 37° C. in an Eppendorf Thermomixer with cycles of shaking at 1400 rpm for 10 s followed by rest for 50 s. Aliquots (10 μl) were taken at time intervals and added to 90 μl of 65 μM thioflavin T (ThT) in PBS. Fluorescence was measured at 25° C. on a Spectramax Gemini XS fluorescence plate reader, with excitation at 445 nm and emission at 484 nm (10 μm bandwidth). Fibres typically gave a fluorescent signal of 10,000 units compared to 50 for citrate buffer alone. For peptide inhibition and mutant assays, samples were incubated for 3 days at which time a signal of ≦5% wild-type VD9 was considered to be non-fibre forming. Peptides, synthesised by Southampton Polypeptides Ltd, were re-suspended in 10 mM HEPES pH 7.0 and dilutions (10 μl) added to ThT as described above.

Electron microscopy. VD9 fibres were prepared as above and adsorbed on glow discharged carbon coated copper grids (300 mesh; Agar Scientific, Essex). Grids were washed with deionised water and negatively stained with 2% uranyl acetate. Samples were examined using a Tecnai 12 transmission electron microscope (FEI UK Ltd, Cambridge) operating at 120 kV.

Congo red staining. Experiments were performed essentially as described (24). VD9 fibres were analysed in parallel with amyloid fibrils extracted from human AA, ALys and A$\beta_2$m amyloidotic tissues or formed in vitro from A$\beta_{1-42}$ peptide (F. Hoffmann-La Roche, Basel, Switzerland) and from the SH3 domain of the p85$\alpha$ subunit of bovine phosphatidylinositol 3'-kinase (PI3-SH3) (25), all of which gave typical red-green dichroism after staining with Congo red (although only slightly with the VD9 fibres). All experiments were repeated independently on at least 3 occasions.

SAP binding assay. Experiments were performed essentially as described (26). The binding to VD9 fibres was compared to known amyloid fibrils as described above. Control incubations were performed in the presence of 20 mM EDTA and background counts obtained in the absence of fibrils were subtracted from all results. Three separate experiments gave consistent results.

Circular dichroism. CD measurements of 5 μM VD9 in PBS at 25° C. and 85° C. were recorded at 235 nm. The unfolding curves were assumed to be two state and fitted as described (27) using a $\Delta C_p$ contribution of 12 cal per amino acid residue (28) to give Tm and $\Delta G_{N-U}$.

Structure determination. Crystals of VD9 were grown by vapour diffusion in 0.1 M citric acid pH 4.0, 2M NaCl and frozen at 100 K. Data were collected on a Rigaku rotating-anode X-ray source with a Mar345 image plate diffractometer. Data were indexed in MOSFLM and scaled in SCALA (29). A molecular replacement solution for 15 molecules was found in PHASER using the model 1HEZ (30). The initial model was refined in REFMAC to give a final $R_{factor}$ of 0.24 and an $R_{free}$ of 0.29 (see Table 3). This result represents the largest number of copies solved by the molecular replacement method.

Results and Discussion

VD9 could be crystallised under conditions similar to those sustaining fibre growth, and we solved the structure by X-ray crystallography (see Table 3 for details). The asymmetric unit or smallest repeating oligomer consists of 15 molecules assembled into a close-packed left-handed helix (FIG. 5A). These 15 molecule helical oligomers are themselves stacked end to end to create a continuous fibre. There are 6 VD9 molecules per turn, each rotated by 60°, to give a pitch of ~35 Å or 1 VD9 domain (FIG. 5D). All VD9 molecules are natively folded and pack anti-parallel down the helix such that adjacent copies are related by 2-fold rotational symmetry orthogonal to the fibre axis (FIGS. 5A, B). The centre of the fibre is hollow, comprising a water-filled nanotube of 20 Å diameter (FIG. 5D). The overall diameter of the fibre is approximately 70 Å, which is remarkably consistent with the diameter of fibres grown in solution and visualised by electron microscopy. The structure also has many morphological similarities with classic amyloid fibres. The water-filled nanotube at the centre and the six domains per turn are consistent with the 4-6 proto-filaments arranged around an electron lucent centre seen by electron microscopy in cross sections of embedded AL fibres (7). The structure consists almost exclusively of anti-parallel β-sheet and the sheets are zippered together by exposed edge strands (FIG. 5C).

The structure is stabilised at two interfaces. The first interface is formed by a 'herringbone'-style packing of six tyrosine residues from and adjacent to the CDR loops The second interface is formed by the association of anti-parallel FR1 β-edge strands from adjacent monomers to create an inter-molecular 8-stranded β-sheet. The FR1 strands interact through a classic β-zipper main chain hydrogen bond network, involving six bonds between residues 9-12 (SSLS) A similar interaction is seen in the crystal packing of Bence-Jones protein BRE (8) and in binding to the bacterial superantigen Protein L which recognises >60% of all human light-chains (9). Thus FR1 is both structurally and functionally exposed and a "hot-spot" for zipper interactions. There are further packing interactions behind the zipper, including the side chains of Val19 and Pro8 (which create a small hydrophobic core) and Thr20, and hydrogen bonds from Ser7 to Thr20 and Thr22. Together, these interactions create a large solvent-excluded interface of 790 Å.

The exposed $A_{9-12}$ β-edge interface is also found in the interaction of Vk domains with the *Peptostreptococcus magnus* protein, Protein L (PpL). Protein L is a mixed-$\alpha\beta$ protein, which binds human Vκ domains through β-zipper interaction with $A_{9-12}$. We superposed the light-chain from the solved Protein L:Fv complex with one of the molecules from the VD9 helix. Remarkably, this places the four β-strands of Protein L and the first four β-strands of the next VκD molecule in the helix in close alignment. Indeed Protein L and VD9 use an identical hydrogen bond network with the same $A_{9-12}$ residues (FIGS. 6A & B). The distances and angles of the hydrogen bonds deviate, respectively, by less than 0.2 Å and 6°. The only difference between them is that the VκD structure has an additional putative hydrogen bond, between the peptide oxygen of position 12 and nitrogen of position 9 (in the structurally equivalent position to position 9 in Protein L, strand $\beta_2$ position 835, the nitrogen is inward-pointing). Together, these results illustrate that $A_{9-12}$ is both structurally exposed and a hot-spot for functional interaction (39, 40).

To explore the role of the $A_{9-12}$ β-edge in aggregation, we tested the effect of mutating or protecting the interface. Firstly, a number of proline mutations were introduced into $A_{9-12}$ to disrupt β-zipper formation. Mutant S10P was still bound by Protein L and formed fibres whilst mutant S12P was neither bound by Protein L nor formed aggregates (Table 4). This single mutant S12P also gave a substantial increase in solubility and expression. These observations are entirely consistent with a role for the strand in mediating aggregation. Secondly, we tested whether addition of Protein L or "zipper" peptides inhibited self-aggregation. Tetrameric Protein L did inhibit fibrillogenesis of VD9, as detected by ThT fluorescence, but led to precipitation, presumably due to the multivalent interaction. However a synthetic "zipper" peptide, corresponding to the interacting strand of Protein L (PL: QTAEF), prevented fibrillogenesis (>10-fold molar excess PL peptide to 0.1 mM VD9). Addition of a "non-zipper" control peptide (H5:SSPSA), with a central proline to prevent "zipper" interactions, had no effect under similar conditions. We conclude that the $A_{9-12}$ zipper interaction is a nucleus for VD9 aggregation in solution.

The second interface in the crystal structure involves CDR residues from all three loops. The centre of this interface is formed by a herringbone-style packing of six tyrosine residues at positions 32, 49 and 92 on each molecule arranged in parallel allowing π-π or edge-to-plane stacking of the aromatic rings. The OH groups of tyrosines 32 and 92 are also orientated to allow hydrogen bonding with opposing asparagine and glutamine side-chains. In this way, Tyr32A interacts with Asn34B and Tyr92A with Gln55B. There are further interactions involving hydrophobic stacking of planar side-chains with the "herringbone" tyrosines, such as between Tyr92 and Asp49. In studies of model amyloid-forming peptides, hydrophobic residues, particularly aromatics, have been shown to strongly promote fibrillogenesis (41). In a recent structure of a 12-mer amyloidogenic peptide, Makin et al found that π-π stacking of phenylalanine side-chains was a key component of fibril assembly (42). Deret et al have also observed a higher frequency in amyloidogenic rather than non-amyloidogenic light chains (43). We made a series of alanine mutations at positions 32, 34, 55 and 92 to test the role of this interface in mediating aggregation in solution, but in contrast to mutation at $A_{9-12}$, only a limited effect was observed (Table 3). Although there is evidence that CDR loops can influence aggregation propensity in vivo and hence provide a potential aggregation interface (44), it seems that the effect here is small.

A predominant feature of the light chain deposits that characterise LCDD is that they are composed of Vκ rather than Vλ domain sub-types. We compared the strand switch between Vκ and Vλ domains to see if we could explain this propensity. The two domains are highly homologous and superpose with a framework r.m.s.d of <1 Å. However, they clearly differ in the design of their strand switch in FR1. Kappa domains accomplish strand switch through a cis-proline at position 8 (FIG. 2) but most λ chains have a trans-proline at this position with an additional trans-proline at position 9. The kink introduced by the two trans-prolines is not as acute as in κ, but sufficient to accomplish strand switching. The crucial difference between the two designs (single cis-proline in Vκ versus two trans-prolines in Vλ) is that the extra proline in Vκ at position 9 both shortens the $A_{9-12}$ strand to just three residues ($A_{10-12}$) and caps it through its planar ring. These changes should reduce the likelihood of zipper interactions of the strand in its native state and in folding intermediates. Trans-cis isomerisation is often the rate-limiting step in protein folding and the presence of a cis-proline in Vκ could slow its rate of folding, thus increasing the opportunity for off-pathway aggregation. Indeed the trans-cis isomerisation of prolines at residues 8 and 95 in Vκ have both been shown to be rate-limiting (45).

If the alternative strand switch sequence in λ chains makes it less susceptible to aggregation this raises the question of why the Vκ sequence is maintained—particularly, as we have shown, that a single point mutation is sufficient to prevent aggregation. A potential explanation can be derived from the in vitro evolution experiment conducted by Spada et al to determine the optimal light-chain strand switch sequence for thermodynamic stability (46). In their study, two libraries were made; one κ-like in which proline 8 and flanking residues were randomised, and one 1-like with a single residue deletion at position 7. When the libraries were combined and selected together, the Vκ sequence was rapidly enriched over its Vλ counterpart. Biophysical analysis of clones of each type revealed that this was because the Vκ sequence is considerably more stable. The authors also noted that, though more stable, the Vκ sequence is significantly more prone to aggregation during expression and produces more insoluble material.

A further hypothesis for the conservation of the Vκ strand switch is that it may influence pathogen recognition. It has long been known that polyclonal antibody responses are often more effective at neutralising antigens than individual constituent antibodies. The Vκ $A_{9-12}$ sequence could facilitate edge-edge interactions between antibodies of a polyclonal response, thereby increasing the avidity of the response. Calarese et al recently showed that variable domains can adopt unusual quaternary structures. In their case, an anti HIV-1 antibody underwent heavy chain domain exchange in order to bind a repetitive carbohydrate epitope (47).

Although β-edges have long been hypothesized to play a central role in protein aggregation, existing data is largely limited to partially unstructured proteins or peptides (42, 14). This is despite the fact that β-protein topology clearly illustrates the importance of protecting against native-state aggregation (10). Here we show, for the first time, that a flaw in the native-state of an aggregation-prone immunoglobulin κ light chain domain (a β-barrel fold) leaves a β-edge strand exposed for aggregation. Paradoxically, this same edge strand ($A_{9-12}$) forms part of a strand switch designed to protect one end of the immunoglobulin barrel. We propose that a crucial difference in the design of this strand switch between κ and λ sub-types explains why the aggregation of light-chains in vivo is largely confined to Vκ. Finally, conservation of the Vκ strand-switch, despite its susceptibility to aggregation, suggests that it may provide compensating advantages.

With a central role in self-aggregation and immune evasion by bacteria, FR1 is clearly an 'Achilles heel' within the light chain scaffold. It is therefore surprising that this sequence persists, especially as we show here that a single mutation is protective. Such a mutation does exist within the germline; κII has a proline at position 12 which prevents Protein L binding. Furthermore, κII appears to be more resistant to aggregation in vivo: clinical AL amyloidosis predominately involves sub-types I, III & IV (19, 20) whilst κII has been reported in only a single AL patient (21) and this particular monoclonal protein may well have contained other amyloidogenic substitution(s). One possible explanation for the conservation of FR1 is that it provides a selective advantage. For instance, FR1 interactions could allow antibodies from a polyclonal response to multimerise, significantly increasing affinity through avidity. Synergistic binding has been shown to monomeric antigens such as human chorionic gonadotropin (22) and botulinum toxin (23) where the combined affinity is considerably greater than the sum of the parts.

FR1 represents a novel interface for light chain aggregation and amyloid fibrillogenesis. In a general context, it demonstrates that protein aggregation can be mediated by natively structured exposed β-edges and that it is possible to block the formation of deposition disease using drugs that target the native state.

Example 2

Anti-EGFR dAb In-Line Fusions Containing an (S12P) Mutation

In line fusion proteins (ILFS) which comprise a domain antibody (dAb) which is an anti-EGFR dAb designated DOM16-39-618 (S12P) fused to an anti-serum albumin dAb designated a DOM7 dAb were constructed. DOM16-39-618 contains a Serine to Proline mutation at position 12. It was found that the presence of this mutation stopped binding of the in-line fusion protein to protein L and also prevented light chain aggregation. The portions of the fusions are listed in table 7 as they appear in the fusion proteins from amino terminus to carboxy terminus. Accordingly the structure of the fusion proteins can be appreciated by reading the table from left to right. The first fusion protein presented in the table has the structure from amino terminus to carboxy terminus, DOM16-39-618 (S12P)-Linker-DOM7H-14. The sequence information of these dAbs is disclosed in WO 2007/066106 and this disclosure is explicitly incorporated into the present disclosure by reference.

Example 3

Anti-TNF Alpha dAb in-Line Fusion Containing an (S12P) Mutation

An in line fusion protein which comprises a domain antibody (dAb) which is an anti-TNF alpha dAb designated PEP1-5-19(S12P)-fused to an anti-serum albumin dAb designated a DOM7h-8 dAb was constructed. PEP1-5-19 contains a Serine to Proline mutation at position 12.

This in line fusion is designated PEP1-5-19(S12P)-TVA-DOM7h-8

The individual dAbs are generated and modified individually before they are fused together by SOE-PCR.

SOE-PCR: Two DNA fragments are fused together by PCR without restriction digestion (splicing by overlapping extension PCR or SOE-PCR). 3' primer for each fragment is designed to overlap 3' sequences on the other fragment. PCR products of the two fragments are mixed in equimolar concentration and PCR-amplified using outer primers which results in the production of fusion DNA.

For amending the S12P mutation in the first dAbs, primer 1294 was used (sequence below) also appending a SAL1 restriction site. The linker sequence (starting from either only TVA to TVAA to TVAAPS; shown below) was used as linker between the dAbs. The sequence is the natural extension of a Vk to the Ck domain and only introduces one non-natural peptide bond minimising immunological issues of ILFs.

The in-line fusions were found to be well expressed (in *Pichia p.* in fermenter and shake flasks) and potency was good as assessed in biological cell assays (Table 8)

Example 4

Anti IL-1 dAb In-Line Fusions Containing an (S12P) Mutation

Six in line fusion proteins which comprise a domain antibody (dAb) which is an anti-IL-1 dAb (a DOM 4 dAb) fused to an anti-serum albumin dAb (a DOM7h dAb) were constructed as below. The Dom4 dAb contains a Serine to Proline mutation at position 12.

These anti IL-1 in line fusion are designated:
DOM4-130-54(S12P)-TVAAPS-DOM7h-8;
DOM4-130-54(S12P)-TVAAPS-DOM7h-2;
DOM4-130-54(S12P)-TVAAPS-DOM7h-10;
DOM4-130-93(S12P)-TVAAPS-DOM7h-8;
DOM4-130-54(S12P)-TVAAPS-DOM7h-22;
DOM4-130-54(S12P)-TVAAPS-DOM7h-31

The individual dAbs are generated and modified individually before they are fused together by SOE-PCR.

SOE-PCR: Two DNA fragments are fused together by PCR without restriction digestion (splicing by overlapping extension PCR or SOE-PCR). 3' primer for each fragment is designed to overlap 3' sequences on the other fragment. PCR products of the two fragments are mixed in equimolar concentration and PCR-amplified using outer primers which results in the production of fusion DNA.

For amending the S12P mutation in the first dAbs, primer 1294 was used (sequence below) also appending a SAL1 restriction site. The linker sequence (starting from either only TVA to TVAA to TVAAPS; shown below) was used as linker between the dAbs. The sequence is the natural extension of a Vk to the Ck domain and only introduces one non-natural peptide bond minimising immunological issues of ILFs.

The in-line fusions were well expressed (in Pichia p. in fermenter and shake flasks) and potency was good as assessed in biological cell assays (Table 9)

```
Primer 1294 sequence:
CACGCGTCGACGgatattcagatgactcagagcccaagcagcctgcccgcgtccgtcggtgat TVAAPS Linker sequence:
ACCGTCGCTGCTCCA
```

TABLE 2

Binding of $^{125}$I-SAP to VD9 and control amyloid fibrils

| Fibres | $A_{280}$-$A_{320}$ units/ml | % $^{125}$I-SAP counts bound |
|---|---|---|
| VD9 | 0.8 | 14 |
| VD9 | 0.6 | 9 |
| VD9 | 0.2 | 6 |
| VD9 | 0.09 | 4 |
| VD9 | 0.02 | 2 |
| VD9 + EDTA | 0.02 | 1 |
| PI-SH3** | 0.03 | 64 |
| PI-SH3 | 0.003 | 7 |
| PI-SH3 | 0.0003 | 2 |
| PI-SH3 + EDTA | 0.0003 | 0.1 |
| Aβ1-42** | 0.02 | 27 |
| Aβ1-42 | 0.002 | 2 |
| AA | 0.3 | 95 |
| AA | 0.06 | 86 |
| AA | 0.03 | 74 |
| AA | 0.01 | 51 |
| AA | 0.003 | 9 |
| AA + EDTA | 0.03 | 5 |
| Aβ$_2$M | 0.3 | 82 |
| Aβ$_2$M | 0.05 | 47 |
| Aβ$_2$M | 0.03 | 31 |
| Aβ$_2$M | 0.01 | 13 |
| Aβ$_2$M + EDTA | 0.03 | 2 |
| ALys | 0.2 | 79 |
| ALys | 0.05 | 72 |
| ALys | 0.02 | 45 |
| ALys | 0.002 | 7 |
| ALys + EDTA | 0.02 | 2 |

**Insufficient material was available to test at higher concentrations.

Results are expressed as a percentage of $^{125}$I-SAP counts bound, after correction for binding in the absence of fibrils (<1%). Each result is the mean of 2 replicates.

TABLE 3

Data collection and structure refinement statistics.

| | VD9 |
|---|---|
| Spacegroup | P6$_4$22 |
| Cell | a = b = 191.881, c = 197.3031 |
| Number per a.u. | 15 |
| Resolution | 2.6 Å |
| Unique reflections | 62,507 |

TABLE 3-continued

Data collection and structure refinement statistics.

|  | VD9 |
|---|---|
| $R_{merge}$ | 0.093 (0.421) |
| Redundancy | 2.3 (1.9) |
| Completeness (%) | 91.4 (89.7) |
| Average I/σI | 8.5 (1.9) |
| Final $R_{cryst}$ | 0.24 |
| Final $R_{free}$ | 0.29 |
| Bond r.m.s.d | 0.009 |
| Angle r.m.s.d | 1.5° |

Numbers in parentheses are for highest resolution shell.

TABLE 4

Summary of biophysical properties of VD9 and mutants

| Substitution | Expression | PpL Binding | Solubility ($A_{280}$ nm) | Aggregation 12 h | Aggregation 3 d |
|---|---|---|---|---|---|
| WT VD9 | + | strong | ~4 | + | + |
| S9L | −/+ | medium | ~7 | − | + |
| S10P | +++ | weak | ~6 | + | + |
| S12P | ++ | no | >25 | − | − |
| S9L/S12P | +++ | no | >10 | − | + |
| Y32A | ++ | strong | >10 | − | + |
| Y92A | + | strong | >8 | − | + |
| Y32A/Y92A | ++ | strong | >12 | − | + |
| N34D/Q55E | + | strong | >14 | − | + |
| Ala x 4 | + | strong | >14 | − | + |

Expression: '+' 1 mg/L, '++' ~5 mg/L, '+++' >10 mg/L
Aggregation: '+' refers to measurable light scattering at 410 nm.

TABLE 5

| Pairing | Therapeutic relevant references. |
|---|---|
| TNF ALPHA/TGF-β | TGF-β and TNF when injected into the ankle joint of collagen induced arthritis model significantly enhanced joint inflammation. In non-collagen challenged mice there was no effect. |
| TNF ALPHA/IL-1 | TNF and IL-1 synergize in the pathology of uveitis. TNF and IL-1 synergize in the pathology of malaria (hypoglycaemia, NO). TNF and IL-1 synergize in the induction of polymorphonuclear (PMN) cells migration in inflammation. IL-1 and TNF synergize to induce PMN infiltration into the peritoneum. IL-1 and TNF synergize to induce the secretion of IL-1 by endothelial cells. Important in inflammation. IL-1 or TNF alone induced some cellular infiltration into knee synovium. IL-1 induced PMNs, TNF - monocytes. Together they induced a more severe infiltration due to increased PMNs. Circulating myocardial depressant substance (present in sepsis) is low levels of IL-1 and TNFacting synergistically. |
| TNF ALPHA/IL-2 | Most relating to synergisitic activation of killer T-cells. |
| TNF ALPHA/IL-3 | Synergy of interleukin 3 and tumor necrosis factor alpha in stimulating clonal growth of acute myelogenous leukemia blasts is the result of induction of secondary hematopoietic cytokines by tumor necrosis factor alpha. Cancer Res. 1992 Apr. 15; 52(8): 2197-201. |
| TNF ALPHA/IL-4 | IL-4 and TNF synergize to induce VCAM expression on endothelial cells. Implied to have a role in asthma. Same for synovium - implicated in RA. TNF and IL-4 synergize to induce IL-6 expression in keratinocytes. Sustained elevated levels of VCAM-1 in cultured fibroblast-like synoviocytes can be achieved by TNF-alpha in combination with either IL-4 or IL-13 through increased mRNA stability. Am J Pathol. 1999 April; 154(4): 1149-58 |
| TNF ALPHA/IL-5 | Relationship between the tumor necrosis factor system and the serum interleukin-4, interleukin-5, interleukin-8, eosinophil cationic protein, and immunoglobulin E levels in the bronchial hyperreactivity of adults and their children. Allergy Asthma Proc. 2003 March-April; 24(2): 111-8. |
| TNF ALPHA/IL-6 | TNF and IL-6 are potent growth factors for OH-2, a novel human myeloma cell line. Eur J Haematol. 1994 July; 53(1): 31-7. |
| TNF ALPHA/IL-8 | TNF and IL-8 synergized with PMNs to activate platelets. Implicated in Acute Respiratory Distress Syndrome. See IL-5/TNF (asthma). Synergism between interleukin-8 and tumor necrosis factor-alpha for neutrophil-mediated platelet activation. Eur Cytokine Netw. 1994 September-October; 5(5): 455-60. (adult respiratory distress syndrome (ARDS)) |
| TNF ALPHA/IL-9 |  |
| TNF ALPHA/IL-10 | IL-10 induces and synergizes with TNF in the induction of HIV expression in chronically infected T-cells. |
| TNF ALPHA/IL-11 | Cytokines synergistically induce osteoclast differentiation: support by immortalized or normal calvarial cells. Am J Physiol Cell Physiol. 2002 September; 283(3): C679-87. (Bone loss) |
| TNF ALPHA/IL-12 |  |

TABLE 5-continued

| Pairing | Therapeutic relevant references. |
|---|---|
| TNF ALPHA/IL-13 | Sustained elevated levels of VCAM-1 in cultured fibroblast-like synoviocytes can be achieved by TNF-alpha in combination with either IL-4 or IL-13 through increased mRNA stability. Am J Pathol. 1999 April; 154(4): 1149-58.<br>Interleukin-13 and tumour necrosis factor-alpha synergistically induce eotaxin production in human nasal fibroblasts. Clin Exp Allergy. 2000 March; 30(3): 348-55.<br>Interleukin-13 and tumour necrosis factor-alpha synergistically induce eotaxin production in human nasal fibroblasts. Clin Exp Allergy. 2000 March; 30(3): 348-55 (allergic inflammation)<br>Implications of serum TNF-beta and IL-13 in the treatment response of childhood nephrotic syndrome. Cytokine. 2003 Feb. 7; 21(3): 155-9. |
| TNF ALPHA/IL-14 | Effects of inhaled tumour necrosis factor alpha in subjects with mild asthma. Thorax. 2002 September; 57(9): 774-8. |
| TNF ALPHA/IL-15 | Effects of inhaled tumour necrosis factor alpha in subjects with mild asthma. Thorax. 2002 September; 57(9): 774-8. |
| TNF ALPHA/IL-16 | Tumor necrosis factor-alpha-induced synthesis of interleukin-16 in airway epithelial cells: priming for serotonin stimulation. Am J Respir Cell Mol Biol. 2003 March; 28(3): 354-62. (airway inflammation)<br>Correlation of circulating interleukin 16 with proinflammatory cytokines in patients with rheumatoid arthritis. Rheumatology (Oxford). 2001 April; 40(4): 474-5. No abstract available.<br>Interleukin 16 is up-regulated in Crohn's disease and participates in TNBS colitis in mice. Gastroenterology. 2000 October; 119(4): 972-82. |
| TNF ALPHA/IL-17 | Inhibition of interleukin-17 prevents the development of arthritis in vaccinated mice challenged with *Borrelia burgdorferi*. Infect Immun. 2003 June; 71(6): 3437-42.<br>Interleukin 17 synergises with tumour necrosis factor alpha to induce cartilage destruction in vitro. Ann Rheum Dis. 2002 October; 61(10): 870-6.<br>A role of GM-CSF in the accumulation of neutrophils in the airways caused by IL-17 and TNF-alpha. Eur Respir J. 2003 March; 21(3): 387-93. (Airway inflammation)<br>Abstract Interleukin-1, tumor necrosis factor alpha, and interleukin-17 synergistically up-regulate nitric oxide and prostaglandin E2 production in explants of human osteoarthritic knee menisci. Arthritis Rheum. 2001 September; 44(9): 2078-83. |
| TNF ALPHA/IL-18 | Association of interleukin-18 expression with enhanced levels of both interleukin-1beta and tumor necrosis factor alpha in knee synovial tissue of patients with rheumatoid arthritis. Arthritis Rheum. 2003 February; 48(2): 339-47.<br>Abstract Elevated levels of interleukin-18 and tumor necrosis factor-alpha in serum of patients with type 2 diabetes mellitus: relationship with diabetic nephropathy. Metabolism. 2003 May; 52(5): 605-8. |
| TNF ALPHA/IL-19 | Abstract IL-19 induces production of IL-6 and TNF-alpha and results in cell apoptosis through TNF-alpha. J Immunol. 2002 Oct. 15; 169(8): 4288-97. |
| TNF ALPHA/IL-20 | Abstract Cytokines: IL-20 - a new effector in skin inflammation. Curr Biol. 2001 Jul. 10; 11(13): R531-4 |
| TNF ALPHA/Complement | Inflammation and coagulation: implications for the septic patient. Clin Infect Dis. 2003 May 15; 36(10): 1259-65. Epub 2003 May 08. Review. |
| TNF ALPHA/IFN-gamma | MHC induction in the brain.<br>Synergize in anti-viral response/IFÑ-gamma induction.<br>Neutrophil activation/respiratory burst.<br>Endothelial cell activation<br>Toxicities noted when patients treated with TNF/IFÑ-gamma as anti-viral therapy<br>Fractalkine expression by human astrocytes.<br>Many papers on inflammatory responses - i.e. LPS, also macrophage activation.<br>Anti-TNF and anti-IFÑ-gamma synergize to protect mice from lethal endotoxemia. |
| TGF- β/IL-1 | Prostaglndin synthesis by osteoblasts<br>IL-6 production by intestinal epithelial cells (inflammation model)<br>Stimulates IL-11 and IL-6 in lung fibroblasts (inflammation model)<br>IL-6 and IL-8 production in the retina |
| TGF- β/IL-6 | Chondrocarcoma proliferation |
| IL-1/IL-2 | B-cell activation<br>LAK cell activation<br>T-cell activation<br>IL-1 synergy with IL-2 in the generation of lymphokine activated killer cells is mediated by TNF-alpha and beta (lymphotoxin). Cytokine. 1992 November; 4(6): 479-87. |
| IL-1/IL-3 | |
| IL-1/IL-4 | B-cell activation<br>IL-4 induces IL-1 expression in endothelial cell activation. |
| IL-1/IL-5 | |

TABLE 5-continued

| Pairing | Therapeutic relevant references. |
|---|---|
| IL-1/IL-6 | B cell activation<br>T cell activation (can replace accessory cells)<br>IL-1 induces IL-6 expression<br>C3 and serum amyloid expression (acute phase response)<br>HIV expression<br>Cartilage collagen breakdown. |
| IL-1/IL-7 | IL-7 is requisite for IL-1-induced thymocyte proliferation. Involvement of IL-7 in the synergistic effects of granulocyte-macrophage colony-stimulating factor or tumor necrosis factor with IL-1. J Immunol. 1992 Jan. 1; 148(1): 99-105. |
| IL-1/IL-8 | |
| IL-1/IL-10 | |
| IL-1/IL-11 | Cytokines synergistically induce osteoclast differentiation: support by immortalized or normal calvarial cells. Am J Physiol Cell Physiol. 2002 September; 283(3): C679-87. (Bone loss) |
| IL-1/IL-16 | Correlation of circulating interleukin 16 with proinflammatory cytokines in patients with rheumatoid arthritis. Rheumatology (Oxford). 2001 April; 40(4): 474-5. No abstract available. |
| IL-1/IL-17 | Inhibition of interleukin-17 prevents the development of arthritis in vaccinated mice challenged with *Borrelia burgdorferi*. Infect Immun. 2003 June; 71(6): 3437-42.<br>Contribution of interleukin 17 to human cartilage degradation and synovial inflammation in osteoarthritis. Osteoarthritis Cartilage. 2002 October; 10(10): 799-807.<br>Abstract Interleukin-1, tumor necrosis factor alpha, and interleukin-17 synergistically up-regulate nitric oxide and prostaglandin E2 production in explants of human osteoarthritic knee menisci. Arthritis Rheum. 2001 September; 44(9): 2078-83. |
| IL-1/IL-18 | Association of interleukin-18 expression with enhanced levels of both interleukin-1beta and tumor necrosis factor alpha in knee synovial tissue of patients with rheumatoid arthritis. Arthritis Rheum. 2003 February; 48(2): 339-47. |
| IL-1/IFN-gamma | |
| IL-2/IL-3 | T-cell proliferation<br>B cell proliferation |
| IL-2/IL-4 | B-cell proliferation<br>T-cell proliferation<br>(selectively inducing activation of CD8 and NK lymphocytes)IL-2R beta agonist P1-30 acts in synergy with IL-2, IL-4, IL-9, and IL-15: biological and molecular effects. J Immunol. 2000 Oct. 15; 165(8): 4312-8. |
| IL-2/IL-5 | B-cell proliferation/Ig secretion<br>IL-5 induces IL-2 receptors on B-cells |
| IL-2/IL-6 | Development of cytotoxic T-cells |
| IL-2/IL-7 | |
| IL-2/IL-9 | See IL-2/IL-4 (NK-cells) |
| IL-2/IL-10 | B-cell activation |
| IL-2/IL-12 | IL-12 synergizes with IL-2 to induce lymphokine-activated cytotoxicity and perforin and granzyme gene expression in fresh human NK cells. Cell Immunol. 1995 Oct. 1; 165(1): 33-43. (T-cell activation) |
| IL-2/IL-15 | See IL-2/IL-4 (NK cells)<br>(T cell activation and proliferation) IL-15 and IL-2: a matter of life and death for T cells in vivo. Nat Med. 2001 January; 7(1): 114-8. |
| IL-2/IL-16 | Synergistic activation of CD4+ T cells by IL-16 and IL-2. J Immunol. 1998 Mar. 1; 160(5): 2115-20. |
| IL-2/IL-17 | Evidence for the early involvement of interleukin 17 in human and experimental renal allograft rejection. J Pathol. 2002 July; 197(3): 322-32. |
| IL-2/IL-18 | Interleukin 18 (IL-18) in synergy with IL-2 induces lethal lung injury in mice: a potential role for cytokines, chemokines, and natural killer cells in the pathogenesis of interstitial pneumonia. Blood. 2002 Feb. 15; 99(4): 1289-98. |
| IL-2/TGF-β | Control of CD4 effector fate: transforming growth factor beta 1 and interleukin 2 synergize to prevent apoptosis and promote effector expansion. J Exp Med. 1995 Sep. 1; 182(3): 699-709. |
| IL-2/IFN-gamma | Ig secretion by B-cells<br>IL-2 induces IFN-□ expression by T-cells |
| IL-2/IFN-α/β | None |
| IL-3/IL-4 | Synergize in mast cell growth<br>Synergistic effects of IL-4 and either GM-CSF or IL-3 on the induction of CD23 expression by human monocytes: regulatory effects of IFN-alpha and IFN-gamma. Cytokine. 1994 July; 6(4): 407-13. |
| IL-3/IL-5 | |
| IL-3/IL-6 | |
| IL-3/IFN-gamma | IL-4 and IFN-gamma synergistically increase total polymeric IgA receptor levels in human intestinal epithelial cells. Role of protein tyrosine kinases. J Immunol. 1996 Jun. 15; 156(12): 4807-14. |

TABLE 5-continued

| Pairing | Therapeutic relevant references. |
|---|---|
| IL-3/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun. 1; 170(11): 5359-66. (allergic inflammation) |
| IL-4/IL-2 | IL-4 synergistically enhances both IL-2- and IL-12-induced IFN-{gamma} expression in murine NK cells. Blood. 2003 Mar. 13 [Epub ahead of print] |
| IL-4/IL-5 | Enhanced mast cell histamine etc. secretion in response to IgE A Th2-like cytokine response is involved in bullous pemphigoid. the role of IL-4 and IL-5 in the pathogenesis of the disease. Int J Immunopathol Pharmacol. 1999 May-August; 12(2): 55-61. |
| IL-4/IL-6 | |
| IL-4/IL-10 | |
| IL-4/IL-11 | Synergistic interactions between interleukin-11 and interleukin-4 in support of proliferation of primitive hematopoietic progenitors of mice. Blood. 1991 Sep. 15; 78(6): 1448-51. |
| IL-4/IL-12 | Synergistic effects of IL-4 and IL-18 on IL-12-dependent IFN-gamma production by dendritic cells. J Immunol. 2000 Jan. 1; 164(1): 64-71. (increase Th1/Th2 differentiation) IL-4 synergistically enhances both IL-2- and IL-12-induced IFN-{gamma} expression in murine NK cells. Blood. 2003 Mar. 13 [Epub ahead of print] |
| IL-4/IL-13 | Abstract Interleukin-4 and interleukin-13 signaling connections maps. Science. 2003 Jun. 6; 300(5625): 1527-8. (allergy, asthma) Inhibition of the IL-4/IL-13 receptor system prevents allergic sensitization without affecting established allergy in a mouse model for allergic asthma. J Allergy Clin Immunol. 2003 June; 111(6): 1361-1369. |
| IL-4/IL-16 | (asthma) Interleukin (IL)-4/IL-9 and exogenous IL-16 induce IL-16 production by BEAS-2B cells, a bronchial epithelial cell line. Cell Immunol. 2001 Feb. 1; 207(2): 75-80 |
| IL-4/IL-17 | Interleukin (IL)-4 and IL-17 synergistically stimulate IL-6 secretion in human colonic myofibroblasts. Int J Mol Med. 2002 November; 10(5): 631-4. (Gut inflammation) |
| IL-4/IL-24 | IL-24 is expressed by rat and human macrophages. Immunobiology. 2002 July; 205(3): 321-34. |
| IL-4/IL-25 | Abstract New IL-17 family members promote Th1 or Th2 responses in the lung: in vivo function of the novel cytokine IL-25. J Immunol. 2002 Jul. 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan. 02. (allergic inflammation) |
| IL-4/IFN-gamma | Abstract Interleukin 4 induces interleukin 6 production by endothelial cells: synergy with interferon-gamma. Eur J Immunol. 1991 January; 21(1): 97-101. |
| IL-4/SCF | Regulation of human intestinal mast cells by stem cell factor and IL-4. Immunol Rev. 2001 February; 179: 57-60. Review. |
| IL-5/IL-3 | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun. 1; 170(11): 5359-66. (Allergic inflammation see abstract) |
| IL-5/IL-6 | |
| IL-5/IL-13 | Inhibition of allergic airways inflammation and airway hyperresponsiveness in mice by dexamethasone: role of eosinophils, IL-5, eotaxin, and IL-13. J Allergy Clin Immunol. 2003 May; 111(5): 1049-61. |
| IL-5/IL-17 | Interleukin-17 orchestrates the granulocyte influx into airways after allergen inhalation in a mouse model of allergic asthma. Am J Respir Cell Mol Biol. 2003 January; 28(1): 42-50. |
| IL-5/IL-25 | Abstract New IL-17 family members promote Th1 or Th2 responses in the lung: in vivo function of the novel cytokine IL-25. J Immunol. 2002 Jul. 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan. 02. (allergic inflammation) |
| IL-5/IFN-gamma | |
| IL-5/GM-CSF | Differential regulation of human eosinophil IL-3, IL-5, and GM-CSF receptor alpha-chain expression by cytokines: IL-3, IL-5, and GM-CSF down-regulate IL-5 receptor alpha expression with loss of IL-5 responsiveness, but up-regulate IL-3 receptor alpha expression. J Immunol. 2003 Jun. 1; 170(11): 5359-66. (Allergic inflammation) |
| IL-6/IL-10 | |
| IL-6/IL-11 | |
| IL-6/IL-16 | Interleukin-16 stimulates the expression and production of pro-inflammatory cytokines by human monocytes. Immunology. 2000 May; 100(1): 63-9. |

TABLE 5-continued

| Pairing | Therapeutic relevant references. |
|---|---|
| IL-6/IL-17 | Stimulation of airway mucin gene expression by interleukin (IL)-17 through IL-6 paracrine/autocrine loop. J Biol Chem. 2003 May 9; 278(19): 17036-43. Epub 2003 Mar. 06. (airway inflammation, asthma) |
| IL-6/IL-19 | Abstract IL-19 induces production of IL-6 and TNF-alpha and results in cell apoptosis through TNF-alpha. J Immunol. 2002 Oct. 15; 169(8): 4288-97. |
| IL-6/IFN-gamma | |
| IL-7/IL-2 | Interleukin 7 worsens graft-versus-host disease. Blood. 2002 Oct. 1; 100(7): 2642-9. |
| IL-7/IL-12 | Synergistic effects of IL-7 and IL-12 on human T cell activation. J Immunol. 1995 May 15; 154(10): 5093-102. |
| IL-7/IL-15 | Interleukin-7 and interleukin-15 regulate the expression of the bcl-2 and c-myb genes in cutaneous T-cell lymphoma cells. Blood. 2001 Nov. 1; 198(9): 2778-83. (growth factor) |
| IL-8/IL-11 | Abnormal production of interleukin (IL)-11 and IL-8 in polycythaemia vera. Cytokine. 2002 Nov. 21; 20(4): 178-83. |
| IL-8/IL-17 | The Role of IL-17 in Joint Destruction. Drug News Perspect. 2002 January; 15(1): 17-23. (arthritis) Abstract Interleukin-17 stimulates the expression of interleukin-8, growth-related oncogene-alpha, and granulocyte-colony-stimulating factor by human airway epithelial cells. Am J Respir Cell Mol Biol. 2002 June; 26(6): 748-53. (airway inflammation) |
| IL-8/GSF | Interleukin-8: an autocrine/paracrine growth factor for human hematopoietic progenitors acting in synergy with colony stimulating factor-1 to promote monocyte-macrophage growth and differentiation. Exp Hematol. 1999 January; 27(1): 28-36. |
| IL-8/VGEF | Intracavitary VEGF, bFGF, IL-8, IL-12 levels in primary and recurrent malignant glioma. J Neurooncol. 2003 May; 62(3): 297-303. |
| IL-9/IL-4 | Anti-interleukin-9 antibody treatment inhibits airway inflammation and hyperreactivity in mouse asthma model. Am J Respir Crit Care Med. 2002 Aug. 1; 166(3): 409-16. |
| IL-9/IL-5 | Pulmonary overexpression of IL-9 induces Th2 cytokine expression, leading to immune pathology. J Clin Invest. 2002 January; 109(1): 29-39. Th2 cytokines and asthma. Interleukin-9 as a therapeutic target for asthma. Respir Res. 2001; 2(2): 80-4. Epub 2001 Feb. 15. Review. Abstract Interleukin-9 enhances interleukin-5 receptor expression, differentiation, and survival of human eosinophils. Blood. 2000 Sep. 15; 96(6): 2163-71 (asthma) |
| IL-9/IL-13 | Anti-interleukin-9 antibody treatment inhibits airway inflammation and hyperreactivity in mouse asthma model. Am J Respir Crit Care Med. 2002 Aug. 1; 166(3): 409-16. Direct effects of interleukin-13 on epithelial cells cause airway hyperreactivity and mucus overproduction in asthma. Nat Med. 2002 August; 8(8): 885-9. |
| IL-9/IL-16 | See IL-4/IL-16 |
| IL-10/IL-2 | The interplay of interleukin-10 (IL-10) and interleukin-2 (IL-2) in humoral immune responses: IL-10 synergizes with IL-2 to enhance responses of human B lymphocytes in a mechanism which is different from upregulation of CD25 expression. Cell Immunol. 1994 September; 157(2): 478-88. |
| IL-10/IL-12 | |
| IL-10/TGF-β | IL-10 and TGF-beta cooperate in the regulatory T cell response to mucosal allergens in normal immunity and specific immunotherapy. Eur J Immunol. 2003 May; 33(5): 1205-14. |
| IL-10/IFN-gamma | |
| IL-11/IL-6 | Interleukin-6 and interleukin-11 support human osteoclast formation by a RANKL-independent mechanism. Bone. 2003 January; 32(1): 1-7. (bone resorption in inflammation) |
| IL-11/IL-17 | Polarized in vivo expression of IL-11 and IL-17 between acute and chronic skin lesions. J Allergy Clin Immunol. 2003 April; 111(4): 875-81. (allergic dermatitis) IL-17 promotes bone erosion in murine collagen-induced arthritis through loss of the receptor activator of NF-kappa B ligand/osteoprotegerin balance. J Immunol. 2003 Mar. 1; 170(5): 2655-62. |
| IL-11/TGF-β | Polarized in vivo expression of IL-11 and IL-17 between acute and chronic skin lesions. J Allergy Clin Immunol. 2003 April; 111(4): 875-81. (allergic dermatitis) |
| IL-12/IL-13 | Relationship of Interleukin-12 and Interleukin-13 imbalance with class-specific rheumatoid factors and anticardiolipin antibodies in systemic lupus erythematosus. Clin Rheumatol. 2003 May; 22(2): 107-11. |
| IL-12/IL-17 | Upregulation of interleukin-12 and -17 in active inflammatory bowel disease. Scand J Gastroenterol. 2003 February; 38(2): 180-5. |

TABLE 5-continued

| Pairing | Therapeutic relevant references. |
|---|---|
| IL-12/IL-18 | Synergistic proliferation and activation of natural killer cells by interleukin 12 and interleukin 18. Cytokine. 1999 November; 11(11): 822-30. Inflammatory Liver Steatosis Caused by IL-12 and IL-18. J Interferon Cytokine Res. 2003 March; 23(3): 155-62. |
| IL-12/IL-23 | nterleukin-23 rather than interleukin-12 is the critical cytokine for autoimmune inflammation of the brain. Nature. 2003 Feb. 13; 421(6924): 744-8. Abstract A unique role for IL-23 in promoting cellular immunity. J Leukoc Biol. 2003 January; 73(1): 49-56. Review. |
| IL-12/IL-27 | Abstract IL-27, a heterodimeric cytokine composed of EBB and p28 protein, induces proliferation of naive CD4(+) T cells. Immunity. 2002 June; 16(6): 779-90. |
| IL-12/IFN-γ | IL-12 induces IFN-γ expression by B and T-cells as part of immune stimulation. |
| IL-13/IL-5 | See IL-5/IL-13 |
| IL-13/IL-25 | Abstract New IL-17 family members promote Th1 or Th2 responses in the lung: in vivo function of the novel cytokine IL-25. J Immunol. 2002 Jul. 1; 169(1): 443-53. (allergic inflammation) Abstract Mast cells produce interleukin-25 upon Fcepsilon RI-mediated activation. Blood. 2003 May 1; 101(9): 3594-6. Epub 2003 Jan. 02. (allergic inflammation) |
| IL-15/IL-13 | Differential expression of interleukins (IL)-13 and IL-15 in ectopic and eutopic endometrium of women with endometriosis and normal fertile women. Am J Reprod Immunol. 2003 February; 49(2): 75-83. |
| IL-15/IL-16 | IL-15 and IL-16 overexpression in cutaneous T-cell lymphomas: stage-dependent increase in mycosis fungoides progression. Exp Dermatol. 2000 August; 9(4): 248-51. |
| IL-15/IL-17 | Abstract IL-17, produced by lymphocytes and neutrophils, is necessary for lipopolysaccharide-induced airway neutrophilia: IL-15 as a possible trigger. J Immunol. 2003 Feb. 15; 170(4): 2106-12. (airway inflammation) |
| IL-15/IL-21 | IL-21 in Synergy with IL-15 or IL-18 Enhances IFN-gamma Production in Human NK and T Cells. J Immunol. 2003 Jun. 1; 170(11): 5464-9. |
| IL-17/IL-23 | Interleukin-23 promotes a distinct CD4 T cell activation state characterized by the production of interleukin-17. J Biol Chem. 2003 Jan. 17; 278(3): 1910-4. Epub 2002 Nov. 03 |
| IL-17/TGF-β | Polarized in vivo expression of IL-11 and IL-17 between acute and chronic skin lesions. J Allergy Clin Immunol. 2003 April; 111(4): 875-81. (allergic dermatitis) |
| IL-18/IL-12 | Synergistic proliferation and activation of natural killer cells by interleukin 12 and interleukin 18. Cytokine. 1999 November; 11(11): 822-30. Abstract Inhibition of in vitro immunoglobulin production by IL-12 in murine chronic graft-vs.-host disease: synergism with IL-18. Eur J Immunol. 1998 June; 28(6): 2017-24. |
| IL-18/IL-21 | IL-21 in Synergy with IL-15 or IL-18 Enhances IFN-gamma Production in Human NK and T Cells. J Immunol. 2003 Jun. 1; 170(11): 5464-9. |
| IL-18/TGF-β | Interleukin 18 and transforming growth factor beta1 in the serum of patients with Graves' ophthalmopathy treated with corticosteroids. Int Immunopharmacol. 2003 April; 3(4): 549-52. |
| IL-18/IFN-α | |
| Anti-TNF ALPHA/anti-CD4 | Synergistic therapeutic effect in DBA/1 arthritic mice. |

TABLE 6

Oncology combinations

| Target | Disease | Can Pair with |
|---|---|---|
| CD89* | Use as cytotoxic cell recruiter | All |
| CD19 | B cell lymphomas | HLA-DR |
| | | CD5 |
| HLA-DR | B cell lymphomas | CD89 |
| | | CD19 |
| | | CD5 |
| CD38 | Multiple myeloma | CD138 |
| | | CD56 |
| | | HLA-DR |
| CD138 | Multiple myeloma | CD38 |
| | | CD56 |
| | | HLA-DR |
| CD138 | Lung cancer | CD56 |
| | | CEA |
| CD33 | Acute myelod lymphoma | CD34 |
| | | HLA-DR |
| CD56 | Lung cancer | CD138 |
| | | CEA |
| CEA | Pan carcinoma | MET receptor |
| VEGF | Pan carcinoma | MET receptor |
| VEGF receptor | Pan carcinoma | MET receptor |
| IL-13 | Asthma/pulmonary inflammation | IL-4 |
| | | IL-5 |
| | | Eotaxin(s) |
| | | MDC |

TABLE 6-continued

Oncology combinations

| Target | Disease | Can Pair with |
|---|---|---|
| IL-4 | Asthma | TARC |
| | | TNFα |
| | | IL-9 |
| | | EGFR |
| | | CD40L |
| | | IL-25 |
| | | MCP-1 |
| | | TGFβ |
| | | IL-13 |
| | | IL-5 |
| | | Eotaxin(s) |
| | | MDC |
| Eotaxin | Asthma | TARC |
| | | TNFα |
| | | IL-9 |
| | | EGFR |
| | | CD40L |
| | | IL-25 |
| | | MCP-1 |
| | | TGFβ |
| | | IL-5 |
| | | Eotaxin-2 |
| | | Eotaxin-3 |
| EGFR | cancer | HER2/neu |
| | | HER3 |
| | | HER4 |
| HER2 | cancer | HER3 |
| | | HER4 |
| TNFR1 | RA/Crohn's disease | IL-1R |
| | | IL-6R |
| | | IL-18R |
| TNFα | RA/Crohn's disease | IL-1α/β |
| | | IL-6 |
| | | IL-18 |
| | | ICAM-1 |
| | | IL-15 |
| | | IL-17 |
| IL-1R | RA/Crohn's disease | IL-6R |
| | | IL-18R |
| IL-18R | RA/Crohn's disease | IL-6R |

TABLE 7

In line fusion proteins which comprise a domain antibody (dAb) which is an anti-EGFR dAb designated DOM16-39-618 (S12P) fused to an anti-serum albumin dAb designated a DOM7 dAb

| N terminal dAb | Linker | C terminal dAb |
|---|---|---|
| DOM16-39-618 (S12P) | TVAAPS | DOM7h-14 |
| DOM16-39-618 (S12P) | TVAAPS | iDOM7h-14 |
| DOM7h-14 | TVAAPS | DOM16-39-618 (S12P) |
| DOM7h-14 | TVAAPS | DOM16-39-618 (S12P) |
| DOM16-39-618 (S12P) | TVAAPS | DOM7r-16 |
| DOM16-39-618 (S12P) | TVAAPS | iDOM7r-16 |
| DOM7r-16 | TVAAPS | DOM16-39-618 (S12P) |
| DOM7r-16 | TVAAPS | DOM16-39-618 (S12P) |

TABLE 8

Potency of anti TNF in line fusions

| Sample | Neutralisation EC50 |
|---|---|
| PEP1-5-19(S12P)-TVA-DOM7H-8 | 17 nm |
| PEP1-5-19 Monomer (old sample) | 64 nm |
| PEP1-5-19 Monomer (standard) | 30 nm |

Table 9: Potency of Anti IL-1 in Line Fusions

TABLE 9

Potency of anti IL-1 in line fusions

| Sample | Neutralisation EC50 |
|---|---|
| IL-1RA | 63 pM (n = 2) |
| DOM4-130-93 | 848 pM |
| DOM4-130-93(S12P)-TVA-DOM7H-8 | 136 pM |
| DOM4-130-54(S12P)-TVAAPS-DOM7H-10 | 179 pM |

This application incorporates by reference the material in the ASCII text file named DB00033USSeqList.txt created on 21 Jul. 2011 and having a size of 18,054 bytes.

REFERENCES

1. Nowak, M. (2004) *Proteins* 55, 11-21.
2. Raffen, R., Dieckman, L. J., Szpunar, M., Wunschl, C., Pokkuluri, P. R., Dave, P., Wilkins Stevens, P., Cai, X., Schiffer, M. & Stevens, F. J. (1999) *Protein Sci* 8, 509-17.
3. Krebs, M. R., Macphee, C. E., Miller, A. F., Dunlop, I. E., Dobson, C. M. & Donald, A. M. (2004) *Proc Natl Acad Sci USA* 101, 14420-4.
4. Jin, L. W., Claborn, K. A., Kurimoto, M., Geday, M. A., Maezawa, I., Sohraby, F., Estrada, M., Kaminksy, W. & Kahr, B. (2003) *Proc Natl Acad Sci USA* 100, 15294-8.
5. Pepys, M. B., Booth, D. R., Hutchinson, W. L., Gallimore, J. R., Collins, P. M. and Hohenester, E. (1997) *Amyloid: Int. J. Exp. Clin. Invest* 4, 274-295.
6. Hawkins, P. N., Lavender, J. P. and Pepys, M. B. (1990) *N. Engl. J. Med.* 323, 508-513.
7. Serpell, L. C., Sunde, M., Benson, M. D., Tennent, G. A., Pepys, M. B. & Fraser, P. E. (2000) *J Mol Biol* 300, 1033-9.
8. Schormann, N., Murrell, J. R., Liepnieks, J. J. & Benson, M. D. (1995) *Proc Natl Acad Sci USA* 92, 9490-4.
9. Graille, M., Stura, E. A., Housden, N. G., Beckingham, J. A., Bottomley, S. P., Beale, D., Taussig, M. J., Sutton, B. J., Gore, M. G. & Charbonnier, J. B. (2001) *Structure (Camb)* 9, 679-87.
10. Richardson, J. S. & Richardson, D. C. (2002) *Proc Natl Acad Sci USA* 99, 2754-9.
11. Siepen, J. A., Radford, S. E. & Westhead, D. R. (2003) *Protein Sci* 12, 2348-59.
12. Serag, A. A., Altenbach, C., Gingery, M., Hubbell, W. L. & Yeates, T. O. (2002) *Nat Struct Biol* 9, 734-9.
13. Ivanova, M. I., Sawaya, M. R., Gingery, M., Attinger, A. & Eisenberg, D. (2004) *Proc Natl Acad Sci USA* 101, 10584-9.
14. Nelson, R., Sawaya, M. R., Balbirnie, M., Madsen, A. O., Riekel, C., Grothe, R. & Eisenberg, D. (2005) *Nature* 435, 773-8.
15. Chien, P., DePace, A. H., Collins, S. R. & Weissman, J. S. (2003) *Nature* 424, 948-51.
16. Zhou, A., Stein, P. E., Huntington, J. A., Sivasothy, P., Lomas, D. A. & Carrell, R. W. (2004) *J Mol Biol* 342, 931-41.
17. Chiti, F., Stefani, M., Taddei, N., Ramponi, G. & Dobson, C. M. (2003) *Nature* 424, 805-8.
18. O'Nuallain, B., Williams, A. D., Westermark, P. & Wetzel, R. (2004) *J Biol Chem* 279, 17490-9.
19. Stevens, F. J. (2000) *Amyloid* 7, 200-11.
20. Asl, K. H., Liepnieks, J. J., Nunery, W. R., Yazaki, M. & Benson, M. D. (2004) *Amyloid* 11, 179-83.

21. Abraham, R. S., Geyer, S. M., Price-Troska, T. L., Allmer, C., Kyle, R. A., Gertz, M. A. & Fonseca, R. (2003) *Blood* 101, 3801-8.
22. Moyle, W. R., Lin, C., Corson, R. L. & Ehrlich, P. H. (1983) *Mol Immunol* 20, 439-52.
23. Nowakowski, A., Wang, C., Powers, D. B., Amersdorfer, P., Smith, T. J., Montgomery, V. A., Sheridan, R., Blake, R., Smith, L. A. & Marks, J. D. (2002) *Proc Natl Acad Sci USA* 99, 11346-50.
24. Tennent, G. (1999) *Amyloid, Prions and Other Protein Aggregates.* (Academic Press Ltd, San Diego, Calif.).
25. Zurdo J, G. J., Jimenez J L, Saibil H R and Dobson C M. (2001) *J. Mol. Biol.* 311, 325-340.
26. Tennent, G. A., Lovat, L. B. & Pepys, M. B. (1995) *Proc Natl Acad Sci USA* 92, 4299-303.
27. Pace, C. N. S., J. M. (1997) *Protein Structure, A Practical Approach* (Oxford University Press, New York.
28. Myers, J. K., Pace, C. N. & Scholtz, J. M. (1995) *Protein Sci.* 4, 2138-2148.
29. CCP4. (1994) *Acta. Cryst.* D50, 760-763.
30. Storoni, L. C., McCoy, A. J. & Read, R. J. (2004) *Acta Crystallogr D Biol Crystallogr* 60, 432-8.
31. Denoroy, L., Deret, S. & Aucouturier, P. (1994) *Immunol. Lett.* 42, 63-6
32. Souillac, P. O., Uversky, V. N. & Fink, A. L. (2003) *Biochemistry* 42, 8094-104.
33. Graille, M. et al. (2001) *Structure* 9, 679-687
34. Graille, M. et al. (2002) *J. Biol. Chem.* 277, 47500-47506
35. Kastern, W. et al. (1992) *J. Biol. Chem.* 267, 12820-12825
36. Kastern et al. (1990) Infect. Immun 58, 1217-22
37. Patella V et al. (1990) J. Immunol. 145, 3054-61
38. Genovese A et al. (2000) Infect. Immun. 68, 5517-24
39. Clackson, T. & Wells, J. A. (1995) *Science* 267, 383-6.
40. DeLano, W. L., Ultsch, M. H., de Vos, A. M. & Wells, J. A. (2000) *Science* 287, 1279-83.
41. Reches, M., Porat, Y. & Gazit, E. (2002) *J Biol Chem* 277, 35475-80.
42. Makin, O, S., Atkins, E., Sikorski, P., Johansson, J. & Serpell, L. C. (2005) *Proc Natl Acad Sci USA* 102, 315-20.
43. Deret, S., Chomilier, J., Huang, D. B., Preud'homme, J. L., Stevens, F. J. & Aucouturier, P. (1997) *Protein Eng* 10, 1191-7.
44. Khamlichi, A. A., Rocca, A., Touchard, G., Aucouturier, P., Preud'homme, J. L. & Cogne, M. (1995) *Blood* 86, 3655-9.
45. Jager, M. & Pluckthun, A. (1997) *FEBS Lett* 418, 106-10.
46. Spada, S., Honegger, A. & Pluckthun, A. (1998) *J Mol Biol* 283, 395-407.
47. Calarese, D. A., Scanlan, C. N., Zwick, M. B., Deechongkit, S., Mimura, Y., Kunert, R., Zhu, P., Wormald, M. R., Stanfield, R. L., Roux, K. H., Kelly, J. W., Rudd, P. M., Dwek, R. A., Katinger, H., Burton, D. R. & Wilson, I. A. (2003) *Science* 300, 2065-71.
48. Derrick J P & Wigley D B, (1992) Nature 359, 752-754.
49. Derrick J P & Wigley D B, (1994) J. Mol. Biol. 243, 906-918.

We claim:

1. An isolated antibody comprising a light chain variable domain framework 1 region having at least one amino acid substitution selected from the group consisting of a Kabat position 9 amino acid substitution, a Kabat position 10 amino acid substitution, a Kabat position 11 amino acid modification substitution, a Kabat position 12 amino acid substitution, a Kabat position 13 amino acid substitution and a Kabat position 14 amino acid modification substitution; wherein:

the Kabat position 9 amino acid substitution is selected from the group consisting of proline, tryptophan and tyrosine;

the Kabat position 10 amino acid substitution is selected from the group consisting of tryptophan, leucine and tyrosine;

the Kabat position 11 amino acid substitution is selected from the group consisting of proline, tryptophan, phenylalanine, and tyrosine;

the Kabat position 12 amino acid substitution is selected from the group consisting of tryptophan, phenylalanine, leucine and tyrosine;

the Kabat position 13 amino acid substitution is selected from the group consisting of tryptophan, phenylalanine, leucine and tyrosine; and the Kabat position 14 amino acid substitution is selected from the group consisting of proline, tryptophan, phenylalanine, leucine and tyrosine.

2. The antibody of claim 1, wherein:

the Kabat position 9 amino acid substitution is proline; and the Kabat position 11 amino acid substitution is proline.

3. The antibody of claim 1, wherein the antibody is selected from the group consisting of a chimeric antibody, a humanized antibody and a human antibody.

4. The antibody of claim 1, that is a multimer.

5. The antibody of claim 4, wherein the multimer is a dimer or a trimer.

6. The antibody of claim 4, further comprising a constituent antibody subunit having a proline at Kabat position 12 of a light chain variable domain framework 1 region.

7. The antibody of claim 6, wherein at least one constituent antibody subunit further comprises one amino acid substitution selected from the group consisting of a leucine at Kabat position 9 of a light chain variable domain framework 1 region and a proline at Kabat position 10 of a light chain variable domain framework 1 region.

8. The antibody of claim 1, further comprising at least one moiety selected from the group consisting of a cytotoxic moiety and a detectable moiety.

9. A pharmaceutical formulation comprising the antibody of claim 1 in an admixture with a pharmaceutically acceptable substance selected from the group consisting of an excipient, diluent and carrier.

10. A pharmaceutical formulation comprising the antibody of claim 1 in an admixture with a veterinarily acceptable substance selected from the group consisting of an excipient, diluent and carrier.

11. An isolated antigen binding fragment of an antibody comprising a light chain variable domain framework 1 region having at least one amino acid substitution selected from the group consisting of a Kabat position 9 amino acid substitution, a Kabat position 10 amino acid substitution, a Kabat position 11 amino acid substitution, a Kabat position 12 amino acid substitution, a Kabat position 13 amino acid substitution and a Kabat position 14 amino acid substitution; wherein:
  the Kabat position 9 amino acid substitution is selected from the group consisting of proline, tryptophan and tyrosine;
  the Kabat position 10 amino acid substitution is selected from the group consisting of tryptophan, leucine and tyrosine;
  the Kabat position 11 amino acid substitution is selected from the group consisting of proline, tryptophan, phenylalanine, and tyrosine;
  the Kabat position 12 amino acid substitution is selected from the group consisting of tryptophan, phenylalanine, leucine and tyrosine;
  the Kabat position 13 amino acid substitution is selected from the group consisting of tryptophan, phenylalanine, leucine and tyrosine; and
  the Kabat position 14 amino acid substitution is selected from the group consisting of proline, tryptophan, phenylalanine, leucine and tyrosine.

12. The antigen binding fragment of claim 11, wherein:
  the Kabat position 9 amino acid substitution is proline; and
  the Kabat position 11 amino acid substitution is proline.

13. The antigen binding fragment of claim 11, wherein the antigen binding fragment is selected from the group consisting of a $F_v$ fragment and a Fab fragment.

14. The antigen binding fragment of claim 11, wherein the antigen binding fragment is selected from the group consisting of a single chain $F_v$ and a disulfide bonded $F_v$.

15. The antigen binding fragment of claim 11, wherein the antigen binding fragment is selected from the group consisting of a Fab' fragment and a F(ab')$_2$ fragment.

16. The antigen binding fragment of claim 11, that is a multimer.

17. The antigen binding fragment of claim 16, wherein the multimer is a dimer or a trimer.

18. The antigen binding fragment of claim 16, further comprising a constituent antigen binding fragment subunit having a proline at Kabat position 12 of a light chain variable domain framework 1 region.

19. The antigen binding fragment of claim 18, wherein at least one constituent antigen binding fragment subunit further comprises one amino acid substitution selected from the group consisting of a leucine at Kabat position 9 of a light chain variable domain framework 1 region and a proline at Kabat position 10 of a light chain variable domain framework 1 region.

20. The antigen binding fragment of claim 11, further comprising at least one moiety selected from the group consisting of a cytotoxic moiety and a detectable moiety.

21. A pharmaceutical formulation comprising the antigen binding fragment of claim 11 in an admixture with a pharmaceutically acceptable substance selected from the group consisting of an excipient, diluent and carrier.

22. A pharmaceutical formulation comprising the antigen binding fragment of claim 11 in an admixture with a veterinarily acceptable substance selected from the group consisting of an excipient, diluent and carrier.

23. An isolated immunoglobulin single variable domain comprising a light chain variable domain framework 1 region having at least one amino acid substitution selected from the group consisting of a Kabat position 9 amino acid substitution, a Kabat position 10 amino acid substitution, a Kabat position 11 amino acid substitution, a Kabat position 12 amino acid substitution, a Kabat position 13 amino acid substitution and a Kabat position 14 amino acid substitution; wherein:
  the Kabat position 9 amino acid substitution is selected from the group consisting of proline, tryptophan, phenylalanine, leucine and tyrosine;
  the Kabat position 10 amino acid substitution is selected from the group consisting of tryptophan, leucine and tyrosine;
  the Kabat position 11 amino acid substitution is selected from the group consisting of proline, tryptophan, phenylalanine, leucine and tyrosine;
  the Kabat position 12 amino acid substitution is selected from the group consisting of proline, tryptophan, phenylalanine, leucine and tyrosine;
  the Kabat position 13 amino acid substitution is selected from the group consisting of tryptophan, phenylalanine, leucine and tyrosine; and
  the Kabat position 14 amino acid substitution is selected from the group consisting of proline, tryptophan, phenylalanine, leucine and tyrosine.

24. The immunoglobulin single variable domain of claim 23, wherein:
  the Kabat position 9 amino acid substitution is proline; the Kabat position 11 amino acid substitution is proline; the Kabat position 12 amino acid substitution is proline; and the Kabat position 14 amino acid modification substitution is proline.

25. The immunoglobulin single variable domain of claim 23, wherein the Kabat position 12 amino acid substitution is proline.

26. The immunoglobulin single variable domain of claim 23, that is a multimer.

27. The immunoglobulin single variable domain of claim 26, wherein the multimer is a dimer or a trimer.

28. The immunoglobulin single variable domain of claim 26, further comprising a constituent immunoglobulin single variable domain subunit having a proline at Kabat position 12 of a light chain variable domain framework 1 region.

29. The immunoglobulin single variable domain of claim 28, wherein at least one constituent immunoglobulin single variable domain subunit further comprises one amino acid substitution selected from the group consisting of a leucine at Kabat position 9 of a light chain variable domain framework 1 region and a proline at Kabat position 10 of a light chain variable domain framework 1 region.

30. The immunoglobulin single variable domain of claim 23, further comprising at least one moiety selected from the group consisting of a cytotoxic moiety and a detectable moiety.

31. A pharmaceutical formulation comprising the immunoglobulin single variable domain of claim 23 in an admixture with a pharmaceutically acceptable substance selected from the group consisting of an excipient, diluent and carrier.

32. A pharmaceutical formulation comprising the immunoglobulin single variable domain of claim 23 in an admixture with a veterinarily acceptable substance selected from the group consisting of an excipient, diluent and carrier.

33. An isolated antibody comprising a light chain variable domain framework 1 region having at least one amino acid selected from the group consisting of a Kabat position 9 amino acid, a Kabat position 10 amino acid, a Kabat position 11 amino acid, a Kabat position 12 amino acid, a Kabat position 13 amino acid and a Kabat position 14 amino acid; wherein:
the Kabat position 9 amino acid is selected from the group consisting of proline, tryptophan and tyrosine;
the Kabat position 10 amino acid is selected from the group consisting of tryptophan, leucine and tyrosine;
the Kabat position 11 amino acid is selected from the group consisting of proline, tryptophan, phenylalanine, and tyrosine;
the Kabat position 12 amino acid is selected from the group consisting of tryptophan, phenylalanine, leucine and tyrosine;
the Kabat position 13 amino acid is selected from the group consisting of tryptophan, phenylalanine, leucine and tyrosine; and
the Kabat position 14 amino acid is selected from the group consisting of proline, tryptophan, phenylalanine, leucine and tyrosine.

34. The antibody of claim 33, wherein:
the Kabat position 9 amino acid is proline; and
the Kabat position 11 amino acid is proline.

35. The antibody of claim 33, wherein the antibody is selected from the group consisting of a chimeric antibody, a humanized antibody and a human antibody.

36. The antibody of claim 33, that is a multimer.

37. The antibody of claim 36, wherein the multimer is a dimer or a trimer.

38. The antibody of claim 36, further comprising a constituent antibody subunit having a proline at Kabat position 12 of a light chain variable domain framework 1 region.

39. The antibody of claim 38, wherein at least one constituent antibody subunit further comprises one amino acid selected from the group consisting of a leucine at Kabat position 9 of a light chain variable domain framework 1 region and a proline at Kabat position 10 of a light chain variable domain framework 1 region.

40. The antibody of claim 33, further comprising at least one moiety selected from the group consisting of a cytotoxic moiety and a detectable moiety.

41. A pharmaceutical formulation comprising the antibody of claim 33 in an admixture with a pharmaceutically acceptable substance selected from the group consisting of an excipient, diluent and carrier.

42. A pharmaceutical formulation comprising the antibody of claim 33 in an admixture with a veterinarily acceptable substance selected from the group consisting of an excipient, diluent and carrier.

43. An isolated antigen binding fragment of an antibody comprising a light chain variable domain framework 1 region having at least one amino acid substitution selected from the group consisting of a Kabat position 9 amino acid, a Kabat position 10 amino acid, a Kabat position 11 amino acid, a Kabat position 12 amino acid, a Kabat position 13 amino acid and a Kabat position 14 amino acid; wherein:
the Kabat position 9 amino acid is selected from the group consisting of proline, tryptophan and tyrosine;
the Kabat position 10 amino acid is selected from the group consisting of tryptophan, leucine and tyrosine;
the Kabat position 11 amino acid is selected from the group consisting of proline, tryptophan, phenylalanine, and tyrosine;
the Kabat position 12 amino acid is selected from the group consisting of tryptophan, phenylalanine, leucine and tyrosine;
the Kabat position 13 amino acid is selected from the group consisting of tryptophan, phenylalanine, leucine and tyrosine; and
the Kabat position 14 amino acid is selected from the group consisting of proline, tryptophan, phenylalanine, leucine and tyrosine.

44. The antigen binding fragment of claim 43, wherein:
the Kabat position 9 amino acid is proline; and
the Kabat position 11 amino acid is proline.

45. The antigen binding fragment of claim 43, wherein the antigen binding fragment is selected from the group consisting of a $F_v$ fragment and a Fab fragment.

46. The antigen binding fragment of claim 43, wherein the antigen binding fragment is selected from the group consisting of a single chain $F_v$ and a disulfide bonded $F_v$.

47. The antigen binding fragment of claim 43, wherein the antigen binding fragment is selected from the group consisting of a Fab' fragment and a $F(ab')_2$ fragment.

48. The antigen binding fragment of claim 43, that is a multimer.

49. The antigen binding fragment of claim 48, wherein the multimer is a dimer or a trimer.

50. The antigen binding fragment of claim 48, further comprising a constituent antigen binding fragment subunit having a proline at Kabat position 12 of a light chain variable domain framework 1 region.

51. The antigen binding fragment of claim 50, wherein at least one constituent antigen binding fragment subunit further comprises one amino acid selected from the group consisting of a leucine at Kabat position 9 of a light chain variable domain framework 1 region and a proline at Kabat position 10 of a light chain variable domain framework 1 region.

52. The antigen binding fragment of claim 43, further comprising at least one moiety selected from the group consisting of a cytotoxic moiety and a detectable moiety.

53. A pharmaceutical formulation comprising the antigen binding fragment of claim 43 in an admixture with a pharmaceutically acceptable substance selected from the group consisting of an excipient, diluent and carrier.

54. A pharmaceutical formulation comprising the antigen binding fragment of claim 43 in an admixture with a veterinarily acceptable substance selected from the group consisting of an excipient, diluent and carrier.

55. An isolated immunoglobulin single variable domain comprising a light chain variable domain framework 1 region having at least one amino acid selected from the group consisting of a Kabat position 9 amino acid, a Kabat position 10 amino acid, a Kabat position 11 amino acid, a Kabat position 12 amino acid, a Kabat position 13 amino acid and a Kabat position 14 amino acid; wherein:
the Kabat position 9 amino acid is selected from the group consisting of proline, tryptophan, phenylalanine, leucine and tyrosine;
the Kabat position 10 amino acid is selected from the group consisting of tryptophan, leucine and tyrosine;
the Kabat position 11 amino acid is selected from the group consisting of proline, tryptophan, phenylalanine, leucine and tyrosine;
the Kabat position 12 amino acid is selected from the group consisting of proline, tryptophan, phenylalanine, leucine and tyrosine;
the Kabat position 13 amino acid is selected from the group consisting of tryptophan, phenylalanine, leucine and tyrosine; and
the Kabat position 14 amino acid is selected from the group consisting of proline, tryptophan, phenylalanine, leucine and tyrosine.

56. The immunoglobulin single variable domain of claim 55, wherein:
the Kabat position 9 amino acid is proline; the Kabat position 11 amino acid is proline; the Kabat position 12 amino acid is proline; and the Kabat position 14 amino acid is proline.

57. The immunoglobulin single variable domain of claim 55, wherein the Kabat position 12 amino acid is proline.

58. The immunoglobulin single variable domain of claim 55, that is a multimer.

59. The immunoglobulin single variable domain of claim 58, wherein the multimer is a dimer or a trimer.

60. The immunoglobulin single variable domain of claim 58, further comprising a constituent immunoglobulin single variable domain subunit having a proline at Kabat position 12 of a light chain variable domain framework 1 region.

61. The immunoglobulin single variable domain of claim 60, wherein at least one constituent immunoglobulin single variable domain subunit further comprises one amino acid selected from the group consisting of a leucine at Kabat position 9 of a light chain variable domain framework 1 region and a proline at Kabat position 10 of a light chain variable domain framework 1 region.

62. The immunoglobulin single variable domain of claim 55, further comprising at least one moiety selected from the group consisting of a cytotoxic moiety and a detectable moiety.

63. A pharmaceutical formulation comprising the immunoglobulin single variable domain of claim 55 in an admixture with a pharmaceutically acceptable substance selected from the group consisting of an excipient, diluent and carrier.

64. A pharmaceutical formulation comprising the immunoglobulin single variable domain of claim 55 in an admixture with a veterinarily acceptable substance selected from the group consisting of an excipient, diluent and carrier.

65. An isolated antibody comprising a light chain variable domain framework 1 region wherein the amino acid at Kabat position 9 is selected from the group consisting of proline, tryptophan and tyrosine.

66. An isolated antibody comprising a light chain variable domain framework 1 region wherein the amino acid at Kabat position 10 is selected from the group consisting of tryptophan, leucine and tyrosine.

67. An isolated antibody comprising a light chain variable domain framework 1 region wherein the amino acid at Kabat position 11 is selected from the group consisting of proline, tryptophan, phenylalanine and tyrosine.

68. An isolated antibody comprising a light chain variable domain framework 1 region wherein the amino acid at Kabat position 12 is selected from the group consisting of tryptophan, phenylalanine, leucine and tyrosine.

69. An isolated antibody comprising a light chain variable domain framework 1 region wherein the amino acid at Kabat position 13 is selected from the group consisting of tryptophan, phenylalanine, leucine and tyrosine.

70. An isolated antibody comprising a light chain variable domain framework 1 region wherein the amino acid at Kabat position 14 is selected from the group consisting of proline, tryptophan, phenylalanine, leucine and tyrosine.

71. An isolated antigen binding fragment of an antibody comprising a light chain variable domain framework 1 region wherein the amino acid at Kabat position 9 is selected from the group consisting of proline, tryptophan and tyrosine.

72. An isolated antigen binding fragment of an antibody comprising a light chain variable domain framework 1 region wherein the amino acid at Kabat position 10 is selected from the group consisting of tryptophan, leucine and tyrosine.

73. An isolated antigen binding fragment of an antibody comprising a light chain variable domain framework 1 region wherein the amino acid at Kabat position 11 is selected from the group consisting of proline, tryptophan, phenylalanine and tyrosine.

74. An isolated antigen binding fragment of an antibody comprising a light chain variable domain framework 1 region wherein the amino acid at Kabat position 12 is selected from the group consisting of tryptophan, phenylalanine, leucine and tyrosine.

75. An isolated antigen binding fragment of an antibody comprising a light chain variable domain framework 1 region wherein the amino acid at Kabat position 13 is selected from the group consisting of tryptophan, phenylalanine, leucine and tyrosine.

76. An isolated antigen binding fragment of an antibody comprising a light chain variable domain framework 1 region wherein the amino acid at Kabat position 14 is selected from the group consisting of proline, tryptophan, phenylalanine, leucine and tyrosine.

77. An isolated immunoglobulin single variable domain comprising a light chain variable domain framework 1 region wherein the amino acid at Kabat position 9 is selected from the group consisting of proline, tryptophan, phenylalanine, leucine and tyrosine.

78. An isolated immunoglobulin single variable domain comprising a light chain variable domain framework 1 region wherein the amino acid at Kabat position 10 is selected from the group consisting of tryptophan, leucine and tyrosine.

79. An isolated immunoglobulin single variable domain comprising a light chain variable domain framework 1 region wherein the amino acid at Kabat position 11 is selected from the group consisting of proline, tryptophan, phenylalanine, leucine and tyrosine.

80. An isolated immunoglobulin single variable domain comprising a light chain variable domain framework 1 region wherein the amino acid at Kabat position 12 is selected from the group consisting of proline, tryptophan, phenylalanine, leucine and tyrosine.

81. An isolated immunoglobulin single variable domain comprising a light chain variable domain framework 1 region wherein the amino acid at Kabat position 13 is selected from the group consisting of tryptophan, phenylalanine, leucine and tyrosine.

82. An isolated immunoglobulin single variable domain comprising a light chain variable domain framework 1 region wherein the amino acid at Kabat position 14 is selected from the group consisting of proline, tryptophan, phenylalanine, leucine and tyrosine.

83. An isolated immunoglobulin single variable domain comprising a light chain variable domain framework 1 region wherein the amino acid at Kabat position 12 is proline.

84. The immunoglobulin single variable domain of claim 83, wherein the amino acid at Kabat position 9 is leucine and the amino acid at Kabat position 10 is proline.

85. The immunoglobulin single variable domain of claim 83, wherein the amino acid at Kabat position 9 is leucine.

86. The immunoglobulin single variable domain of claim 83, wherein the amino acid at Kabat position 10 is proline.

* * * * *